(12) United States Patent
Brenneman et al.

(10) Patent No.: US 8,569,339 B2
(45) Date of Patent: Oct. 29, 2013

(54) SOLUBLE GUANYLATE CYCLASE ACTIVATORS

(75) Inventors: Jehrod Burnett Brenneman, Southbury, CT (US); John D. Huber, New York, NY (US); Brian Christopher Raudenbush, Brookfield, CT (US); Christopher Ronald Sarko, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/414,991

(22) Filed: Mar. 8, 2012

(65) Prior Publication Data

US 2013/0065918 A1    Mar. 14, 2013

Related U.S. Application Data

(60) Provisional application No. 61/451,163, filed on Mar. 10, 2011, provisional application No. 61/537,741, filed on Sep. 22, 2011.

(51) Int. Cl.
| | |
|---|---|
| *A61K 31/4725* | (2006.01) |
| *A61K 31/4439* | (2006.01) |
| *C07D 401/14* | (2006.01) |
| *C07D 409/14* | (2006.01) |
| *C07D 405/14* | (2006.01) |
| *C07D 413/14* | (2006.01) |
| *A61P 9/00* | (2006.01) |
| *A61P 29/00* | (2006.01) |
| *A61P 1/16* | (2006.01) |

(52) U.S. Cl.
USPC .......................................................... 514/307

(58) Field of Classification Search
USPC .......................................................... 514/307
See application file for complete search history.

(56) References Cited

U.S. PATENT DOCUMENTS

| | | |
|---|---|---|
| 2009/0209556 A1 | 8/2009 | Bittner et al. |
| 2010/0016305 A1 | 1/2010 | Krahn et al. |
| 2010/0216764 A1 | 8/2010 | Kim et al. |
| 2013/0065918 A1 | 3/2013 | Brenneman et al. |

FOREIGN PATENT DOCUMENTS

| | | |
|---|---|---|
| WO | 0226712 A2 | 4/2002 |
| WO | 2008021339 A2 | 2/2008 |
| WO | 2008138483 A1 | 11/2008 |
| WO | 2009032249 A1 | 3/2009 |
| WO | 2009068652 A1 | 6/2009 |
| WO | 2009071504 A1 | 6/2009 |
| WO | 2010015652 A2 | 2/2010 |
| WO | 2010015653 A1 | 2/2010 |
| WO | 2010065275 A1 | 6/2010 |
| WO | 2010099054 A2 | 9/2010 |
| WO | 2012058132 A1 | 5/2012 |
| WO | 2012122340 A1 | 9/2012 |
| WO | 2013025425 A1 | 2/2013 |

OTHER PUBLICATIONS

Evgenov, Oleg, V. et al., "NO-Independent Stimulators and Activators of Soluble Guanylate Cyclase: Discovery and Therapeutic Potential" Nature Reviews/Drug Discovery (2006) vol. 5 pp. 755-768.
International Search Report and Written Opinion for PCT/US2012/028205 mailed Jul. 4, 2012.
International Search Report for PCT/US2012/050052 mailed Oct. 22, 2012.
Schindler, Ursula., "Biochemistry and Pharmacology of Novel Anthranilic Acid Derivates Activating Heme-Oxidized Soluble Guanylyl Cyclase" Molecular Pharmacology (2006) vol. 69, No. 4 pp. 1260-1268.
Stasch, Johannes-Peter, et al., "NO- and HAEM-Independent Activation of Soluble Guanylyl Cyclase: Molecular Basis and Cardiovascular Implications of a New Pharmacological Principle" British Journal of Pharmacology (2002) vol. 136 pp. 773-783.
U.S. Appl. No. 61/697,899 filed Sep. 7, 2012.

*Primary Examiner* — Jeffrey S. Lundgren
*Assistant Examiner* — Zenab Olabowale
(74) *Attorney, Agent, or Firm* — Michael P. Morris; Edward S. Lazer

(57) ABSTRACT

The present invention relates to compounds of formula (I):

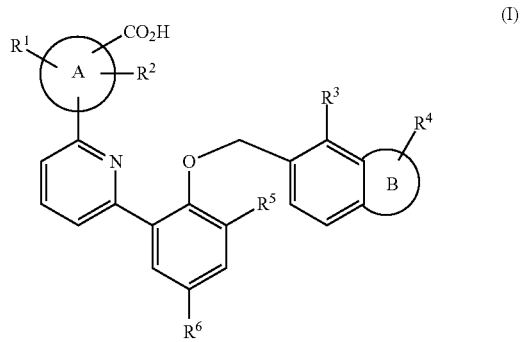

and pharmaceutically acceptable salts thereof, wherein $R^1$, $R^2$, $R^3$, $R^4$, $R^5$, $R^6$, A and B are as defined herein. The invention also relates to pharmaceutical compositions comprising these compounds, methods of using these compounds in the treatment of various diseases and disorders, processes for preparing these compounds and intermediates useful in these processes.

14 Claims, No Drawings

SOLUBLE GUANYLATE CYCLASE ACTIVATORS

FIELD OF THE INVENTION

This invention relates to heterocyclic compounds which are useful as activators of soluble guanylate cyclase and are thus useful for treating a variety of diseases that are mediated or sustained by decreased or diminished soluble guanylate cyclase activity, including cardiovascular diseases, renal disease, diabetes, fibrotic disorders, urologic disorders, neurological disorders and inflammatory disorders. This invention also relates to pharmaceutical compositions comprising these compounds, methods of using these compounds in the treatment of various diseases and disorders, processes for preparing these compounds and intermediates useful in these processes.

BACKGROUND

Soluble guanylate cyclase (sGC) is a receptor for nitric oxide (NO) which is found in the cytoplasm of many cell types. In humans, functional sGC is a heterodimer composed of either an alpha 1 or alpha 2 subunit combined with the beta 1 subunit which has a heme prosthetic group. Under non-pathophysiological conditions, NO binding to the heme of sGC activates the enzyme to catalyze the conversion of guanosine-5'-triphosphate (GTP) to cyclic guanosine monophosphate (cGMP). cGMP is a second messenger which exerts effects by modulating cGMP dependent protein kinase (PKG) isoforms, phosphodiesterases, and cGMP gated ion channels. In doing so, sGC has been demonstrated to modulate numerous pathways associated with diseases including arterial hypertension, pulmonary hypertension, atherosclerosis, heart failure, liver cirrhosis, renal fibrosis, and erectile dysfunction (O. Evgenov et al., Nature Reviews, 2006, 5, 755-768 and Y. Wang-Rosenke et al., Curr. Med. Chem., 2008, 15, 1396-1406).

Under normal conditions, the iron in sGC exists in the ferrous state which is capable of binding to NO and carbon monoxide (CO). However, under conditions of oxidative stress which can occur in various diseases, published reports indicate that the heme iron becomes oxidized to the ferric state which is incapable of being activated by NO or CO. The inability of NO to signal through sGC with an oxidized heme iron has been hypothesized to contribute to disease processes. Recently, two novel classes of compounds have been described which potentiate sGC activity in a heme dependent (sGC stimulators) and heme independent (sGC activators) manner. The activity of sGC stimulators synergizes with NO to increase cGMP production while sGC activators are only additive with NO to augment cGMP levels (O. Evgenov et al., Nature Reviews, 2006, 5, 755-768). Both stimulators and activators of sGC have demonstrated benefit in animal models of disease. Activators of sGC provide the advantage of being able to preferentially target the diseased, non-functional form of the enzyme. sGC activators include BAY 58-2667 (cinaciguat) (J-P Stasch et al., Brit J. Pharmacol., 2002, 136, 773-783) and HMR-1766 (ataciguat) (U. Schindler et al., 2006, Mol. Pharmacol., 69, 1260-1268).

NO has an important role in maintaining normal cellular and tissue function. However, adequate signaling in the NO pathway can be disrupted at a number of steps. NO signaling can be impaired by reduced levels of nitric oxide synthase (NOS) enzymes, NOS activity, NO bioavailability, sGC levels, and sGC activity. sGC activators have the potential to bypass the functional impediment produced by all of these impairments. Since sGC activation occurs downstream of NO synthesis or NO availability, these deficiencies will not impact the activity of sGC activators. As described above, the activity of sGC in which function is disrupted by heme iron oxidation will be corrected by sGC activators. Thus, sGC activators have the potential to provide benefit in many diseases caused by defective signaling in the NO pathway.

Activation of sGC has the potential to provide therapeutic benefit for atherosclerosis and arteriosclerosis. Cinaciguat treatment has been demonstrated to prevent neointimal hyperplasia after endothelial denudation by wire injury of the carotid artery in rats (K. Hirschberg et al., Cardiovasc. Res., 2010, 87, Suppl. 1, S100, Abstract 343). Ataciguat inhibited atherosclerotic plaque formation in ApoE-/- mice feed a high fat diet (M. van Eickels, BMC Pharmacology, 2007, 7, Suppl. 1, S4). Decreased NO production in endothelial nitric oxide synthase (eNOS) deficient mice increased vascular inflammation and insulin resistance in response to nutrient excess. In the same study, the phosphodiesterase 5 (PDE5) inhibitor sildenafil reduced vascular inflammation and insulin resistance in mice fed a high-fat diet (N. Rizzo et al., Arterioscler. Thromb. Vasc. Biol., 2010, 30, 758-765). Lastly, after balloon-injury of rat carotid arteries in vivo, a sGC stimulator (YC-1) inhibited neotima formation (C. Wu, J. Pharmacol. Sci., 2004, 94, 252-260

The complications of diabetes may be reduced by sGC activation. Glucose induced suppression of glucagon release is lost in pancreatic islets that lack PKG, thus suggesting a role of sGC mediated cGMP production in glucose regulation (V. Leiss et al., BMC Pharmacology, 2009, 9, Suppl. 1, P40).

It is well established clinically that elevation of cGMP by treatment with PDE5 inhibitors is efficacious for the treatment of erectile dysfunction (ED). However, 30% of ED patients are resistant to PDE5 inhibitor treatment (S. Gur et al., Curr. Pharm. Des., 2010, 16, 1619-1633). The sGC stimulator BAY-41-2272 is able to relax corpus cavernosum muscle in a sGC dependent manner, thus suggesting that increased sGC activity could provide benefit in ED patients (C. Teixeira et al., J. Pharmacol. & Exp. Ther., 2007, 322, 1093-1102). Furthermore, sGC stimulators and sGC activators used individually or either in combination with PDE5 inhibitor was able to treat ED in animal models (WO 10/081,647).

There is evidence that sGC activation may be useful in preventing tissue fibrosis, including that of the lung, liver, and kidney. The processes of epithelial to mesenchyal transition (EMT) and fibroblast to myofibroblast conversion are believed to contribute to tissue fibrosis. When either cincaciguat or BAY 41-2272 was combined with sildenafil, lung fibroblast to myofibroblast conversion was inhibited (T. Dunkern et al., Eur. J. Pharm., 2007, 572, 12-22). NO is capable of inhibiting EMT of alveolar epithelial cells (S. Vyas-Read et al., Am. J. Physiol. Lung Cell Mol. Physiol., 2007, 293, 1212-1221), suggesting that sGC activation is involved in this process. NO has also been shown to inhibit glomerular TGF beta signaling (E. Dreieicher et al., J. Am. Soc. Nephrol., 2009, 20, 1963-1974) which indicates that sGC activation may be able to inhibit glomerular sclerosis. In a pig serum model and carbon tetrachloride model of liver fibrosis, an sGC activator (BAY 60-2260) was effective at inhibiting fibrosis (A. Knorr et al., Arzneimittel-Forschung, 2008, 58, 71-80).

Clinical studies have demonstrated efficacy using the sGC activator cinaciguat for the treatment of acute decompensated heart failure (H. Lapp et al., Circulation, 2009, 119, 2781-2788). This is consistent with results from a canine tachypacing-induced heart failure model in which acute intravenous infusion of cinaciguat was able to produce cardiac unloading (G. Boerrigter et al., Hypertension, 2007, 49, 1128-1133). In a rat myocardial infarction induced chronic heart failure model, HMR 1766 improved cardiac function and reduced cardiac fibrosis which was further potentiated by ramipril (F. Daniela, Circulation, 2009, 120, Suppl. 2, S852-S853).

Activators of sGC can be used to treat hypertension. This has been clearly demonstrated in clinical studies in which the dose of cinaciguat is titrated based on the magnitude of blood pressure reduction achieved (H. Lapp et al., Circulation, 2009, 119, 2781-2788). Preclinical studies using cinaciguat had previously shown the ability of sGC activation to reduce blood pressure (J.-P. Stasch et al., 2006, J. Clin. Invest., 116, 2552-2561). Similar findings have been reported using the sGC activator HMR 1766 as well (U. Schindler et al., 2006, Mol. Pharmacol., 69, 1260-1268).

The activation of sGC has the potential to reduce inflammation by effects on the endothelium. BAY 41-2272 and a NO donor inhibited leukocyte rolling and adhesion in eNOS deficient mice. This was demonstrated to be mediated by down-regulation of expression of the adhesion molecule P-selectin (A. Ahluwalla et al., Proc. Natl. Acad. Sci. USA, 2004, 101, 1386-1391). Inhibitors of NOS and sGC were shown to increase endotoxin (LPS) induced ICAM expression on mesenteric microcirculation vessels. This was reduced by an NO donor in a cGMP dependent manner. Treatment of mice with NOS or sGC inhibitors increased neutrophil migration, rolling, and adhesion induced by LPS or carrageenen (D. Dal Secco, Nitric Oxide, 2006, 15, 77-86). Activation of sGC has been shown to produce protection from ischemia-reperfusion injury using BAY 58-2667 in both in vivo and in an isolated heart model (T. Krieg et al., Eur. Heart J., 2009, 30, 1607-6013). Similar results were obtained using the same compound in a canine model of cardioplegic arrest and extracorporeal circulation (T. Radovits et al., Eur J. Cardiothorac. Surg., 2010).

Some studies have indicated the potential of sGC activation to have antinociceptive effects. In streptozotocin-induced diabetes models of nociception in mice (writhing assay) and rats (paw hyperalgesia), elevation of cGMP levels by administration of sildenafil blocked the pain response, which in turn was abrogated by a NOS or sGC inhibitor (C. Patil et al., Pharm., 2004, 72, 190-195). The sGC inhibitor 1H-1,2,4.-oxadiazolo-4,2-a.quinoxalin-1-one (ODQ) has been demonstrated to block the antinociceptive effects of various agents including meloxicam and diphenyl diselenide in a formalin induced pain model (P. Aguirre-Banuelos et al., Eur. J. Pharmacol., 2000, 395, 9-13 and L. Savegnago et al., J. Pharmacy Pharmacol., 2008, 60, 1679-1686) and xylazine in a paw pressure model (T. Romero et al., Eur. J. Pharmacol., 2009, 613, 64-67). Furthermore, ataciguat was antinociceptive in the carrageenan model of inflammatory triggered thermal hyperalgesia and the spared nerve injury model of neuropathic pain in mice (WO 09/043,495).

Inhibition of PDE9, a phosphodiesterase specific for cGMP expressed in the brain, has been shown to improve long-term potentiation (F. van der Staay et al., Neuropharmacol. 2008, 55, 908-918). In the central nervous system, sGC is the primary enzyme which catalyzes the formation of cGMP (K. Domek-Lopacinska et al., Mol. Neurobiol., 2010, 41, 129-137). Thus, sGC activation may be beneficial in treating Alzheimer's and Parkinson's disease. In a phase II clinical study, the sGC stimulator riociguat, was efficacous in treating chronic thromboembolic pulmonary hypertension and pulmonary arterial hypertension (H. Ghofrani et al., Eur. Respir. J., 2010, 36, 792-799). These findings extend the preclinical studies in which BAY 41-2272 and cinaciguat reduced pulmonary hypertension in mouse (R. Dumitrascu et al., Circulation, 2006, 113, 286-295) and lamb (O. Evgenov et al., 2007, Am. J. Respir. Crit. Care Med., 176, 1138-1145) models. Similar results were obtained using HMR 1766 in a mouse model of pulmonary hypertension (N. Weissmann et al., 2009, Am. J. Physiol, Lung Cell. Mol, Physiol., 297, L658-665).

Activation of sGC has the potential to treat chronic kidney disease. Both BAY 58-2667 and HMR 1766 improved renal function and structure in a rat subtotal nephrectomy model of kidney disease (P. Kalk et al., 2006, Brit. J. Pharmacol., 148, 853-859 and K. Benz et al., 2007, Kidney Blood Press. Res., 30, 224-233). Improved kidney function and survival was provided by BAY 58-2667 treatment in hypertensive renin transgenic rats (TG(mRen2)27 rats) treated with a NOS inhibitor (J.-P. Stasch et al., 2006, J. Clin. Invest., 116, 2552-2561). BAY 41-2272 treatment preserved kidney function and structure in a chronic model of kidney disease in rats induced by uninephrectomy and anti-thy1 antibody treatment (Y. Wang et al., 2005, Kidney Intl., 68, 47-61). Diseases caused by excessive blood clotting may be treated with sGC activators. Activation of sGC using BAY 58-2667 was capable of inhibiting platelet aggregation induced by various stimuli ex vivo. Additionally, this compound inhibited thrombus formation in vivo in mice and prolonged bleeding time (J.-P. Stasch et al., 2002, Brit. J. Pharmacol., 136, 773-783). In another study using HMR 1766, in vivo platelet activation was inhibited in streptozotocin treated rats (A. Schafer et al., 2006, Arterioscler. Thromb. Vasc. Biol., 2006, 26, 2813-2818).

sGC activation may also be beneficial in the treatment of urologic disorders (WO/08138483). This is supported by clinical studies using the PDE5 inhibitor vardenafil (C. Stief et al., 2008, Eur. Urol., 53, 1236-1244). The soluble guanylate cyclase stimulator BAY 41-8543 was able to inhibit prostatic, urethra, and bladder smooth muscle cell proliferation using patient samples (B. Fibbi et al., 2010, J. Sex. Med., 7, 59-69), thus providing further evidence supporting the utility of treating urologic disorders with sGC activators.

The above studies provide evidence for the use of sGC activators to treat cardiovascular diseases including hypertension, atherosclerosis, peripheral artery disease, restenosis, stroke, heart failure, coronary vasospasm, cerebral vasospasm, ischemia/reperfusion injury, thromboembolic pulmonary hypertension, pulmonary arterial hypertension, stable and unstable angina, thromboembolic disorders. Additionally, sGC activators have the potential to treat renal disease, diabetes, fibrotic disorders including those of the liver, kidney and lungs, urologic disorders including overactive bladder, benign pro static hyperplasia, and erectile dysfunction, and neurological disorders including Alzheimer's disease, Parkinson's disease, as well as neuropathic pain. Treatment with sGC activators may also provide benefits in inflammatory disorders such as psoriasis, multiple sclerosis, arthritis, asthma, and chronic obstructive pulmonary disease.

BRIEF SUMMARY OF THE INVENTION

The present invention provides novel compounds which activate or potentiate sGC and are thus useful for treating a variety of diseases and disorders that can be alleviated by sGC activation or potentiation including cardiovascular, inflammatory and renal diseases. This invention also relates to pharmaceutical compositions comprising these compounds, methods of using these compounds in the treatment of various diseases and disorders, processes for preparing these compounds and intermediates useful in these processes.

In a further aspect, the present invention provides activators of soluble guanylate cyclase having solubility properties consistent with acceptable pharmacokinetic properties. As is known in the art, poorly soluble compounds may suffer from poor human exposure. The compounds of the present invention would be expected to have exposure properties consistent with being a suitable drug.

DETAILED DESCRIPTION OF THE INVENTION

In an embodiment, there are provided compounds of the formula I

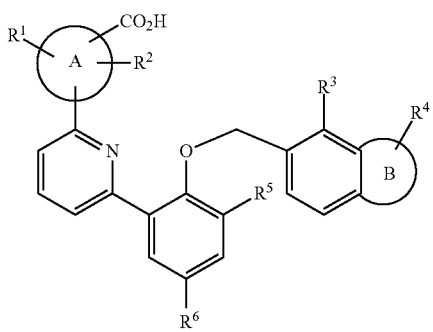

wherein:
A is a 5- or 6-membered aryl, heteroaryl or heterocyclyl group;
B is a 5-7 membered heterocyclyl group containing one nitrogen, wherein one carbon of the heterocyclyl group is optionally substituted with an oxo group, or B is a 5-membered heteroaryl group containing at least 2 nitrogens;
$R^1$ and $R^2$ are independently selected from H, $C_{1-4}$alkyl, $C_{3-6}$cycloalkyl, tetrahydropyranyl, —$CF_3$, —$CH_2CF_3$ and —$CH_2CH_2CO_2H$;
$R^3$ is selected from H and —$CH_3$;
$R^4$ is selected from H, $C_{1-6}$alkyl, $C_{3-7}$cycloalkyl, —C(O)$C_{1-6}$alkyl, —$CH_2CF_3$, —$SO_2C_{1-6}$alkyl, —$SO_2$ ($CH_2$)$_{1-3}CO_2H$, —$CO_2C_{1-4}$alkyl, heterocyclyl, aryl, heteroaryl, —($C_{1-2}$alkyl)heterocyclyl, —($C_{1-2}$alkyl)aryl and —($C_{1-2}$alkyl)heteroaryl, wherein said heterocyclyl, cycloalkyl, aryl and heteroaryl are optionally substituted with one to two groups independently selected from $C_{1-3}$alkyl, —$CF_3$, and halogen,
or $R^4$ is optionally not present when B is a heteroaryl group;
$R^5$ is selected from H, —$C_{1-3}$alkyl, —$OCH_3$, —$CF_3$, —CN and Cl; and
$R^6$ is selected from H and $CH_3$;
provided that $R^5$ and $R^6$ are not both H;
or a salt thereof.

In another embodiment, there are provided compounds as described in the embodiment above, wherein:
A is a 5- or 6-membered aryl, heteroaryl or heterocyclyl group;
B is a 5-7 membered heterocyclyl group containing one nitrogen, wherein one carbon of the heterocyclyl group is optionally substituted with an oxo group, or B is a 5-membered heteroaryl group containing at least 2 nitrogens;
$R^1$ and $R^2$ are independently selected from H, —$CH_3$ and —$CF_3$;
$R^3$ is selected from H and —$CH_3$;
$R^4$ is selected from H, $C_{1-6}$alkyl, $C_{3-6}$cycloalkyl, —C(O)$C_{1-6}$alkyl, —$SO_2C_{1-6}$alkyl, —$SO_2(CH_2)_{1-3}CO_2H$, —$CO_2C_{1-4}$alkyl, heterocyclyl, aryl, heteroaryl, —($C_{1-2}$alkyl)heterocyclyl, —($C_{1-2}$alkyl)aryl and —($C_{1-2}$alkyl)heteroaryl, wherein said heterocyclyl, cycloalkyl, aryl and heteroaryl are optionally substituted with $C_{1-3}$alkyl or —$CF_3$,
or $R^4$ is optionally not present when B is a heteroaryl group;
$R^5$ is H; and
$R^6$ is —$CH_3$;
or a salt thereof.

In another embodiment, there are provided compounds as described in any of the embodiments above, wherein:

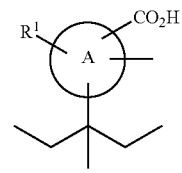

is a 5- or 6-membered aryl, heteroaryl or heterocyclyl group selected from:

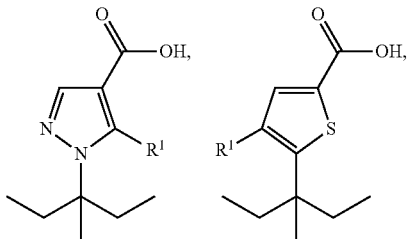

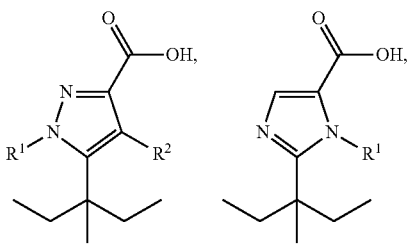

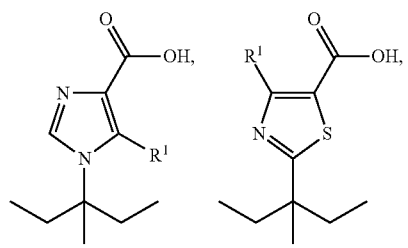

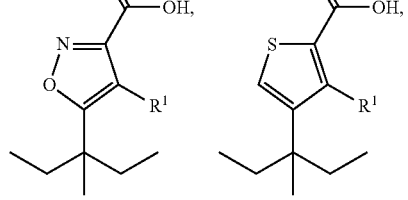

-continued
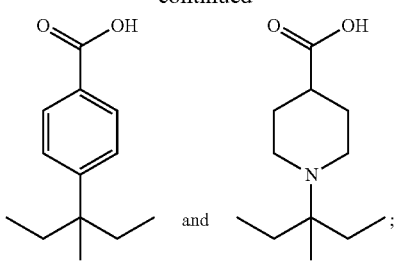
and
and the group
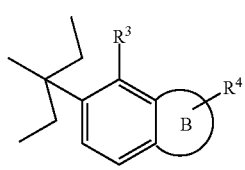
is selected from:
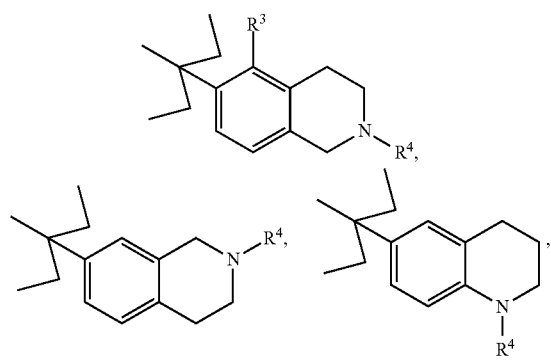
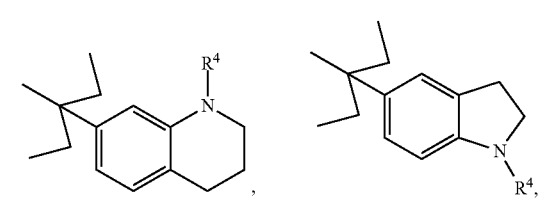
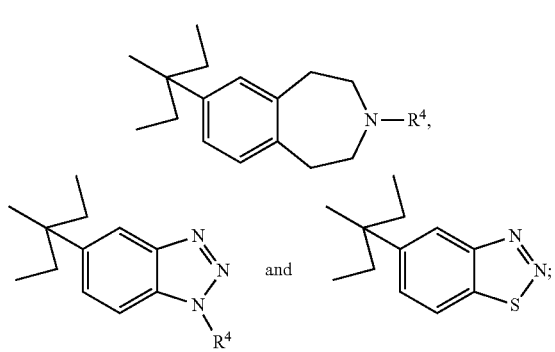
or a salt thereof.
In another embodiment, there are provided compounds as described in any of the embodiments above, wherein:
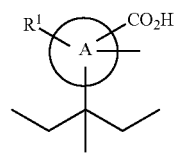
is a 5- or 6-membered aryl, heteroaryl or heterocyclyl group selected from:
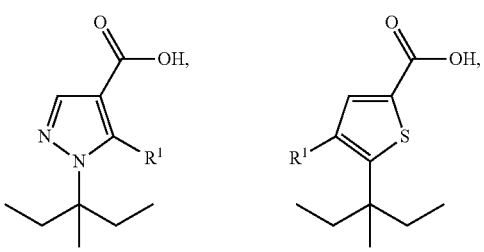
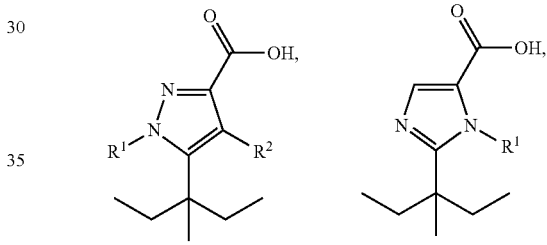
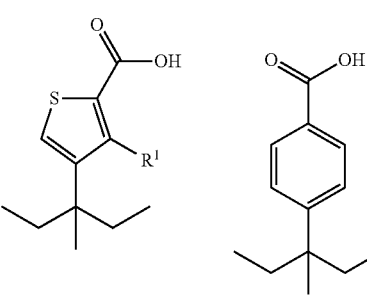
and
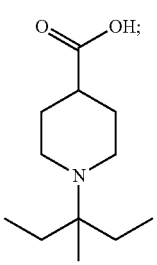
or a salt thereof.

In another embodiment there are compounds as described in any of the embodiments above above, wherein:
the group

[Structure: benzene ring fused with ring B, bearing R³ and R⁴ substituents and a quaternary carbon with ethyl/methyl groups]

is selected from:

[Structure: tetrahydroisoquinoline with R³ and R⁴]

[Structure: tetrahydroisoquinoline with R⁴], [Structure: tetrahydroquinoline with R⁴]

[Structure: tetrahydroquinoline with R⁴], [Structure: indoline with R⁴] and

[Structure: benzazepine with N–R⁴];

or a salt thereof.

In another embodiment there are compounds as described in any of the embodiments above above, wherein:

[Structure: ring A with R¹ and CO₂H substituents and quaternary carbon]

is selected from:

[Pyrazole-carboxylic acid with R¹], [Thiophene-carboxylic acid with R¹]

[Pyrazole-carboxylic acid with R¹, R²], [Imidazole-carboxylic acid with R¹] and

[Thiophene-carboxylic acid with R¹];

or a salt thereof.

In another embodiment there are compounds as described in any of the embodiments above above, wherein:

[Structure: benzene fused with ring B, R³, R⁴]

is:

[Structure: tetrahydroisoquinoline with R³ and R⁴];

or a salt thereof.

In another embodiment there are compounds as described in any of the embodiments above above, wherein:

[Structure: ring A with R¹ and CO₂H]

is:

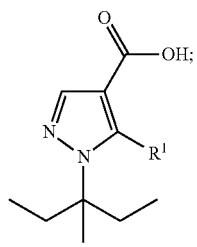

or a salt thereof.

In another embodiment there are compounds as described in any of the embodiments above above, wherein:

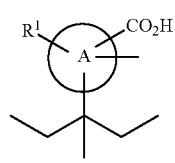

is:

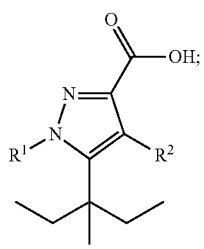

or a salt thereof.

In another embodiment there are compounds as described in any of the embodiments above above, wherein:
R¹ and R² are independently selected from H, $C_{1-4}$alkyl, cyclopropyl and —$CF_3$;
R⁴ is selected from H, $C_{1-6}$alkyl, $C_{3-7}$cycloalkyl, —C(O)$C_{1-6}$alkyl, —$CH_2CF_3$, —$SO_2C_{1-6}$alkyl, —$SO_2(CH_2)_{1-3}CO_2H$, —$CO_2C_{1-4}$alkyl, heterocyclyl, phenyl, heteroaryl, —($C_{1-2}$alkyl)heterocyclyl, —($C_{1-2}$alkyl)phenyl and —($C_{1-2}$alkyl)heteroaryl,
wherein said heterocyclyl is selected from tetrahydrofuranyl and tetrahydropyranyl, and
said heteroaryl is selected from imidazolyl, isoxazolyl, pyrazinyl, pyrazolyl, pyridinyl, pyrimidinyl, thiazolyl and 4,5,6,7-tetrahydrobenzothiazolyl,
wherein said heterocyclyl, cycloalkyl, phenyl and heteroaryl are optionally substituted with one to two groups independently selected from methyl, ethyl, —$CF_3$ and fluorine
R₅ is selected from —$CH_3$, —$CH_2CH_3$, —$OCH_3$, and —$CF_3$; and
R₆ is selected from H and —$CH_3$;
provided that R₅ and R₆ are not both H;
or a salt thereof.

In another embodiment there are compounds as described in any of the embodiments above above, wherein:
R⁴ is selected from H, $C_{1-6}$alkyl, $C_{3-6}$cycloalkyl, —C(O)$C_{1-6}$alkyl, —$SO_2C_{1-6}$alkyl, —$SO_2(CH_2)_{1-3}CO_2H$, heterocyclyl, phenyl, heteroaryl, —($C_{1-2}$alkyl)heterocyclyl, —($C_{1-2}$alkyl)phenyl and —($C_{1-2}$alkyl)heteroaryl,
wherein said heterocyclyl is selected from tetrahydrofuranyl and tetrahydropyranyl, and said heteroaryl is selected from imidazolyl, oxazolyl, pyrazinyl, pyrazolyl, pyridinyl, pyrimidinyl and thiazolyl,
and said heterocyclyl, phenyl and heteroaryl are optionally substituted with $C_{1-3}$alkyl or —$CF_3$;
or a salt thereof.

In another embodiment there are compounds as described in any of the embodiments above above, wherein:

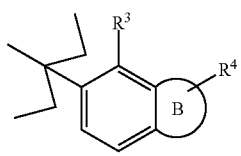

is:

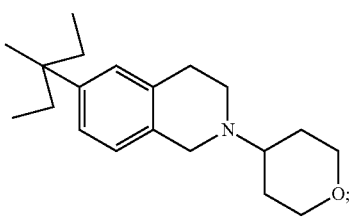 [SMILES: CCC(C)(CC)c1ccc2c(c1)CCN(C1CCOCC1)C2]

or a salt thereof.

In another embodiment there are compounds as described in any of the embodiments above above, wherein:

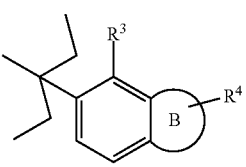

is:

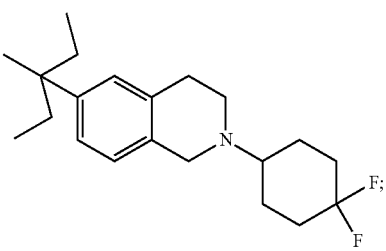 [SMILES: CCC(C)(CC)c1ccc2c(c1)CCN(C1CCC(F)(F)CC1)C2]

or a salt thereof.

The following are representative compounds of the invention which can be made by the general synthetic schemes, the examples, and known methods in the art.

TABLE 1
| Cpd No. | Structure |
|---|---|
| 1 | 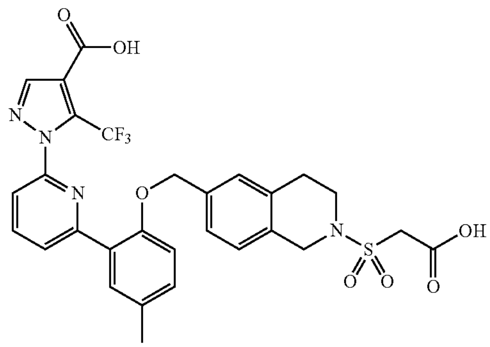 [SMILES: Cc1ccc(OCc2ccc3c(c2)CCN(S(=O)(=O)CC(=O)O)C3)c(-c2cccc(-n3ncc(C(=O)O)c3C(F)(F)F)n2)c1] |
| 2 | 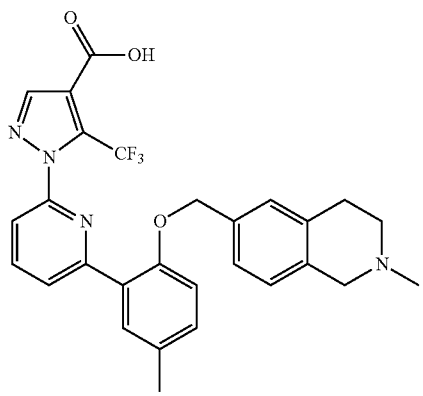 [SMILES: Cc1ccc(OCc2ccc3c(c2)CCN(C)C3)c(-c2cccc(-n3ncc(C(=O)O)c3C(F)(F)F)n2)c1] |
| 3 | 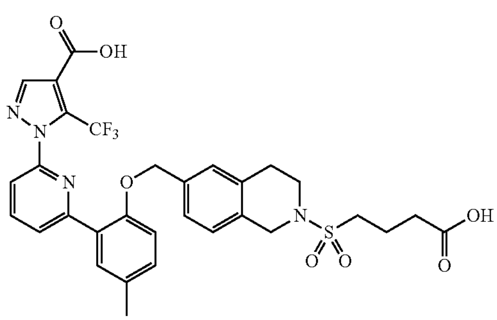 [SMILES: Cc1ccc(OCc2ccc3c(c2)CCN(S(=O)(=O)CCCC(=O)O)C3)c(-c2cccc(-n3ncc(C(=O)O)c3C(F)(F)F)n2)c1] |
| 4 | 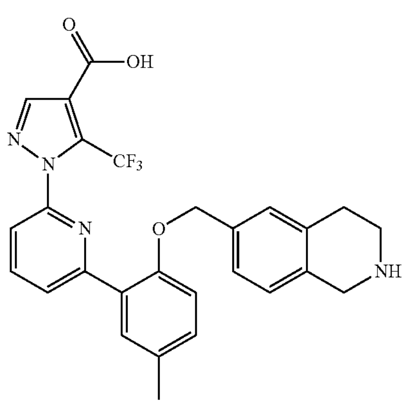 [SMILES: Cc1ccc(OCc2ccc3c(c2)CCNC3)c(-c2cccc(-n3ncc(C(=O)O)c3C(F)(F)F)n2)c1] |
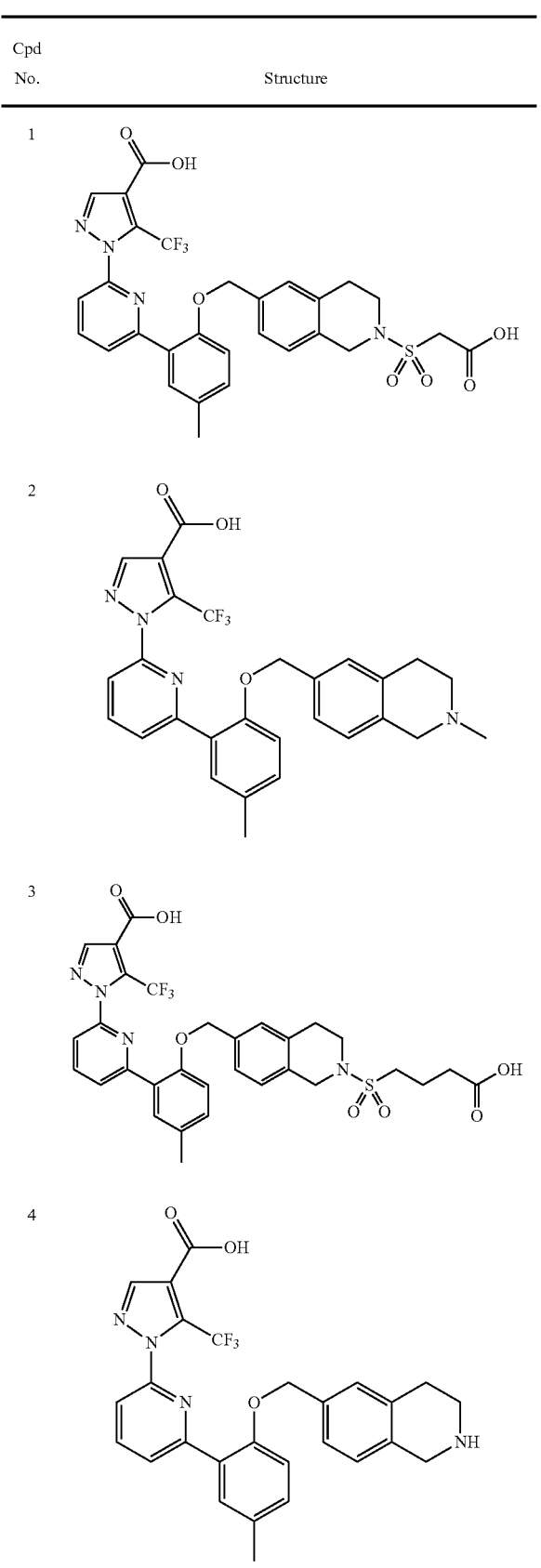
TABLE 1-continued
| Cpd No. | Structure |
|---|---|
| 5 | 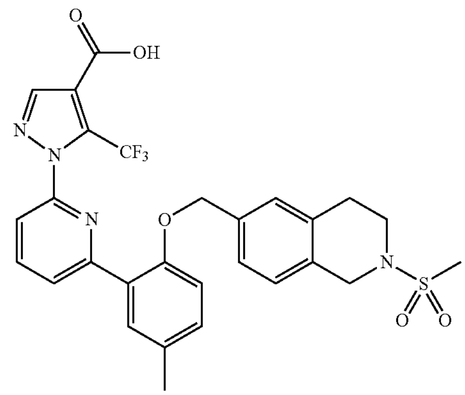 [SMILES: Cc1ccc(OCc2ccc3c(c2)CCN(S(C)(=O)=O)C3)c(-c2cccc(-n3ncc(C(=O)O)c3C(F)(F)F)n2)c1] |
| 6 | 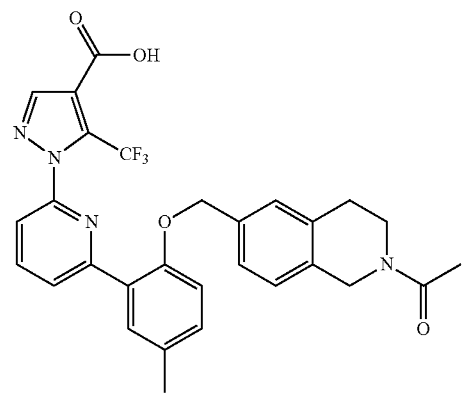 [SMILES: CC(=O)N1CCc2cc(COc3ccc(C)cc3-c3cccc(-n4ncc(C(=O)O)c4C(F)(F)F)n3)ccc2C1] |
| 7 | 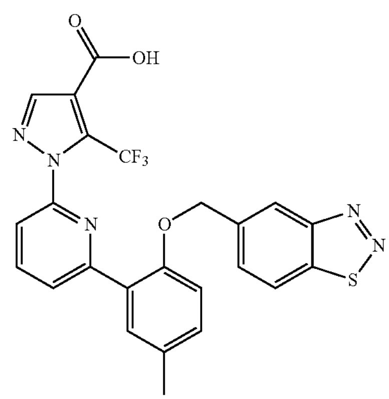 [SMILES: Cc1ccc(OCc2ccc3snnc3c2)c(-c2cccc(-n3ncc(C(=O)O)c3C(F)(F)F)n2)c1] |
| 8 | 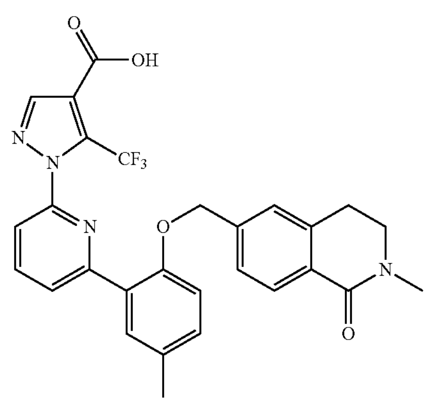 [SMILES: Cc1ccc(OCc2ccc3c(c2)CCN(C)C3=O)c(-c2cccc(-n3ncc(C(=O)O)c3C(F)(F)F)n2)c1] |
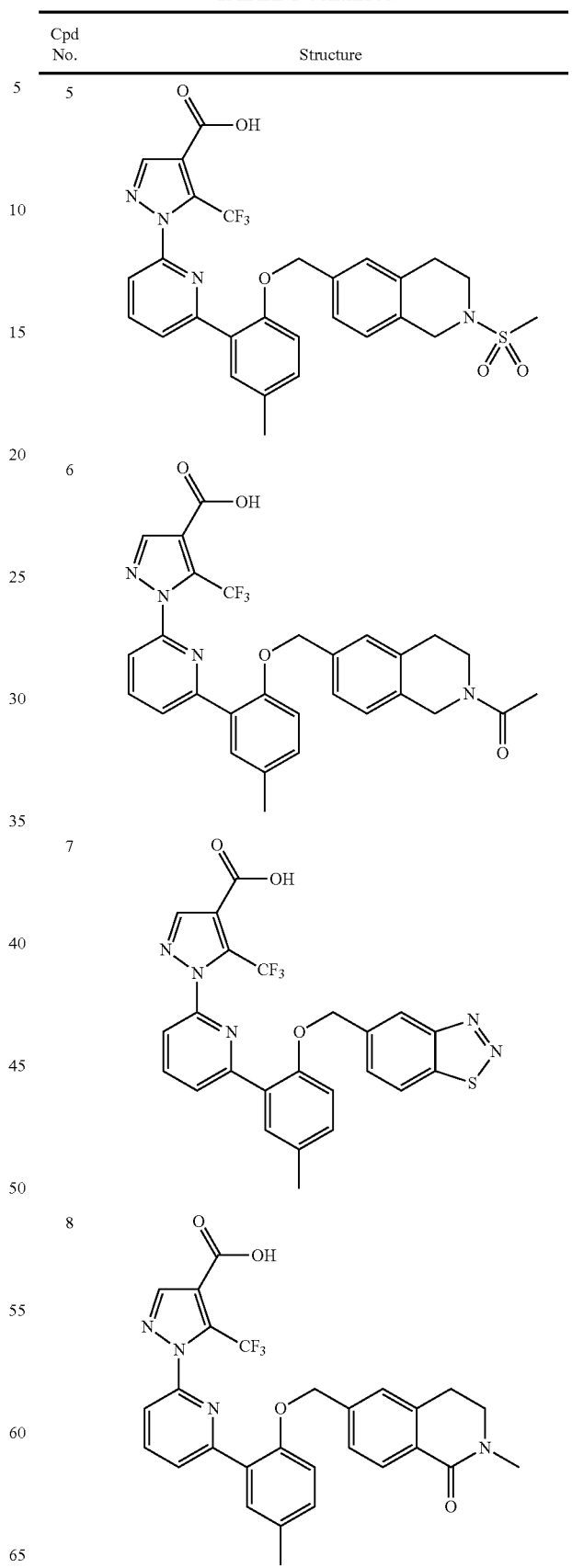

TABLE 1-continued

| Cpd No. | Structure |
|---|---|
| 9 | (structure) |
| 10 | (structure) |
| 11 | (structure) |
| 12 | (structure) |
| 13 | (structure) |
| 14 | (structure) |
| 15 | (structure) |
| 16 | (structure) |

TABLE 1-continued

| Cpd No. | Structure |
|---|---|
| 17 | *structure* |
| 18 | *structure* |
| 19 | *structure* |
| 20 | *structure* |
| 21 | *structure* |
| 22 | *structure* |
| 23 | *structure* |
| 24 | *structure* |

TABLE 1-continued
| Cpd No. | Structure |
|---|---|
| 25 | 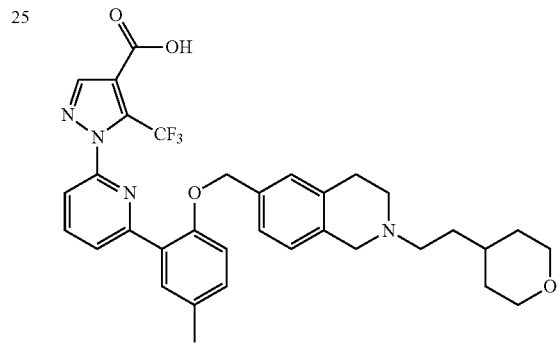 |
| 26 | 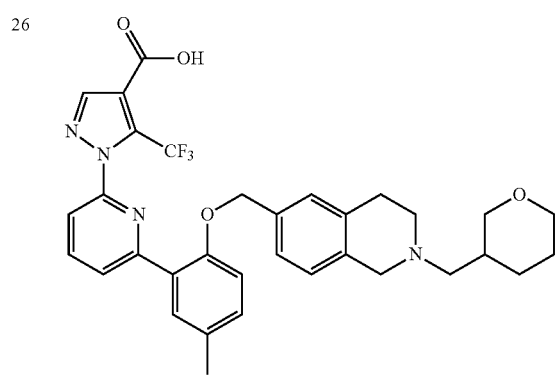 |
| 27 | 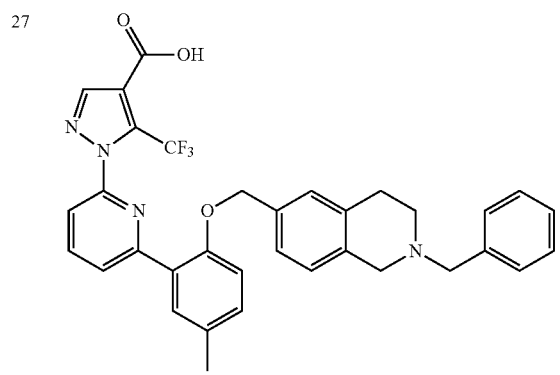 |
| 28 | 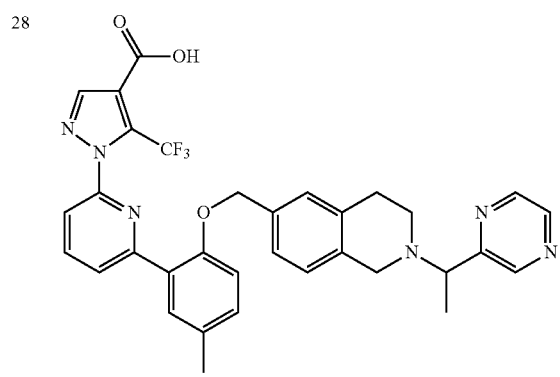 |
| 29 | 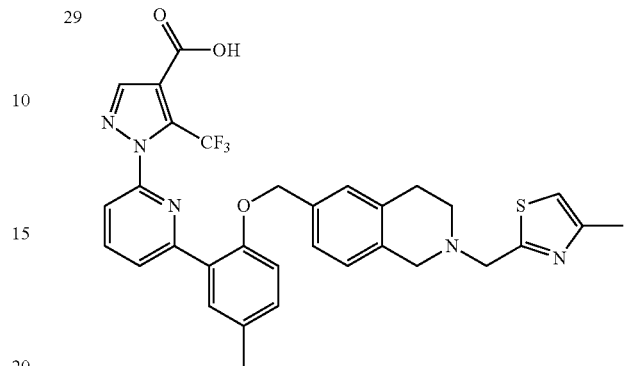 |
| 30 | 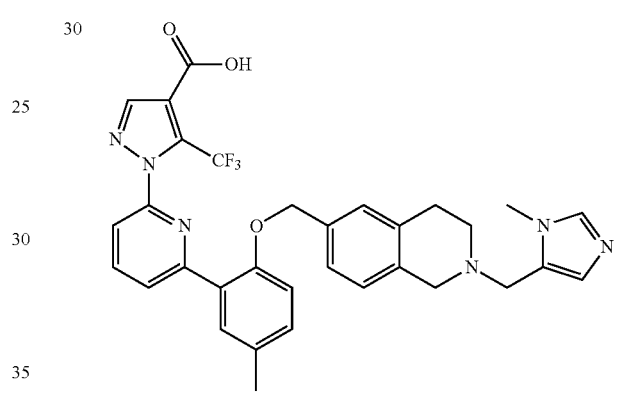 |
| 31 | 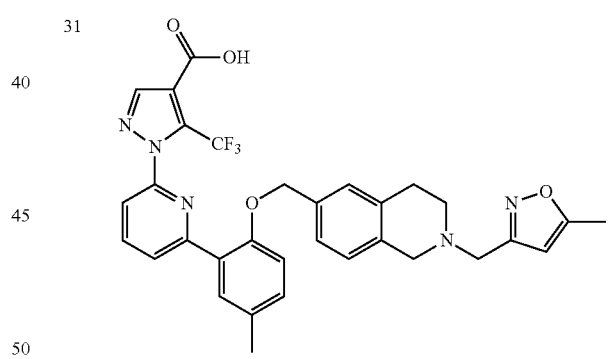 |
| 32 | 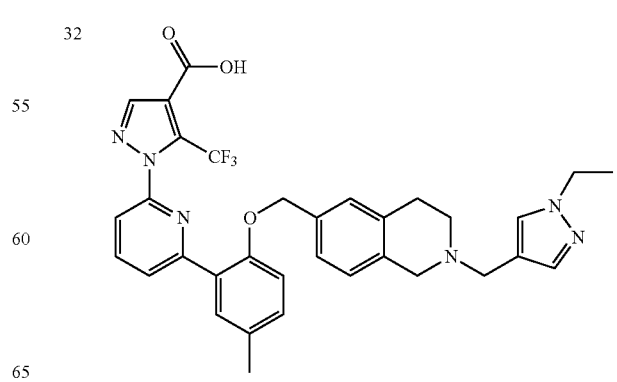 |

TABLE 1-continued

| Cpd No. | Structure |
|---|---|
| 33 | (structure) |
| 34 | (structure) |
| 35 | (structure) |
| 36 | (structure) |
| 37 | (structure) |
| 38 | (structure) |
| 39 | (structure) |
| 40 | (structure) |

TABLE 1-continued
| Cpd No. | Structure |
|---|---|
| 41 | 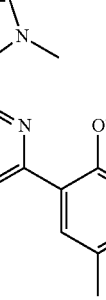 |
| 42 | 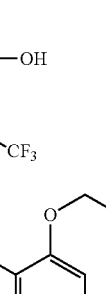 |
| 43 | 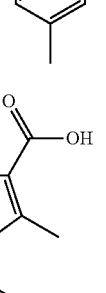 |
| 44 | 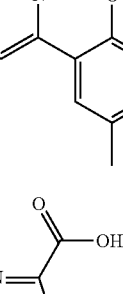 |
| 45 | 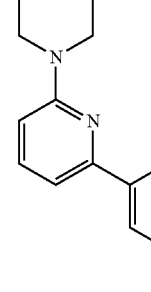 |
| 46 | 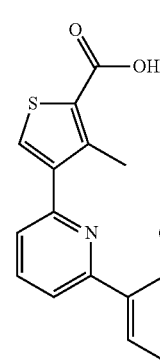 |
| 47 | 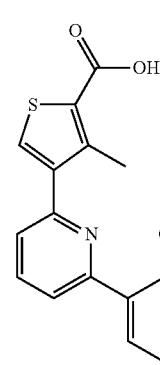 |
| 48 | 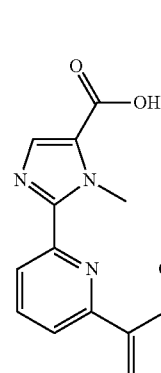 |

TABLE 1-continued

| Cpd No. | Structure |
|---|---|
| 49 | (structure) |
| 50 | (structure) |
| 51 | (structure) |
| 52 | (structure) |
| 53 | (structure) |
| 54 | (structure) |
| 55 | (structure) |

TABLE 1-continued
| Cpd No. | Structure |
|---|---|
| 56 | 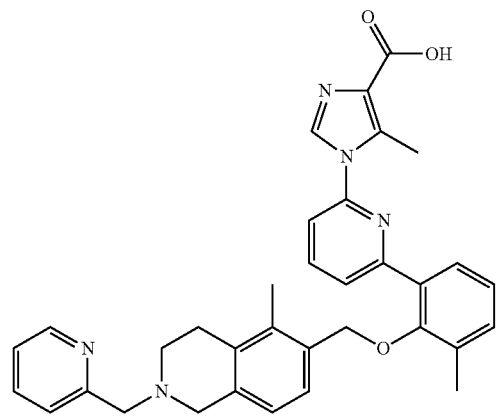 |
| 57 | 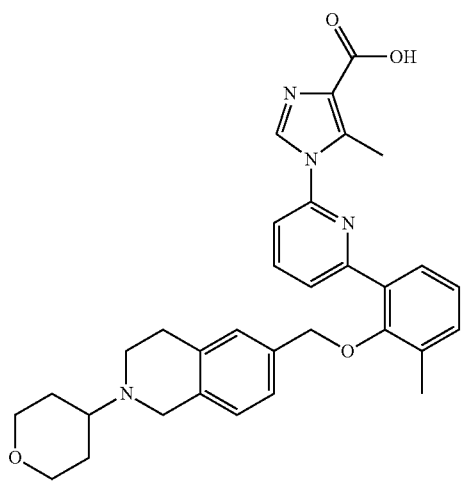 |
| 58 | 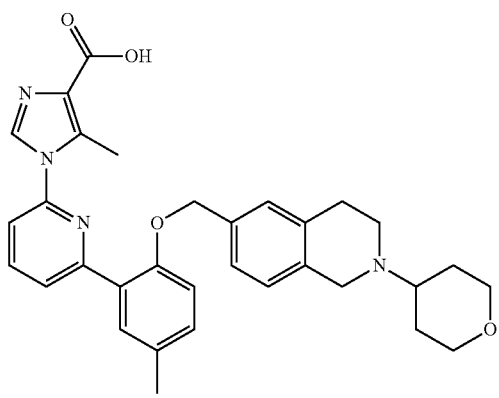 |
TABLE 1-continued
| Cpd No. | Structure |
|---|---|
| 59 | 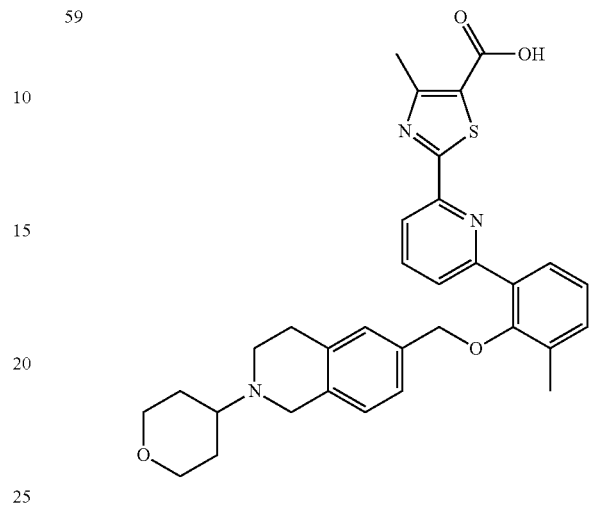 |
| 60 | 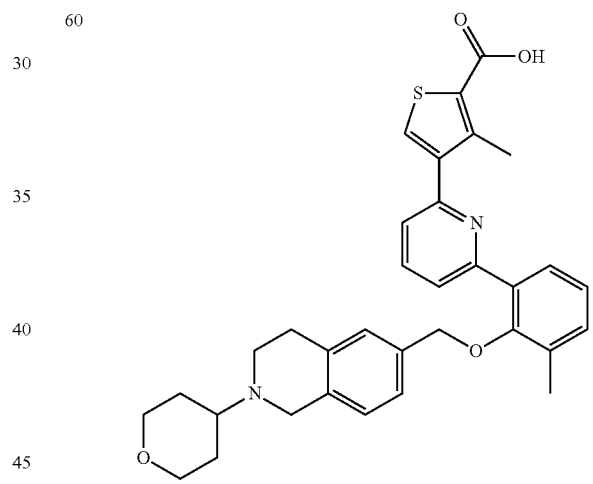 |
| 61 | 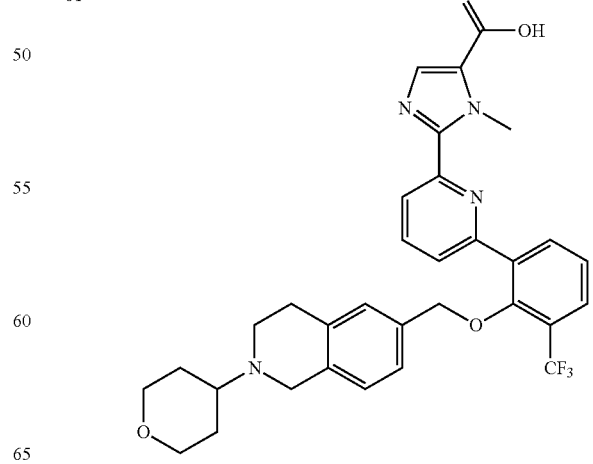 |

TABLE 1-continued

| Cpd No. | Structure |
|---|---|
| 62 | 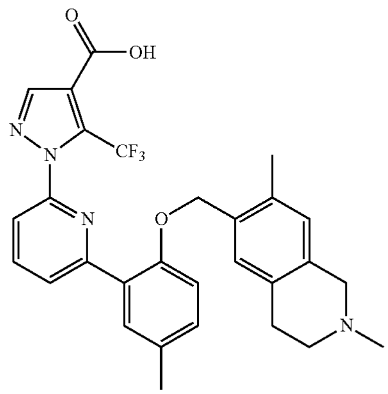 |
| 63 | 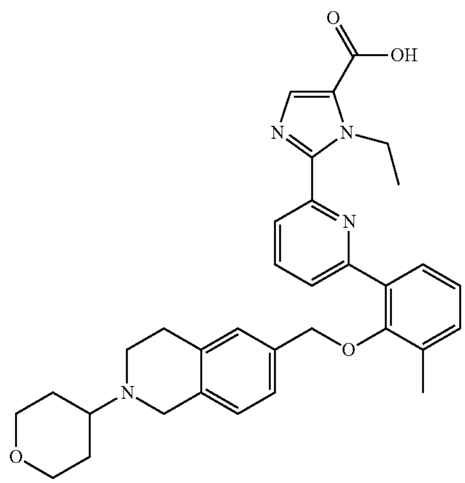 |
| 64 | 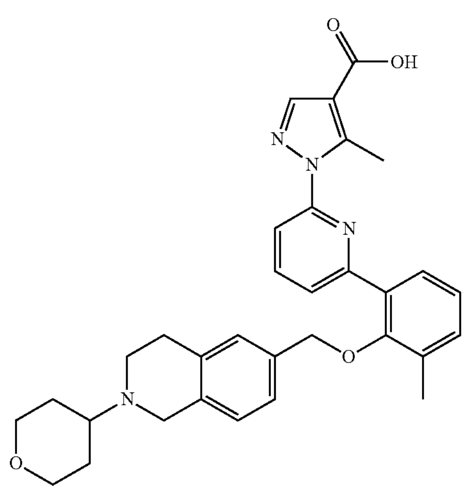 |
| 65 | |
| 66 | |
| 67 | |

TABLE 1-continued

| Cpd No. | Structure |
|---|---|
| 68 | 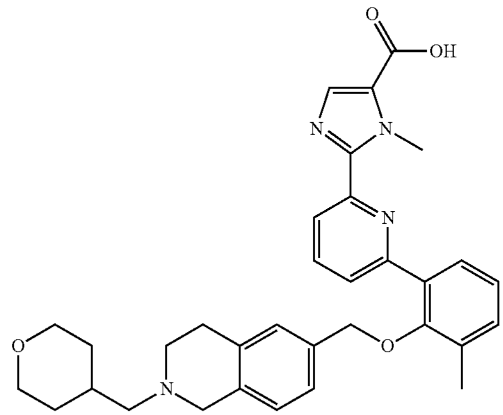 |
| 69 | 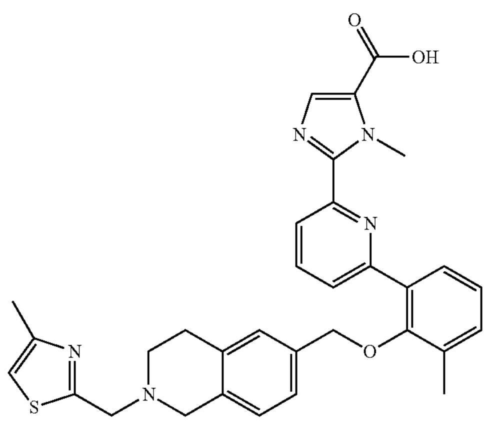 |
| 70 | 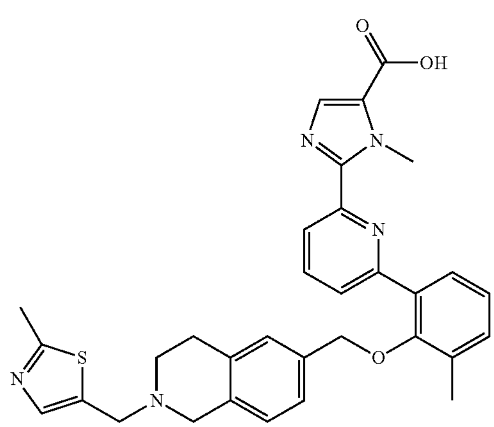 |
| 71 | |
| 72 | |
| 73 | |

TABLE 1-continued
| Cpd No. | Structure |
|---|---|
| 74 | 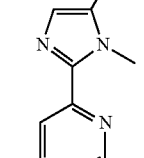 |
| 75 | 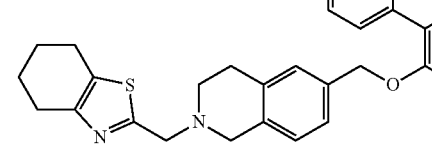 |
| 76 |  |
| 77 | 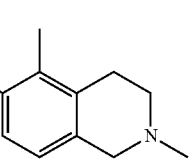 |
| 78 | 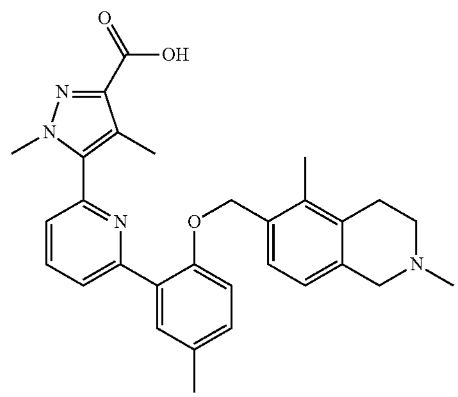 |
| 79 | 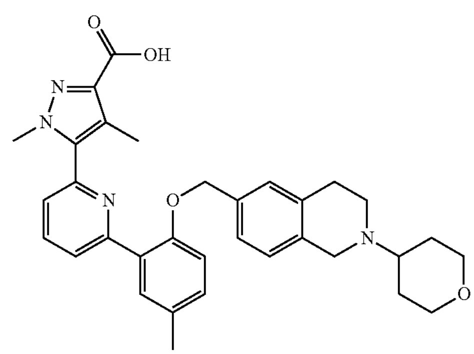 |
| 80 | 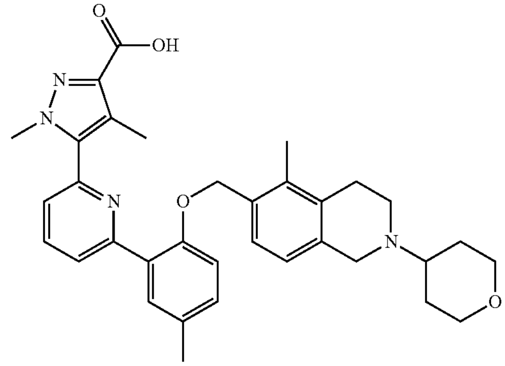 |

TABLE 1-continued

| Cpd No. | Structure |
|---|---|
| 81 | 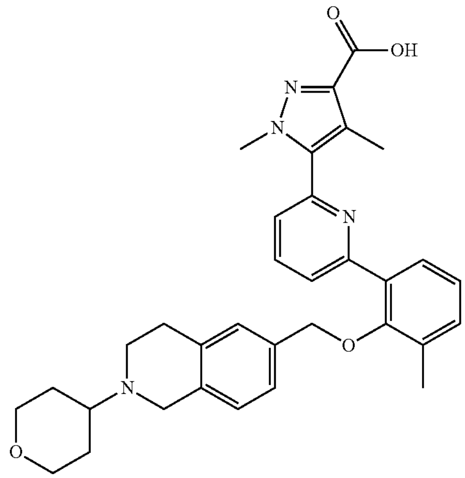 |
| 82 | 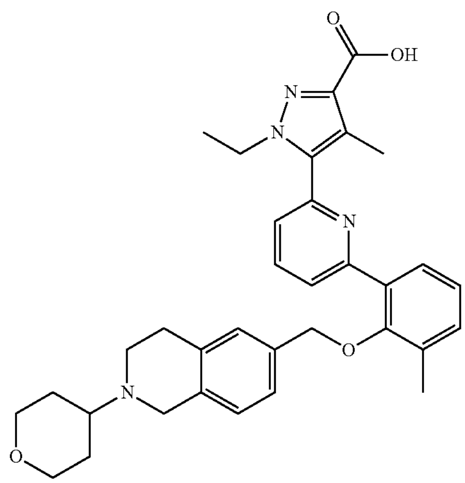 |
| 83 | 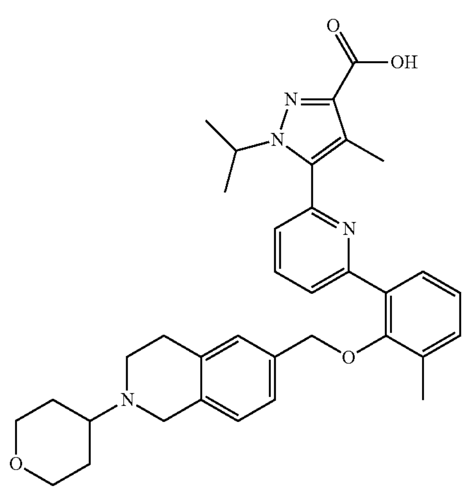 |
| 84 | |
| 85 | |
| 86 | |

TABLE 1-continued

| Cpd No. | Structure |
|---|---|
| 87 | 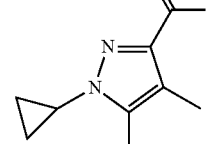 |
| 88 | 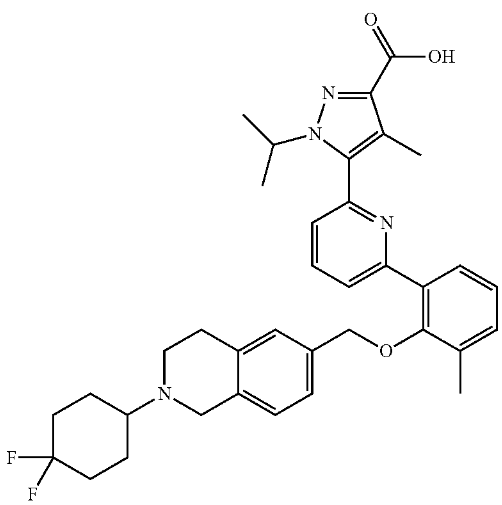 |
| 89 | 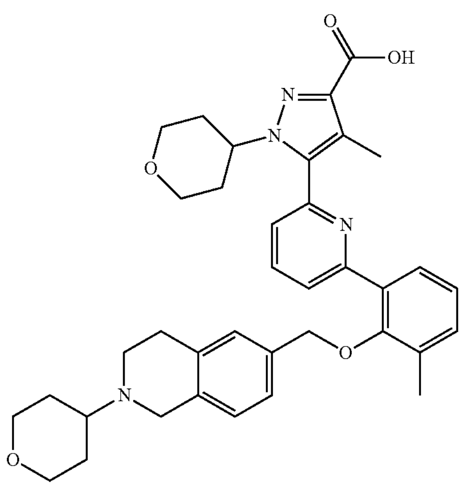 |
| 90 | 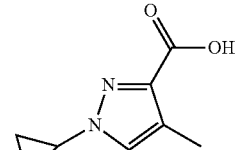 |
| 91 | |

In one embodiment, the invention relates to any of the compounds depicted in Table 1 above and the pharmaceutically acceptable salts thereof.

In another embodiment, the invention relates to the group consisting of compounds 1-10, 12-14, 16-35, 37, 38, 40-43, 46, 48 and 50-54 from Table 1 above and the pharmaceutically acceptable salts thereof.

In another embodiment, the invention relates to the group consisting of compounds 1-6,8,12, 14, 16-35, 37, 38, 48, 50, 51, 53-56, 60-65 and 67-91 from Table 1 above and the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes $-(CH_2)-$, $-(CH_2-CH_2)-$, $-(CH(CH_3))-$, $-(CH_2-CH_2-CH_2)-$, $-(C(CH_3)_2)-$, $-(CH(CH_2CH_3))-$, $-(CH(CH_3)-CH_2)-$, $-(CH_2-CH(CH_3))-$, $-(CH_2-CH_2-CH_2-CH_2)-$, $-(CH_2-CH_2-CH(CH_3))-$, $-(CH(CH_3)-CH_2-CH_2)-$, $-(CH_2-CH(CH_3)-CH_2)-$, $-(CH_2-C(CH_3)_2)-$, $-(C(CH_3)_2-CH_2)-$, $-(CH(CH_3)-CH(CH_3))-$, $-(CH_2-CH(CH_2CH_3))-$, $-(CH(CH_2CH_3)-CH_2)-$, $-(CH(CH_2CH_2CH_3))-$, $-(CHCH(CH_3)_2)-$ and $-C(CH_3)(CH_2CH_3)-$.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1λ⁶-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3] heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—C$_{1-6}$ alkyl radical, unless otherwise specified, this shall be understood to include —S(O)—C$_{1-6}$ alkyl and —S(O)$_2$—C$_{1-6}$ alkyl, likewise, —S—R$_a$ may be represented as phenyl-S(O)$_m$— when R$_a$ is phenyl and where m is 0, 1 or 2.

General Synthetic Methods

The compounds of the invention may be prepared by the general methods and examples presented below and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

The methods described below and in the Synthetic Examples section may be used to prepare the compounds of formula I.

Compounds of formula I may be prepared as described in Scheme 1

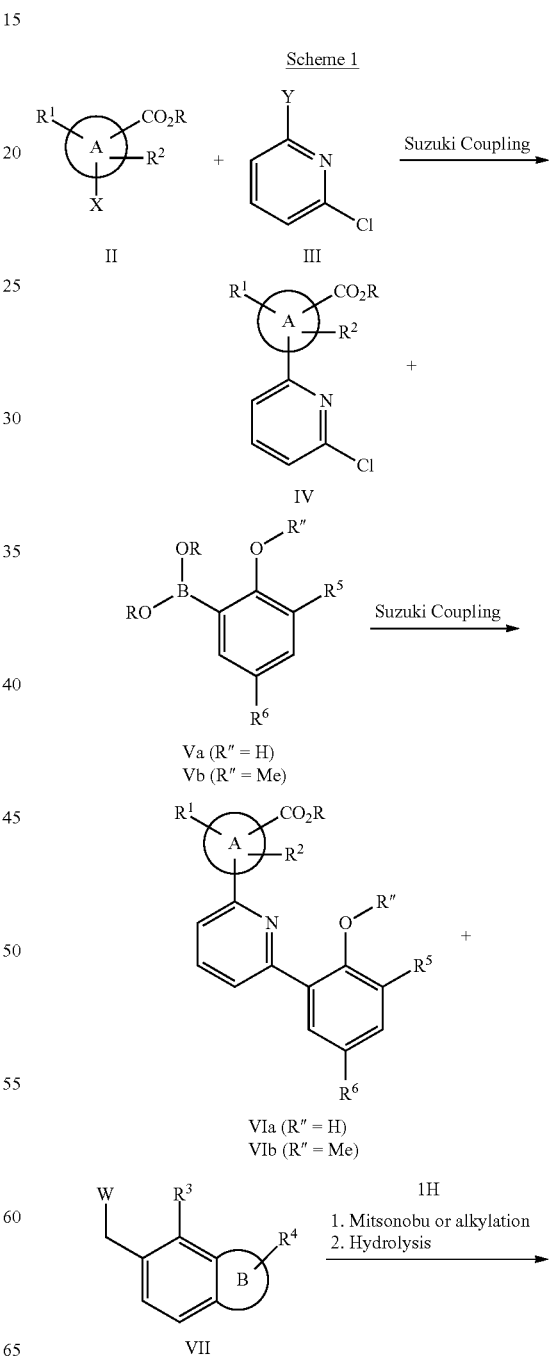

-continued

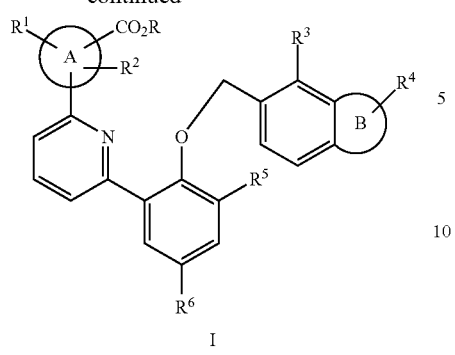

I

As illustrated above, ester II, where R is an alkyl group, such as Me or Et, and X is selected from either a halide such as Cl or Br or a triflate or pinacolboronate ester, is coupled with a pyridine derivative III, where Y is either iodo or a pinacolboronate ester, in the presence of a palladium catalyst such as tetrakis(triphenyl)phosphine (0) and a suitable base such as $Na_2CO_3$ in aqueous 1,2-DME (1,2-dimethoxyethane) under microwave irradiation at 120° C. Subsequent coupling of chloropyridine IV and boron species Va or Vb under identical conditions affords intermediate VIa or VIb. Deprotection of the Me (when R"=Me) ether of ester VIb with boron tribromide ($BBr_3$), followed by either alkylation of the phenol intermediate VIa with alkyl halide VII, where W=Cl or Br using a base such as cesium carbonate ($Cs_2CO_3$) in a solvent such as DMF at about 60° C., or Mitsonobu homologation in the presence of a phosphine such as tri-n-butyl phosphine ($PBu_3$) and an azodicarbonyl compound such as 1,1'-bis-azodicarbonyldipiperidine (ADDP) in an appropriate solvent such as PhMe at about 80° C., followed by hydrolysis with a suitable base such a LiOH in a solvent mixture such aqueous MeOH in THF at about 50° C. affords the desired compounds of formula I.

Compounds of formula I having

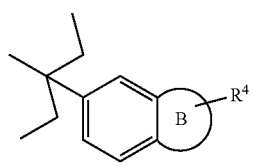

equal to

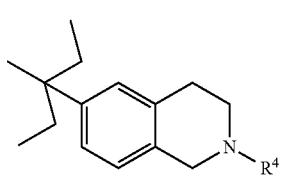

may be prepared according to Scheme 2.

Scheme 2

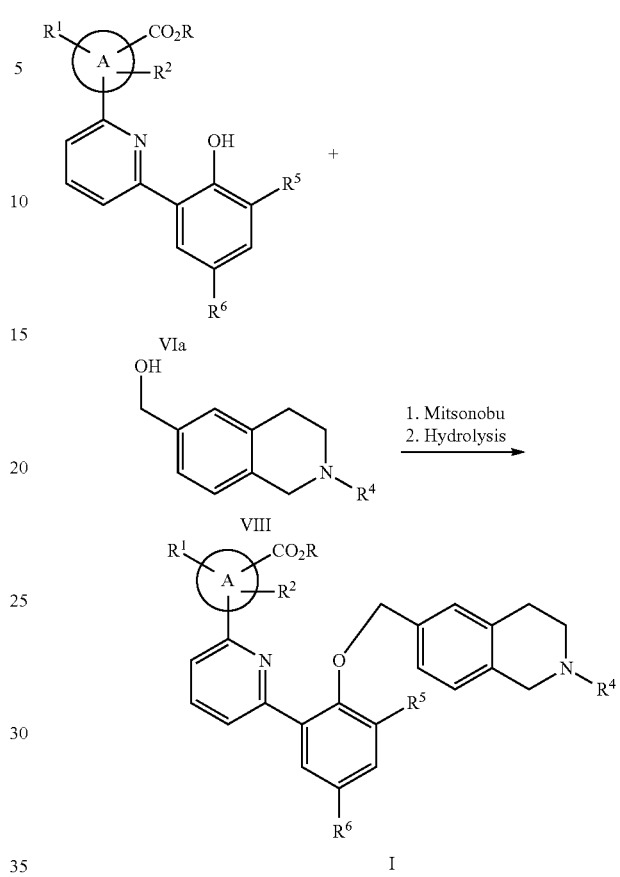

As illustrated above, phenol VIa is reacted under Mitsonobu conditions in the presence of a phosphine such as tri-n-butyl phosphine ($PBu_3$) and an azodicarbonyl compound such as 1,1'-bis-azodicarbonyldipiperidine (ADDP) with alcohol VIII in an appropriate solvent such as PhMe at about 80° C., followed by hydrolysis with a suitable base such a LiOH in a solvent mixture such as aqueous MeOH in THF at about 50° C. to afford the desired compound of formula I.

Alternatively, compounds of formula I having

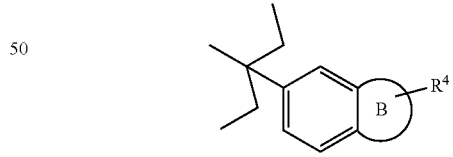

equal to

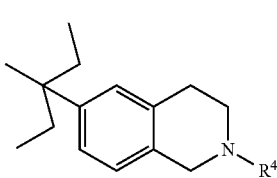

may be prepared as illustrated in Scheme 3.

Scheme 3

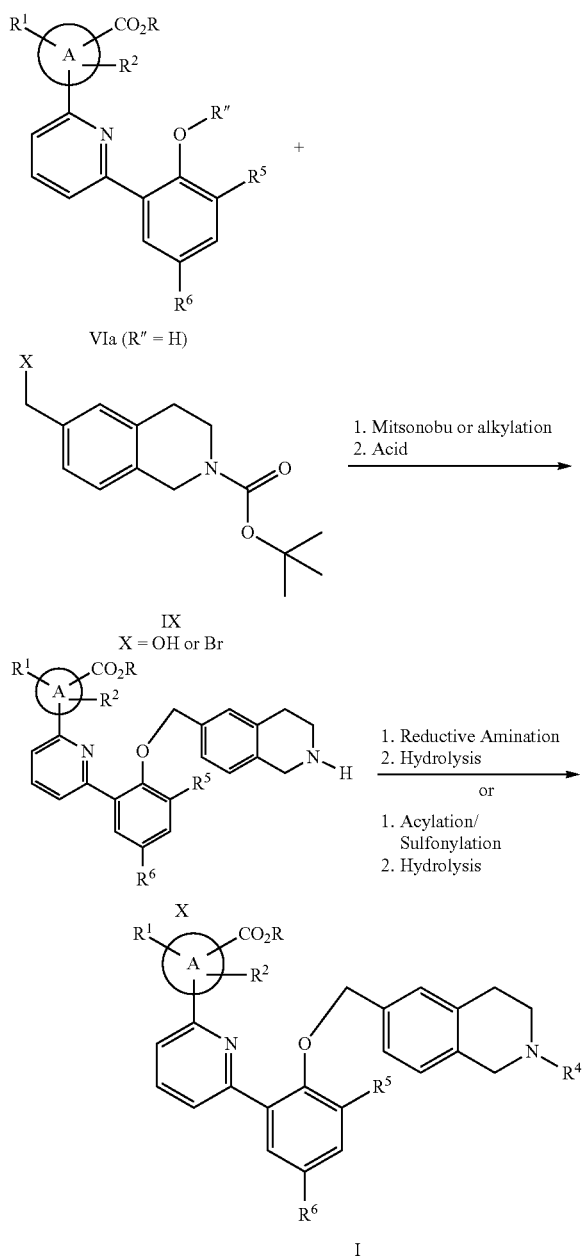

As illustrated above, phenol VIa is coupled with alcohol IX (X=OH) under Mitsunobu conditions in the presence of a phosphine such as tri-n-butyl phosphine (PBu$_3$) and an azodicarbonyl compound such as 1,1'-bis-azodicarbonyldipiperidine (ADDP) in an appropriate solvent such as PhMe at about 80° C. Subsequent deprotection of the t-Boc group with a suitable acid such as trifluoroacetic acid (TFA) provides tetrahydroisoquinoline X. Alternatively, intermediate X is prepared by alkylation of phenol intermediate VIa with alkyl halide IX (X=Br) using a base such as cesium carbonate (Cs$_2$CO$_3$) in a solvent such as DMF at about 60° C., followed by deprotection of the t-Boc group as above. Reductive amination of amine X with the desired ketone or aldehyde using an appropriate hydride source such as NaBH$_3$CN in a solvent such as MeOH containing an organic acid such as AcOH at about 50° C., followed by in situ hydrolysis with a base such as aqueous LiOH affords the desired compound of formula I. Alternatively, ayclation or sulfonylation of amine X with acyl or sulfonyl chlorides in the presence of a suitable base such as pyridine in a solvent such as DCM (dichloromethane) followed by hydrolysis of the ester delivers the desired compound of formula I.

All of the compounds in Table I are prepared by the methods illustrated above and in the Synthetic Examples section below.

UPLC/MS Methods

Retention times (RT) reported for compounds in the Synthetic Examples section are obtained by UPLC/MS using one of the following methods:

For each of the methods, the following are identical:

UPLC/MS system components—Acquity UPLC with PDA, SQ and ELS detectors.

PDA conditions—Detection: 210 to 400 nm. Sampling rate: 20 pts/sec. Filter response: fast.

ELSD conditions—Gain: 1000. Sampling rate: 20 pts/sec. Drift tube temp: 55° C. Nebulizer mode: cooling. Gas pressure: 41 psi.

MS conditions—Instrument: Acquity SQD with ESCi source. Ionization mode: ESI+/−. Capillary voltage: 3.5 kV. Cone voltage: 5 V. Extractor: 1.3 V. Source temp: 150° C. Desolvation temp: 350° C. Desolvation gas: 800 L/hr. Cone gas: 50 L/hr.

Conditions specific to each method are as follows

Method A1

Column—Waters BEH C18, 2.1×50 mm, 1.7 um particle diameter.

Description and Gradient: Medium polar fast gradient method. ESI+/− ion mode 80-1000 Da.

Gradient: 90% A to 100% B in 1.19 minutes hold at 100% B to 1.70 minutes. Flow rate 0.8 mL/min. A=(95% Water 5% Acetonitrile 0.05% Formic Acid) B=(Acetonitrile 0.05% Formic Acid).

Sample Injection Volume: 1 uL

Method A2

Column—Waters BEH C18, 2.1×50 mm, 1.7 um particle diameter.

Description and Gradient: Medium polar long gradient method. ESI+/− ion mode 80-1000 Da.

Gradient: 90% A to 100% B in 4.45 minutes hold at 100% B to 4.58 minutes. Flow rate 0.8 mL/min. A=(95% Water 5% Acetonitrile 0.05% Formic Acid) B=(Acetonitrile 0.05% Formic Acid).

Sample Injection Volume: 2 uL

Method A1 is used for all of the compounds in Table 1 except for compounds 44 and 49 for which Method A2 is used.

SYNTHETIC EXAMPLES

Final compounds are designated by compound numbers corresponding to the compound numbers in Table 1. Intermediates are given hyphenated numbers corresponding to the figures and numbers shown in the scheme for each example.

Example 1

Preparation of intermediate 1-[6-(2-hydroxy-5-methylphenyl)pyridin-2-yl]-5-trifluoromethyl-1H-pyrazole-4-carboxylic acid ethyl ester (1-7)

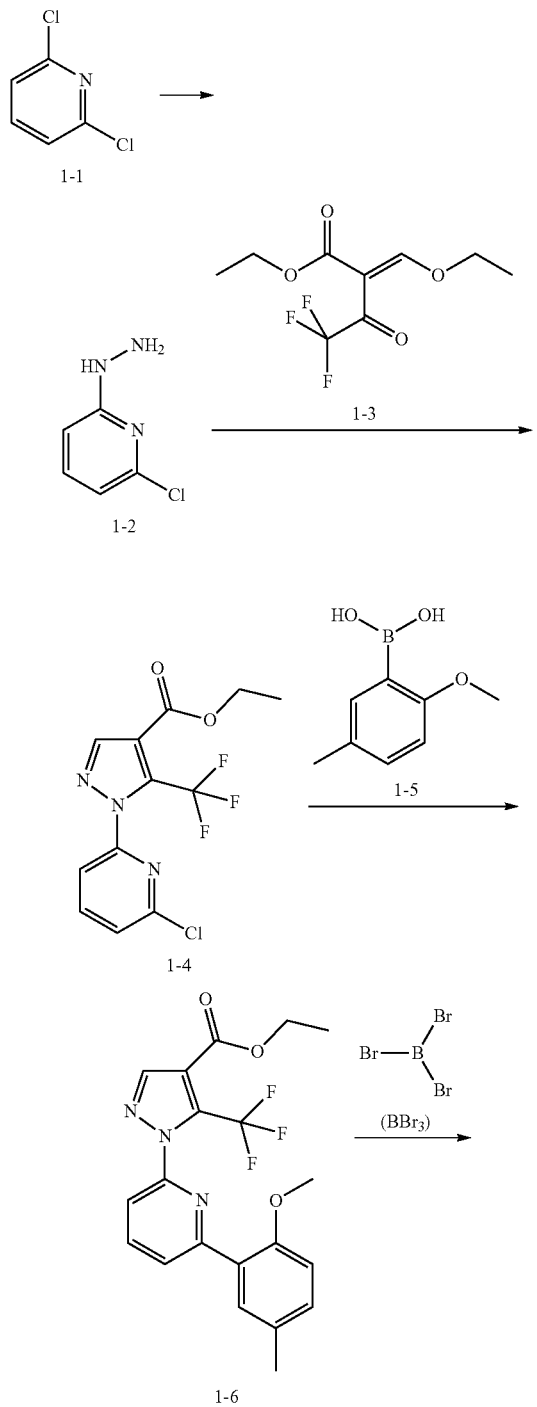

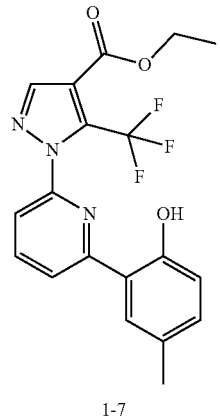

1-7

Hydrazine hydrate (15 mL) is added in one portion to 2,6-dichloropyridine 1-1 (5.0 g, 33 mmol) at room temperature. The mixture is heated to about 108° C. for 4 h, then cooled to room temperature. The resulting solids are collected by vacuum filtration, then washed with ice-cold $H_2O$. The solids are dried overnight in a vacuum oven to afford intermediate 1-2 (3.9 g).

Intermediate 1-2 (3.10 g, 21.6 mmol) and triethylamine (3.1 mL) are combined in MeCN (90 mL) at room temperature, then compound 1-3 (4.30 mL, 22.2 mmol) is added. The mixture is stirred for 20 min at room temperature and then heated to 60° C. for 30 additional min. The reaction is cooled to room temperature, then concentrated in vacuo. The crude product is purified by column chromatography on silica gel (using a solvent gradient of 0-30% EtOAc:heptane) to provide intermediate 1-4 (4.73 g).

Compound 1-4 (3.40 g, 10.6 mmol) is combined with boronic acid 1-5 (3.50 g, 21.1 mmol), tetrakis(triphenylphoshphine)palladium ($Pd(PPh_3)_4$) (615 mg, 0.532 mmol), and aqueous sodium carbonate ($Na_2CO_3$) (2N, 21.0 mL, 42.0 mmol) in 1,2-DME. The mixture is heated to 80° C. for 15 h, then diluted with DCM and poured into brine. The layers are separated and the combined organic phases are dried over $MgSO_4$, filtered, and concentrated in vacuo. The crude product is purified by reverse phase column chromatography on C18 (using a solvent gradient of 45-95% MeCN/$H_2O$+0.1% TFA). The product fractions are neutralized with saturated sodium bicarbonate solution and brine. The organic phase is separated, then the aqueous phase is extracted with EtOAc. The combined organic phases are dried over $MgSO_4$, filtered and concentrated in vacuo to provide intermediate 1-6 (4.19 g).

Compound 1-6 (4.19 g, 10.34 mmol) is dissolved in DCM at 0° C., then treated via addition funnel with a solution of $BBr_3$ (1.0 M in DCM, 31.0 mL, 31 mmol) over 30 min. The mixture is further stirred at 0° C. for 20 min, then at room temperature for 3 h. The reaction is quenched by the addition of a saturated solution of aqueous sodium bicarbonate, then extracted with DCM. The combined organic phases are dried over $MgSO_4$, filtered, and concentrated in vacuo. The crude product is purified by column chromatography on silica gel (using a solvent gradient of 6-50% EtOAc/heptane) to provide the desired intermediate 1-7 (2.84 g).

Example 2

Preparation of 1-{6-[2-(benzo[1,2,3]thiadiazol-5-ylmethyoxy)-5-methylphenyl]pyridin-2-yl}-5-trifluoromethyl-1H-pyrazole-4-carboxylic acid (Compound 7, Table 1)

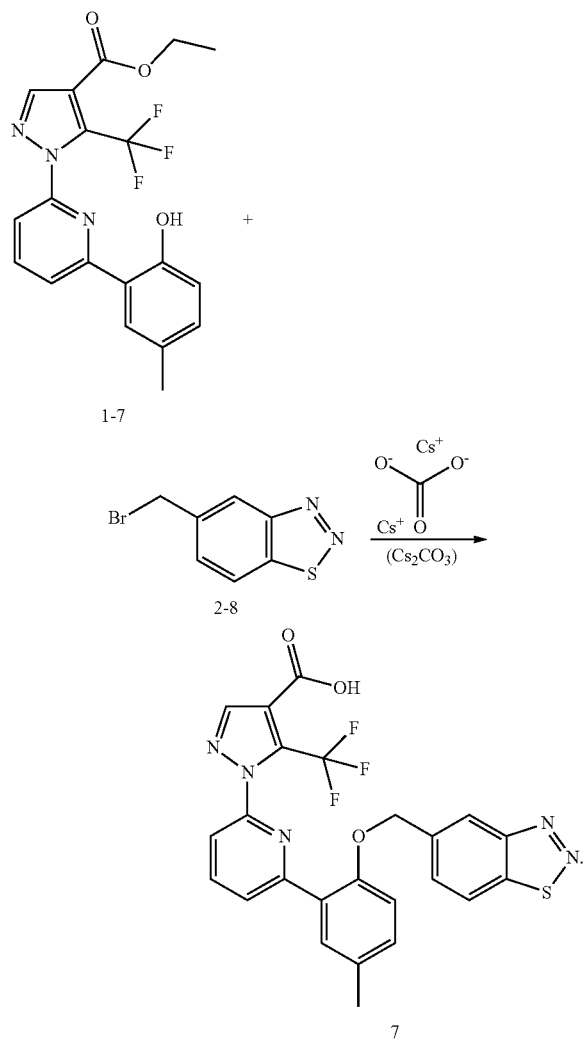

Intermediate 1-7 (50.0 mg, 0.128 mmol) and bromide 2-8 (32.0 mg, 0.140 mmol) are combined in DMF (2 mL), then treated with Cs$_2$CO$_3$ (50.0 mg, 0.153 mmol). The mixture is heated to 80° C. for 1.5 h, then cooled to room temperature and diluted with water (1 mL). The mixture is then treated with LiOH.H$_2$O (54 mg, 1.3 mmol), and stirred at 50° C. for 15 h. The resulting mixture is cooled to room temperature and acidified with 3 N HCl (1 mL), then extracted with DCM. The organic layers separated with a hydrophobic frit, then dried over Na$_2$SO$_4$. Concentration of the filtrate in vacuo affords the title compound (60 mg). MS, electrospray, m/z=512.3 [M+H], rt 1.13 min.

The following compound is prepared according to the procedure described in Example 2, using the appropriate starting materials and purification conditions:

Compound 10: MS, electrospray 509.2 [M+H], rt 1.01 min.

Example 3

Preparation of intermediate (1-methyl-1,2,3,4-tetrahydroquinolin-6-yl)methanol (3-12)

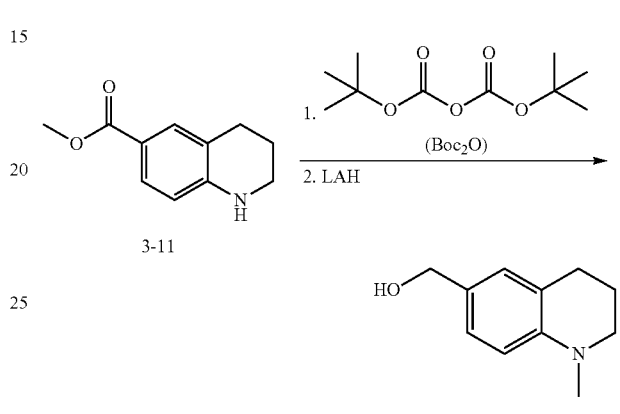

Ester 3-11 (920 mg, 4.81 mmol) and 4-dimethylaminopyridine (194 mg, 1.59 mmol) are combined in THF (20 mL), then treated in one portion with Boc$_2$O (1.1 g, 5.0 mmol). The mixture is stirred at room temperature for 3 d, then concentrated to half of the original volume. The remaining mixture is applied to a silica gel column and purified by gradient elution (20-60% EtOAc/heptane) to afford the intermediate carbamate as a solid. The solid is subsequently dissolved in THF (12 mL) at room temperature, then treated with solid lithium aluminum hydride (LAH) powder (240 mg, 6.32 mmol). The resulting slurry is heated to 65° C. for 13 h, then cooled to room temperature and diluted with water (5 mL), EtOAc (10 mL), and saturated aqueous sodium potassium tartrate solution (10 mL). The mixture is vigorously stirred for 2 h, then the layers are separated. The combined organics are dried over Na$_2$SO$_4$, filtered and concentrated in vacuo to afford crude 3-12 (479 mg).

Example 4

Preparation of intermediate (1-methyl-1,2,3,4-tetrahydroquinolin-7-yl)methanol (4-14)

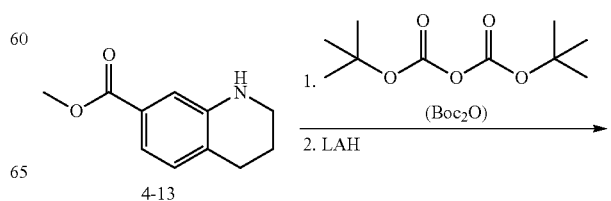

51

-continued

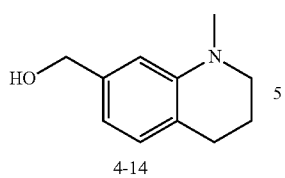
4-14

The intermediate 4-14 is prepared from ester 4-13 according to the procedure detailed in Example 3.

Example 5

Preparation of intermediate (1-methyl-1,2,3,4-tetrahydroisoquinolin-7-yl)methanol (5-16)

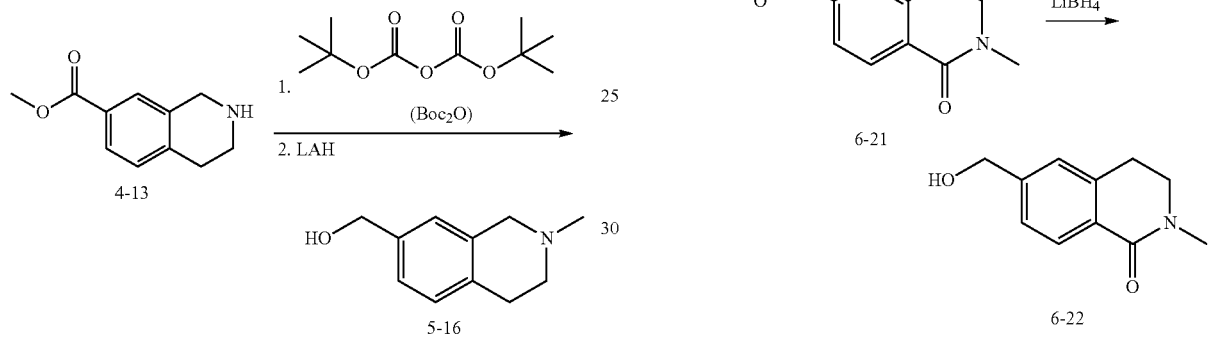

The intermediate 5-16 is prepared from ester 5-15 according to the procedure outlined in Example 3.

Example 6

Preparation of intermediate 6-hydroxymethyl-2-methyl-3,4-dihydro-2H-isoquinolin-1-one (6-22)

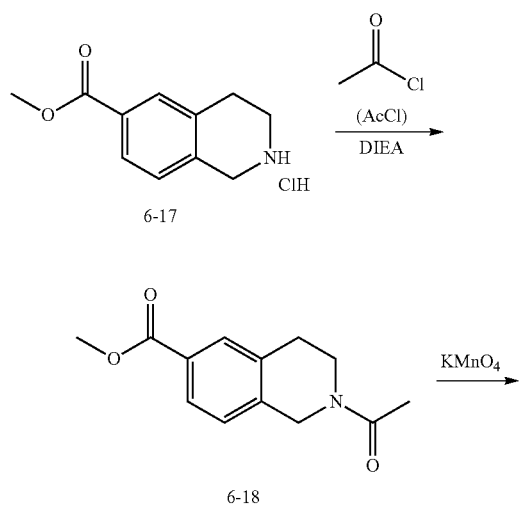

52

-continued

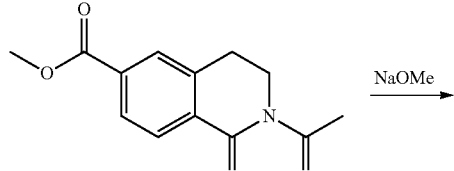
6-19

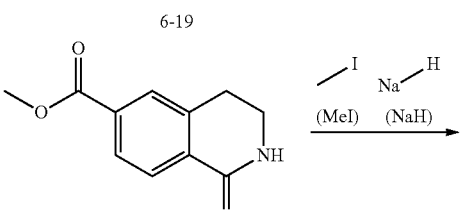
6-20

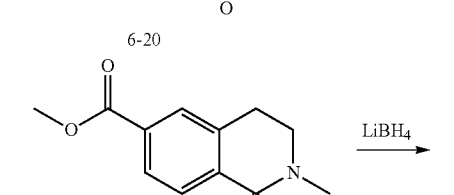
6-21

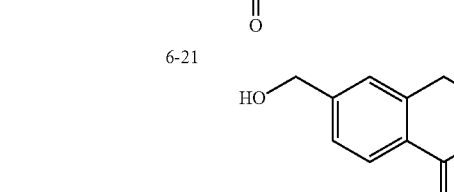
6-22

Ester 6-17 (250 mg, 1.10 mmol) is combined with N,N-diisopropylethylamine (DIEA) (421 µL, 2.41 mmol) in DCM (10.0 mL) at room temperature, then treated with acetyl chloride (AcCl) (85.9 µL, 1.21 mmol). The resulting mixture is stirred for 1 h, then partitioned between $H_2O$ and EtOAc and the phases are separated. The organic phase is washed with 1N HCl, saturated aqueous $NaHCO_3$, and brine, then dried over $Na_2SO_4$, filtered, and concentrated to afford 6-18 (258 mg).

Compound 6-18 (200 mg, 0.857 mmol) is combined with 18-crown-6 (15 mg), and potassium permanganate ($KMnO_4$) (271 mg, 1.72 mmol) in DCM (3 mL) at room temperature. The resulting mixture is stirred for 2 h, then diluted with 1N HCl (60 mL) and additional DCM (50 mL). The phases are separated and the aqueous phase is extracted twice with DCM. The combined organic phases are washed with brine, dried over $Na_2SO_4$, filtered, and concentrated to afford 6-19 (202 mg).

Compound 6-19 (180 mg, 0.728 mmol) is dissolved in MeOH (9.0 mL) at room temperature, then treated with sodium methoxide (NaOMe) (25 wt % in MeOH, 332 µL, 1.46 mmol) and stirred for 1 h. The resulting mixture is partitioned between 1N HCl and EtOAc and the phases are separated. The organic phase is washed with brine, dried over $Na_2SO_4$, filtered, and concentrated to afford 6-20 (118 mg).

Compound 6-20 (118 mg, 0.575 mmol) is dissolved in a mixture of THF (5.0 mL) and DMF (1.0 mL), then cooled to 0° C. A dispersion of sodium hydride (NaH) (60 wt % in mineral oil, (29.9 mg, 0.748 mmol) is added and the mixture is stirred for 15 min. Iodomethane (MeI) is then added and the reaction is warmed to room temperature and stirred for 2 h.

The mixture is then treated with 1N HCl (1.0 mL) and diluted with saturated aqueous NaHCO₃. The resulting mixture is extracted twice with EtOAc and the combined organic phases are washed with brine, dried over Na₂SO₄, filtered, and concentrated. The crude residue is purified by reverse phase column chromatography on C18 (using a solvent gradient of 5-70% MeCN:H₂O+0.1% TFA) to provide compound 6-21 (78 mg).

Compound 6-21 (75.0 mg, 0.342 mmol) is dissolved in THF (4.0 mL) at room temperature, then treated with lithium borohydride (LiBH₄) (2M in THF, 1.00 mL, 2.00 mmol) and stirred overnight. The resulting mixture is quenched with 1N HCl (10 mL) and diluted with water and EtOAc. The mixture is extracted with EtOAc and the combined organic phases are washed with brine, dried over Na₂SO₄, filtered, and concentrated to afford 6-22 (58 mg).

Example 7

Preparation of intermediate (1-methanesulfonyl-2,3-dihydro-1H-indol-5-yl)methanol (7-24)

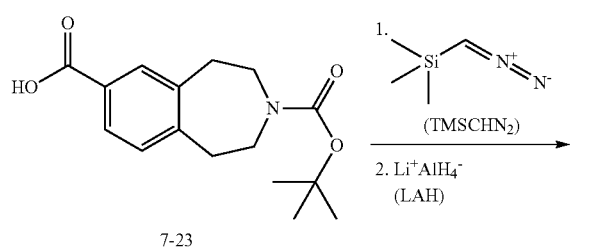

Acid 7-23 (500 mg, 1.71 mmol) is dissolved at room temperature in a 1:1 mix of PhMe and MeOH (10 mL). A solution of trimethylsilyldiazomethane (TMSCHN₂) (1.5 mL, 2M in hexanes, 3.0 mmol) is added via syringe and the mixture is stirred for 1 h. Glacial AcOH is added until gas evolution is no longer observed, and then the mixture is stirred for 2 h. The solvent is then removed in vacuo, and the residue is azeotroped with PhMe (3×10 mL) to remove residual AcOH. The remaining oil is redissolved in THF (10 mL) under Ar at room temperature, then treated with solid LAH powder (320 mg, 8.43 mmol). The resulting slurry is heated to reflux (70° C.) for 2 h, then cooled to room temperature and stirred for 14 h. The mixture is quenched with water (0.16 mL), then stirred 5 min before the addition of 1N NaOH (0.36 mL). After 5 min, additional water (0.48 mL) is added and the mixture is stirred for a further 20 min before 1 g of Na₂SO₄ is added. The mixture is filtered through a frit, and the solids are rinsed with EtOAc. The solids are slurried in acetone and vigorously stirred for 1 h, then refiltered. The filtrate is combined with the previous organic filtrate, then concentrated in vacuo to afford the desired intermediate 7-22 (446 mg).

Example 8

Preparation of intermediate (1-methanesulfonyl-2,3-dihydro-1H-indol-5-yl)methanol (8-26)

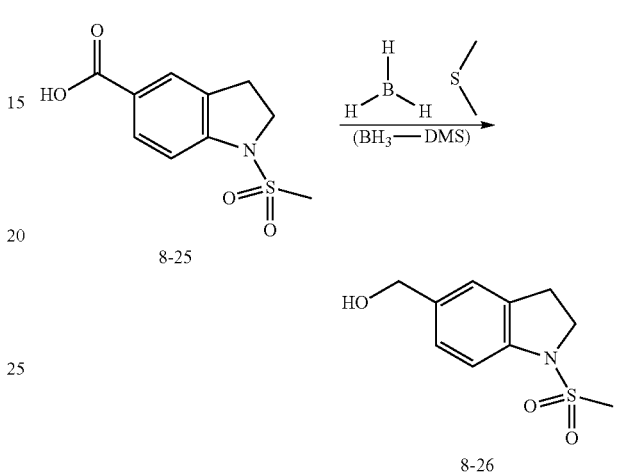

Acid 8-25 (300 mg, 1.24 mmol) is dissolved in dry THF (8 mL) at room temperature under Ar, then treated via syringe with borane dimethylsulfide (BH₃-DMS) (0.26 mL, 2.7 mmol). The mixture is stirred 14 h, then heated to 70° C. for 3 h. The mixture is cooled to room temperature, then quenched with MeOH (2 mL) and concentrated in vacuo to afford the desired intermediate 8-26 (289 mg) that is used without further purification.

Example 9

Preparation of 1-{6-[2-(1-methanesulfonyl-2,3-dihydro-1H-indol-5-ylmethyoxy)-5-methylphenyl]pyridin-2-yl}-5-trifluoromethyl-1H-pyrazole-4-carboxylic acid (Compound 9, Table 1)

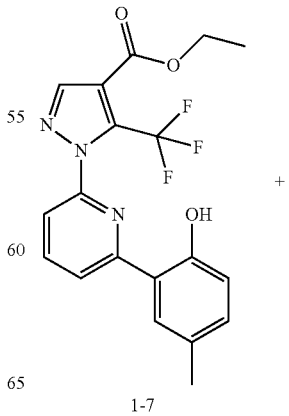

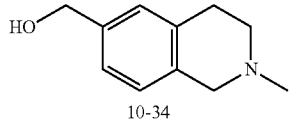

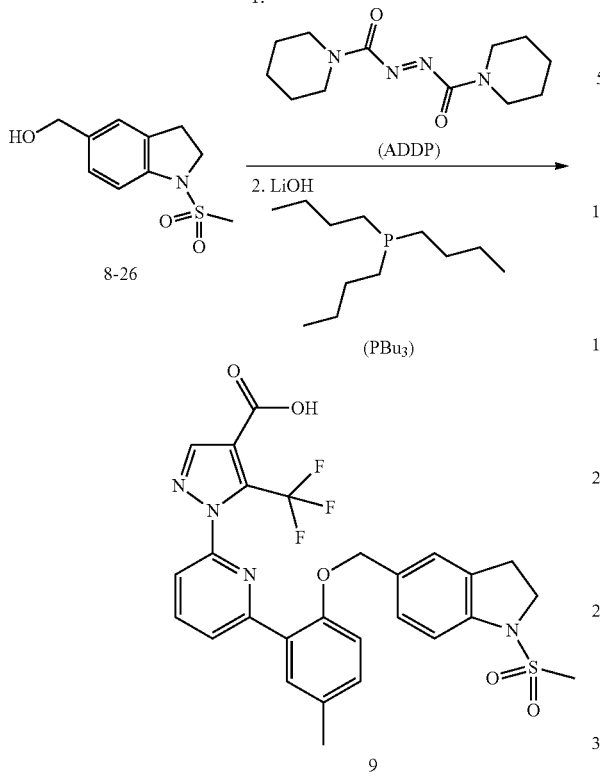

Intermediate 1-7 (50.0 mg, 0.128 mmol) (Example 1) and alcohol 8-26 (57.0 mg, 0.251 mmol) are combined with ADDP (65.0 mg, 0.258 mmol) in PhMe (3 mL), then treated with PBu₃ (65.0 µL, 0.257 mmol). The mixture is heated to 80° C. for 15 h, then applied hot to a silica gel column. Elution (using a solvent gradient of 5-50% EtOAc:heptane) delivers the intermediate ester. This product is resuspended in a mixture of THF (2 mL) and H₂O (1 mL), then treated with lithium hydroxide monohydrate (LiOH.H₂O) (54 mg, 1.3 mmol). The mixture is heated to 55° C. for 12 h, then cooled to room temperature, and quenched with 3N HCl (1 mL). Extraction of the mixture with DCM, then evaporation of the organic solvent affords a crude solid. This is triturated with hot MeOH, then filtered. The collected solid is dried in vacuo to afford the title compound 9 (60 mg). MS, electrospray, m/z=571.3 [M−H], rt 1.07 min.

Example 10

Preparation of intermediate (2-methyl-1,2,3,4-tetrahydroisoquinolin-6-yl)methanol (10-34)

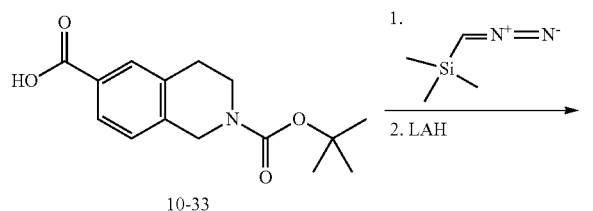

A solution of TMSCHN₂ (2 M in hexanes, 36.0 mL, 72.0 mmol) is added to a stirred room temperature solution of acid 10-33 (9.99 g, 36.02 mmol) in a 1:1 mixture of PhMe/MeOH (134 mL). After 1.5 h, the mixture is quenched with glacial AcOH (10 mL) and stirred for an additional 5 min. The solvents are removed in vacuo to provide the crude ester as a solid upon standing. The intermediate ester (15.2 g, 52.1 mmol) is dissolved in THF (200 mL) and treated with LAH powder (4.95 g, 130 mmol). The resulting slurry is heated to 65° C. for 3 h, then cooled to room temperature and slowly quenched with water (3.6 mL). The mixture is then treated with 2 N NaOH (3.6 mL), followed by additional water (10.8 mL). The resulting slurry is stirred for 1 h, then filtered to remove solids. The filtrate is dried over Na₂SO₄, filtered again, and concentrated in vacuo to provide the desired product. The solids initially collected by filtration are resuspended in acetone and vigorously stirred overnight at room temperature. The slurry is refiltered, and the remaining acetone is combined with the initially collected product. Concentration of the combined organic filtrates provides the desired intermediate 10-34 (7.50 g).

Example 11

Preparation of intermediate (2,5-dimethyl-1,2,3,4-tetrahydroisoquinolin-6-yl)methanol (11-45)

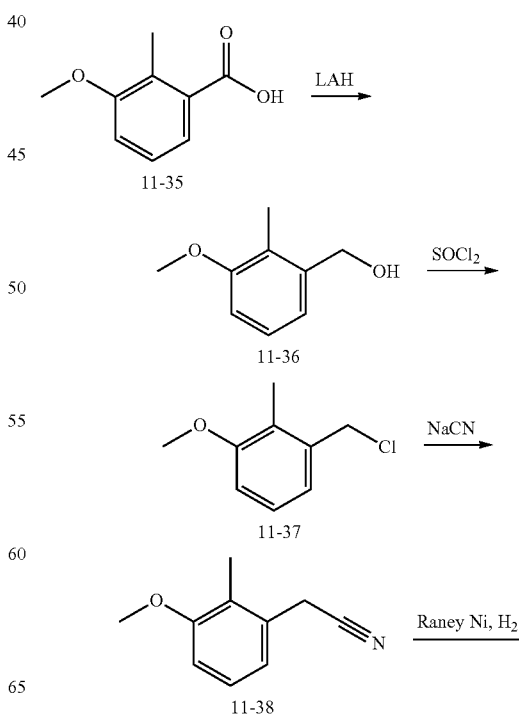

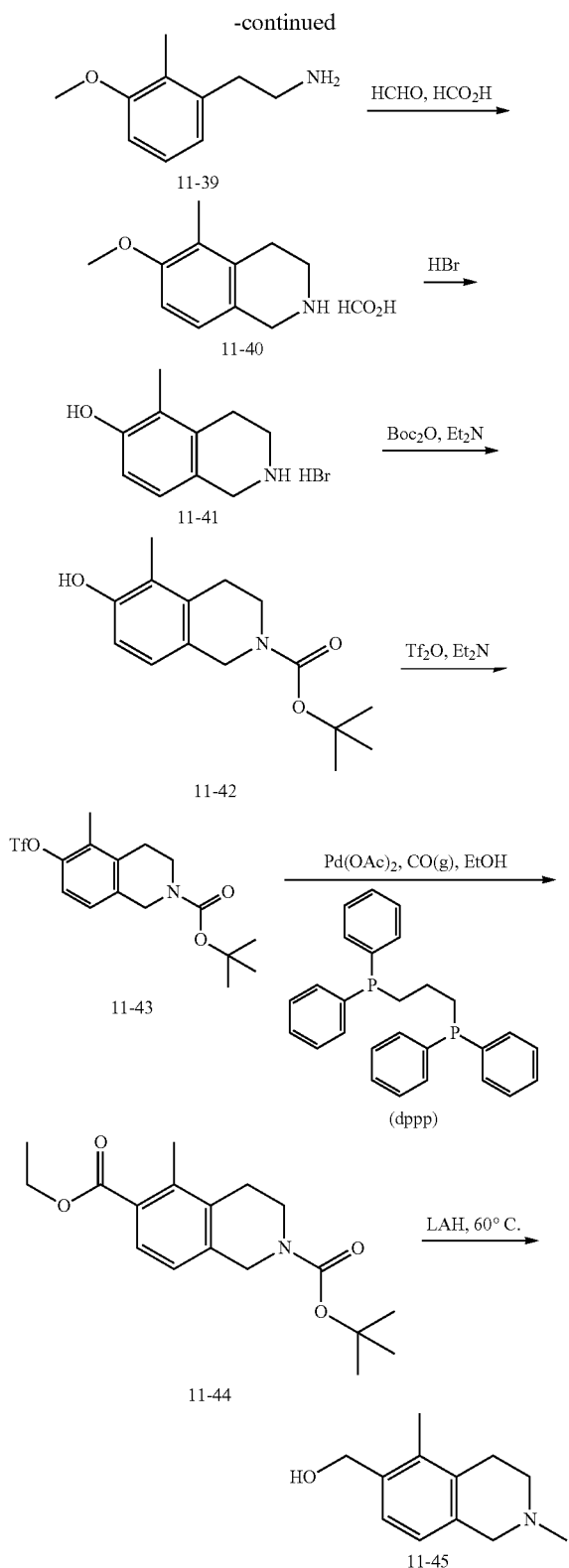

A solution of acid 11-35 (350 g, 2.10 mol) in THF (1.4 L) is added to a slurry of LAH (95.9 g, 1.40 mol) in THF (2.5 L) at 0° C. The mixture is stirred at room temperature for 0.5 h, then heated to reflux for 1 h. The mixture is then cooled to 0° C., and slowly quenched by the addition of saturated aqueous ammonium chloride solution. A large excess of solid $Na_2SO_4$ and EtOAc are added, then the solids are collected by filtration. The filtrate is concentrated in vacuo to afford crude 11-36 (350 g) which is used directly in the next step.

To a solution of compound 11-36 (294 g, 1.90 mol) in DCM (2.2 L) at −10° C. is added thionyl chloride ($SOCl_2$) (460 g, 3.90 mol). Then the reaction mixture is heated to reflux for 1 h, followed by concentration in vacuo to provide crude 11-37 (298 g) which is used directly in the next step.

A mixture of compound 11-37 (298 g, 1.8 mol) and NaCN (154.5 g, 2.1 mol) in DMF (1.2 L) is stirred at room temperature overnight, then extracted with EtOAc and $H_2O$. The organic layer is dried over $Na_2SO_4$, filtered, and concentrated in vacuo. The residue is purified by column chromatography on silica gel (petroleum ether:EtOAc=50:1) to deliver intermediate 11-38 (230 g).

A mixture of compound 11-38 (180 g, 1.10 mol), Raney Ni (40 g) and aqueous ammonia (250 mL) in MeOH (1.0 L) is stirred under $H_2$ (50 psi) at room temperature for 5 h. The mixture is then filtered and concentrated to give compound 11-39 (165 g) that is used directly in the next step.

A solution of compound 11-39 (165 g, 1.0 mol) and aqueous formaldehyde (HCHO) (37 wt %, 30 g, 1.0 mol) in formic acid ($HCO_2H$) (1.5 L) is stirred at 50° C. overnight, then the solvent is removed in vacuo to afford compound 11-40 (150 g) which is used directly in the next step.

Compound 11-40 (150 g, 847 mmol) is suspended in aqueous HBr (48%, 1.0 L), then heated to 100° C. overnight. Removal of the solvent in vacuo provides compound 11-41 (195 g) which is used directly in the next step.

To a solution of compound 11-41 (195 g, 799 mmol) in THF (1.0 L) and $H_2O$ (1.0 L) is added $Et_3N$ (242 g, 2.4 mol) and $Boc_2O$ (174 g, 799 mmol). The resulting mixture is stirred at room temperature overnight, then extracted with EtOAc. The combined organic phases are washed with brine, dried over $Na_2SO_4$, filtered and concentrated in vacuo. The crude product is purified by column chromatography on silica gel (using 10:1 petroleum ether:EtOAc) to provide compound 11-42 (100 g).

To a solution of compound 11-42 (100 g, 380 mmol) and $Et_3N$ (76.8 g, 760 mmol) in DCM (1.5 L) cooled to 0° C. is added triflic anhydride ($Tf_2O$) (107 g, 380 mmol) via addition funnel. Upon complete addition of $Tf_2O$, the solution is warmed to room temperature for 5 h. The reaction mixture is then treated with $H_2O$ and DCM, and the organic phase is separated, washed with brine, dried over $Na_2SO_4$, filtered, and concentrated in vacuo. The residue is purified by column chromatography on silica gel (using 20:1 petroleum ether:EtOAc) to provide compound 11-43 (105 g).

Compound 11-43 (50.0 g, 127 mmol) is combined with palladium (II) acetate ($Pd(OAc)_2$) (5.0 g), dppp (5.0 g) and $Et_3N$ (25.7 g, 254 mmol) in EtOH (1.0 L), then stirred at 80° C. overnight under CO at a pressure of 4 MPa. The mixture is cooled to room temperature, then the solids are removed by filtration. The filtrate is concentrated in vacuo, and the remaining residue is purified by column chromatography on silica gel (using 20:1 petroleum ether:EtOAc) to provide compound 11-44 (25.0 g).

To a solution of LAH (8.90 g, 235 mmol) in THF (300 mL) at 0° C. is added dropwise a solution of compound 11-44 (25.0 g, 78.4 mmol) in THF (300 mL) over 30 min. After addition, the reaction mixture is stirred at 60° C. for 3 h, then cooled to room temperature and treated with $H_2O$ and DCM. The organic phase is separated, washed with brine, dried over $Na_2SO_4$, filtered, and concentrated in vacuo. The crude prod-

Example 12

1-{6-[5-methyl-2-(2-methyl-1,2,3,4-tetrahydroiso-quinolin-6-ylmethoxy)phenyl]pyridin-2-yl}-5-trifluoromethyl-1H-pyrazole-4-carboxylic acid (Compound 2, Table 1)

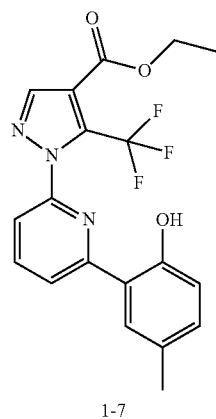

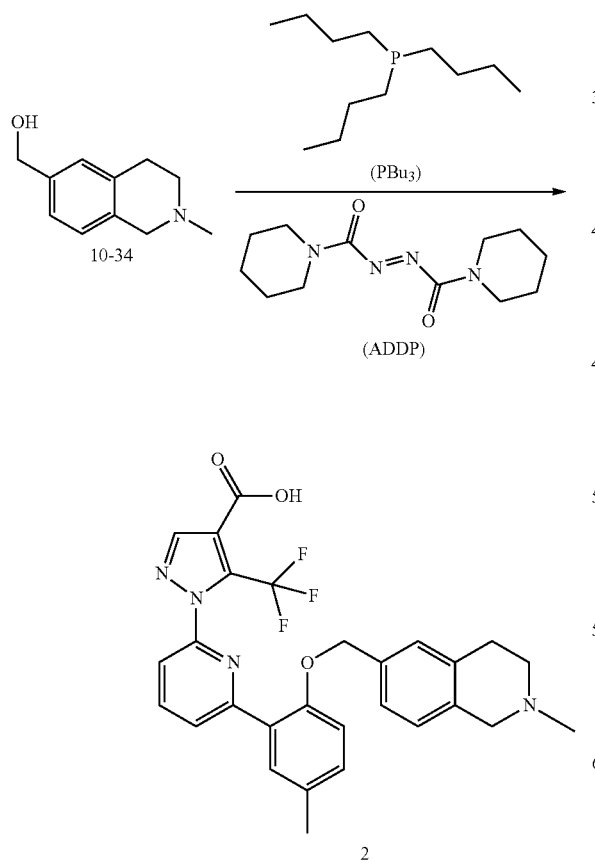

PBu₃ (166 µL, 0.66 mmol) is added to a mixture of intermediate 1-7 (64 mg, 0.16 mmol) (Example 1), compound 10-34 (116 mg, 0.66 mmol), and ADDP (166 mg, 0.66 mmol) in PhMe (3 mL). The mixture is then heated to 80° C. for 15 h. The hot mixture is then applied directly to a silica gel column and purified using a solvent gradient of 5-60% EtOAc:heptane. The product is isolated and redissolved in a mixture of THF (3 mL) and H₂O (1 mL), then treated with lithium hydroxide monohydrate (69 mg, 1.6 mmol). The mixture is heated to 50° C. for 12 h, then concentrated in vacuo. The crude salt is acidified with a solution of MeCN/H₂O (2:1) containing 0.1% TFA (1 mL), then purified by reverse phase column chromatography on C18 (using a solvent gradient of 5-60% MeCN/H₂O+0.1% TFA) to afford the title compound 2 (72 mg). MS, electrospray, m/z=521.2 [M−H], rt=0.70 min.

The following compounds from Table 1 are prepared according to the procedure described in Example 12, using the appropriate starting materials and purification conditions Compound 11: MS, electrospray, m/z=523.2 [M+H], rt 1.13 min.

Compound 13: MS, electrospray, m/z=523.2 [M+H], rt 1.26 min.

Compound 52: MS, electrospray, m/z=523.2 [M+H], rt 80 min.

Compound 8: MS, electrospray, m/z=537.3 [M+H], rt 1.00 min.

Compound 38: MS, electrospray, m/z=537.4 [M+H], rt 0.76 min.

Compound 40: MS, electrospray, m/z=537.3 [M+H], rt 0.76 min.

Example 13

Preparation of intermediate 4-methyl-2-(4,4,5,5-tetramethyl-[1,3,2]dioxaborolan-2-yl)-phenol (13-49)

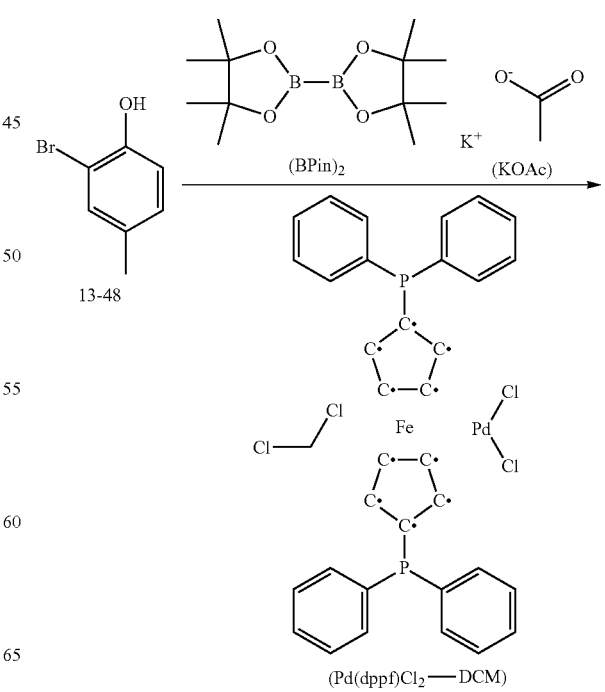

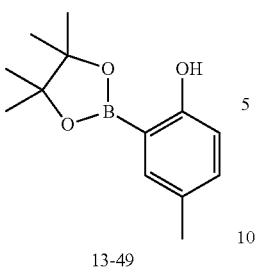

13-49

Phenol 13-48 (13.0 g, 69.5 mmol) is combined with (Bpin)₂ (19.5 g, 76.9 mmol), KOAc (20.6 g, 210 mmol), and 1,1'-bis(diphenylphosphino)ferrocene palladium (II) chloride [Pd(dppf)Cl₂] (5.5 g, 6.7 mmol) in 1,2-DME (250 mL) at room temperature. The mixture is heated to 80° C. for 16 h, then cooled to room temperature and directly applied to a silica gel column. Purification by column chromatography (using a solvent gradient of 0-10% EtOAc:heptanes) provides the desired intermediate 13-49 (8.7 g).

Example 14

Preparation of 3-methyl-4-{6-[5-methyl-2-(2-methyl1,2,3,4-tetrahydroisoquinolin-6-ylmethoxy)phenyl]pyridin-2-yl}thiophene-2-carboxylic acid (Compound 46, Table 1)

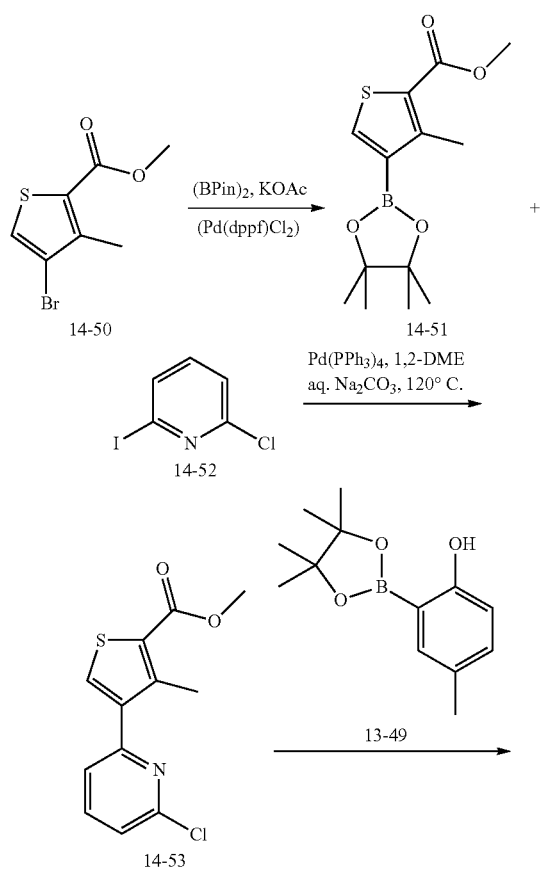

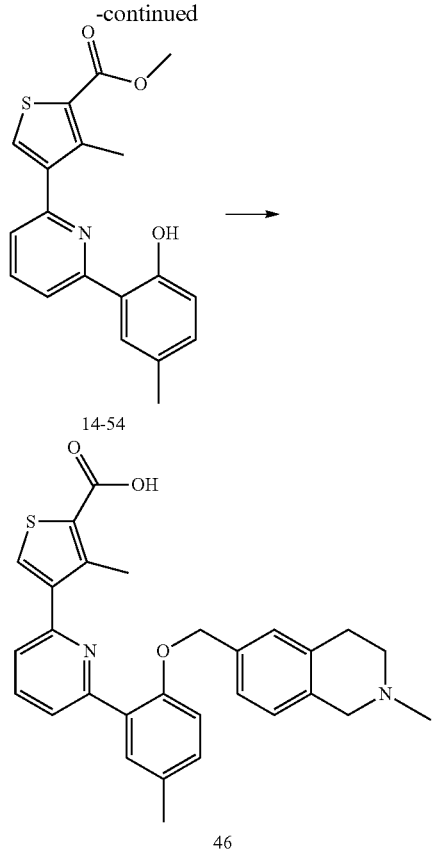

Ester 14-50 (12.0 g, 51.0 mmol) is combined in 1,2 DME (400 mL) with KOAc (14.2 g, 145 mmol), (Bpin)₂ (24.0 g, 96.3 mmol) and [Pd(dppf)Cl₂-DCM] (3.68 g, 4.53 mmol), then irradiated at 130° C. for 30 min. The mixture is cooled to room temperature, and purified by column chromatography on silica gel (using a solvent gradient of 5-75% EtOAc/heptane) to deliver intermediate 14-51 (14.0 g).

Intermediate 14-51 (3.00 g, 10.6 mmol) is dissolved in a mixture of aqueous Na₂CO₃ (13.2 mL, 2.0 M, 26.4 mmol) and 1,2-DME (90 mL), then treated with pyridine derivative 14-52 (2.67 g, 11.2 mmol), and Pd(PPh₃)₄ (0.60 g, 0.52 mmol). The mixture is irradiated at 120° C. for 40 min, then concentrated to dryness under N₂. The remaining residue is purified by column chromatography on silica gel (using a solvent gradient of 5-50% EtOAc/heptane) to afford intermediate 14-53 (1.52 g).

Intermediate 14-53 (2.10 g, 7.84 mmol) is combined with phenol 13-49 (2.02 g, 8.63 mmol) (Example 13), aqueous Na₂CO₃ (12.0 mL, 2.0 M, 24.0 mmol), and Pd(PPh₃)₄ (0.44 g, 0.38 mmol) in 1,2-DME (48 mL), then irradiated at 120° C. for 40 min. The mixture is diluted with excess DCM and a small amount of water to dissolve salts, then the layers are separated using a hydrophobic frit. The organic filtrate is concentrated in vacuo, then purified by column chromatography on silica gel (using a solvent gradient of 5-50% EtOAc/heptane) to afford intermediate 14-54 (2.62 g).

The following compounds from Table 1 are prepared from intermediate 54 according to the procedure described in Example 12.

Compound 46: MS, electrospray, m/z=483.3 [M−H], rt 0.71 min.

Compound 47: MS, electrospray, m/z=497.2 [M−H], rt 0.87 min.

Example 15

Preparation of 6'-[5-methyl-2-(2-methyl-1,2,3,4-tetrahydroisoquinolin-6-ylmethoxy)phenyl]-3,4,5,6-tetrahydro-2H-[1,2']bipyridinyl-4-carboxylic acid (Compound 45, Table 1)

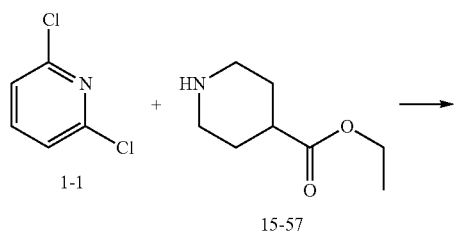

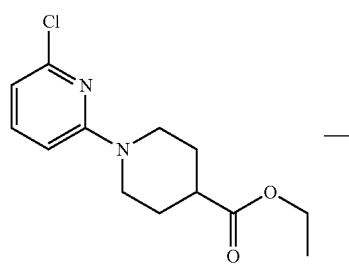

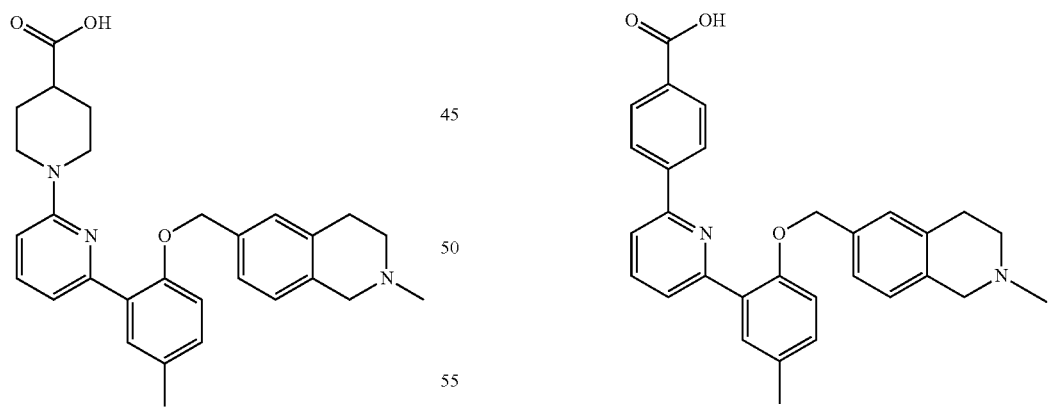

Pyridine 1-1 (1.15 g, 7.77 mmol) is combined with amine 15-57 (1.20 mL, 7.77 mmol) and DIEA (diisopropylethylamine) (1.62 mL, 9.32 mmol) in DMF (12 mL), then heated to 108° C. for 4 h. The mixture is diluted with H₂O and extracted with EtOAc. The combined organics are dried over MgSO₄, filtered, then concentrated in vacuo. The crude residue is purified by flash chromatography on silica gel (using a solvent gradient of 0-100% EtOAc:heptane) to provide 15-58 (0.88 g).

The title compound 45 is prepared from intermediate 15-58 according to the procedure outlined in Example 14. MS, electrospray, m/z=472.3 [M+H], rt 0.48 min.

Example 16

Preparation of 4-{6-[5-methyl-2-(2-methyl-1,2,3,4-tetrahydroisoquinolin-6-ylmethoxy)phenyl]pyridin-2-yl}benzoic acid (Compound 39, Table 1)

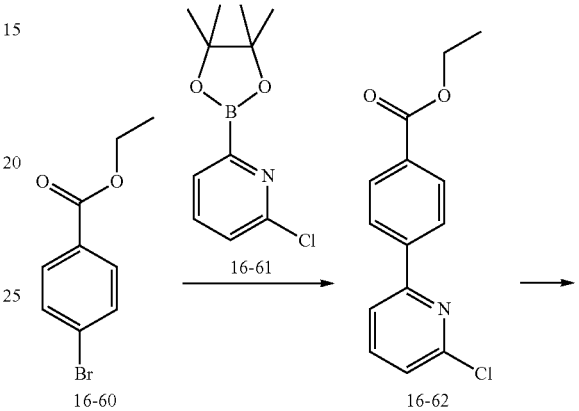

Bromide 16-60 (75.0 mg, 0.313 mmol), boronate 16-61 (75.0 mg, 0.327 mmol) and Pd(PPh₃)₄ (30 mg, 0.026 mmol) are combined in a mixture of 1,2-DME (4 mL) and aqueous Na₂CO₃ solution (0.5 mL, 2M, 1.0 mmol). The resulting mixture is irradiated at 110° C. for 30 min, then filtered and concentrated in vacuo. The residue is purified by column chromatography on silica gel (using a solvent gradient of 5-50% EtOAc:heptane) to afford intermediate 16-62 (70 mg).

The title compound 39 is prepared from intermediate 16-62 according to the procedure outlined in General Example 14. MS, electrospray, m/z=465.3 [M+H], rt 1.60 min.

Example 17

Preparation of 1-methyl-5-{6-[5-methyl-2-(2-methyl-1,2,3,4-tetrahydroisoquinolin-6-ylmethoxy)phenyl]pyridin-2-yl}-1H-pyrazole-3-carboxylic acid (Compound 44, Table 1)

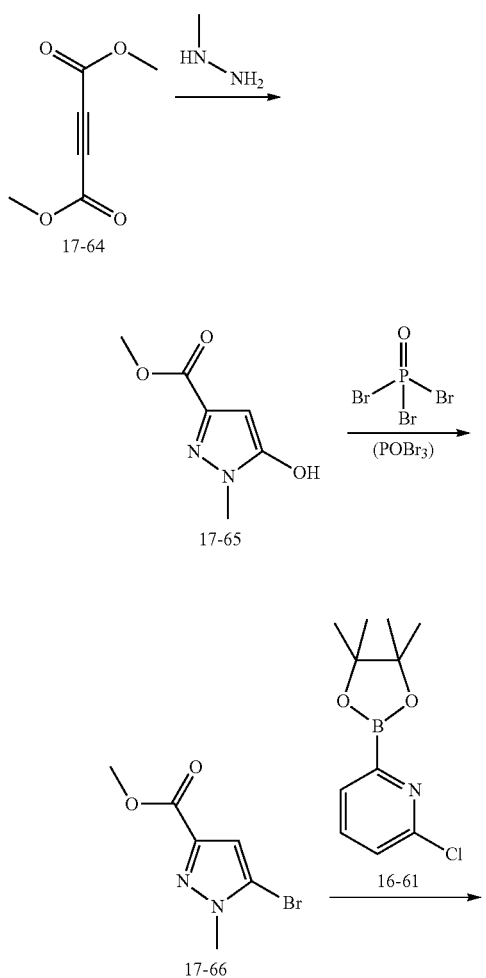

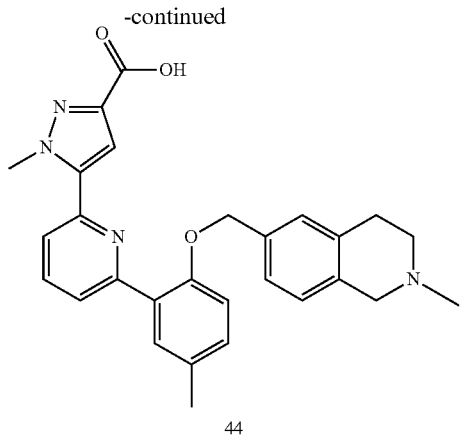

Methylhydrazine (37.4 mL, 704 mmol) is added to a solution of alkyne 17-64 (100 g, 704 mmol) in Et₂O (450 mL) cooled to −5° C. The resulting mixture is allowed to stir at 0° C. for 1 h, then is filtered to collect the solids. The solids are rinsed with additional Et₂O, then dried at 40° C. This material is heated in a 120° C. oil bath for 10 min then cooled to room temperature and recrystallized from MeOH to afford intermediate 17-65 (80 g).

Intermediate 17-65 (200 mg, 1.28 mmol) and POBr₃ (500 mg, 1.74 mmol) are dissolved in MeCN (30 mL) and the resulting solution is heated in a sealed flask at 80° C. for 3 h. The solution is cooled down and slowly poured into saturated NaHCO₃ solution (50 mL) and extracted with EtOAc. The combined extracts is washed with brine, dried over MgSO₄ and concentrated to afford intermediate 17-66 (200 mg).

Boronate 16-61 (150 mg, 0.626 mmol), intermediate 17-66 (150 mg, 0.685 mmol), Pd(PPh₃)₄ (75.0 mg, 0.065 mmol) and aqueous Na₂CO₃ solution (1.0 mL, 2M, 2.0 mmol) are combined in 1,2-DME (5 mL), then irradiated at 110° C. for 30 min. Upon cooling to room temperature, the mixture poured into H₂O and extracted with EtOAc. The organics are dried over Na₂SO₄, filtered, and concentrated in vacuo. The remaining residue is purified by column chromatography on silica gel (using a solvent gradient of 5-50% EtOAc:heptane) to deliver intermediate 17-67 (120 mg).

The title compound 44 is prepared from intermediate 17-67 according to the procedure outlined in Example 14. MS, electrospray, m/z=469.3 [M+H], rt 1.39 min.

Example 18

Preparation of 5-methyl-1-{6-[5-methyl-2-(2-methyl-1,2,3,4-tetrahydro-isoquinolin-6-ylmethoxy)phenyl]pyridin-2-yl}-1H-pyrazole-4-carboxylic acid (Compound 43, Table 1)

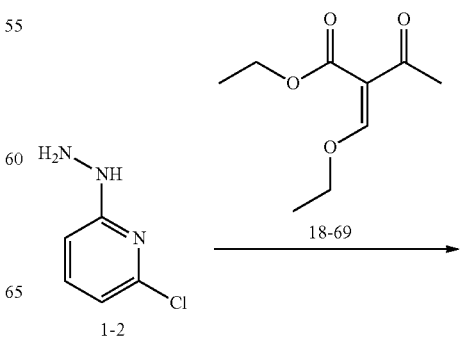

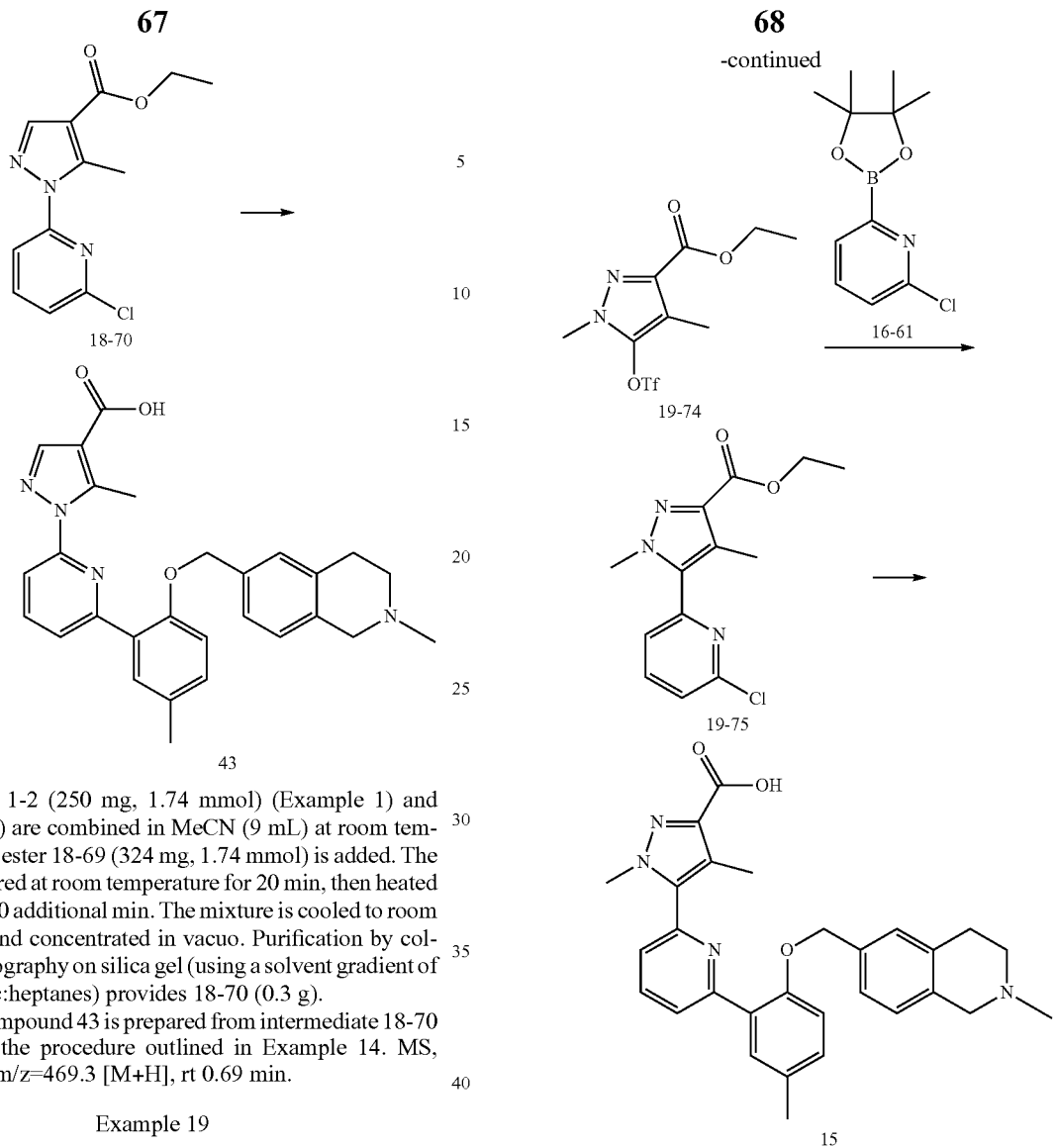

Compound 1-2 (250 mg, 1.74 mmol) (Example 1) and Et₃N (0.3 mL) are combined in MeCN (9 mL) at room temperature, then ester 18-69 (324 mg, 1.74 mmol) is added. The mixture is stirred at room temperature for 20 min, then heated to 60° C. for 30 additional min. The mixture is cooled to room temperature and concentrated in vacuo. Purification by column chromatography on silica gel (using a solvent gradient of 0-30% EtOAc:heptanes) provides 18-70 (0.3 g).

The title compound 43 is prepared from intermediate 18-70 according to the procedure outlined in Example 14. MS, electrospray, m/z=469.3 [M+H], rt 0.69 min.

Example 19

Preparation of 1,4-dimethyl-5-{6-[5-methyl-2-(2-methyl-1,2,3,4-tetrahydroisoquinolin-6-ylmethoxy) phenyl]pyridin-2-yl}1H-pyrazole-3-carboxylic acid (Compound 15, Table 1)

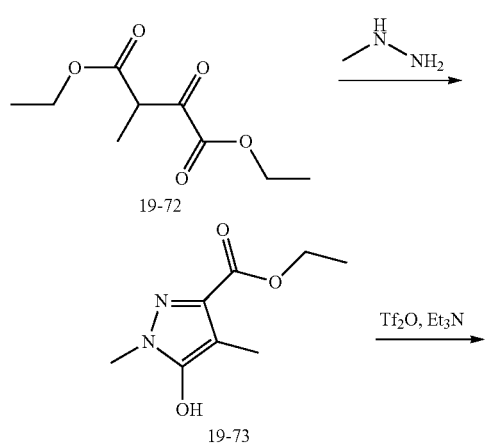

Ester 19-72 (10 g, 49 mmol), glacial AcOH (10 mL), and methylhydrazine (2.96 g, 64.0 mmol) are combined in absolute EtOH (50 mL) at room temperature. The mixture is heated to reflux for 3 days, then cooled to room temperature and concentrated in vacuo. A 1:1 mixture of heptanes:EtOAc is added and the product crystallizes out of solution. The solid is collected by filtration, then washed with heptanes and dried in vacuo to give 8.9 g of 19-73.

Intermediate 19-73 (1.0 g, 5.4 mmol) is dissolved DCM (25 mL), then cooled to 0° C. Et₃N (830 mg, 8.10 mmol) is added in one portion, followed by the dropwise addition of Tf₂O (1.8 g, 6.5 mmol). Upon complete addition of the reagents, the mixture is stirred at 0° C. for 30 min. The reaction is then quenched with saturated NaHCO₃ solution, and extracted with DCM. The combined the organics are dried over Na₂SO₄, then filtered and concentrated in vacuo to afford 19-74 (1.5 g).

Intermediate 19-74 (400 mg, 1.30 mmol) is placed combined with boronate 16-61 (333 mg, 1.40 mmol), Pd(PPh₃)₄ (140 mg, 0.12 mmol), and aqueous Na₂CO₃ solution (2.57 mL, 2.0 M, 5.14 mmol) in 1,2-DME (5 mL). The mixture is irradiated at 120° C. for 30 min, then cooled to room temperature and concentrated in vacuo. The crude material is purified by column chromatography on silica gel (using a solvent gradient of 5-100% EtOAc:heptanes) to provide 19-75 (65 mg).

The title compound 15 was prepared from intermediate 19-75 according to the procedure outlined in Example 14. MS, electrospray, m/z=483.3 [M+H], rt 0.65 min.

The following compounds from Table 1 are prepared from intermediates 19-75 and 11-45 according to the procedure described in Example 12.

Compound 78: MS, electrospray, m/z=496.9 [M+H], rt 0.72 min.

Example 20

Preparation of 5-{6-[5-methyl-2-(2-methyl-1,2,3,4-tetrahydroisoquinolin-6-ylmethoxy)phenyl]pyridin-2-yl}-thiophene-2-carboxylic acid (Compound 36, Table 1)

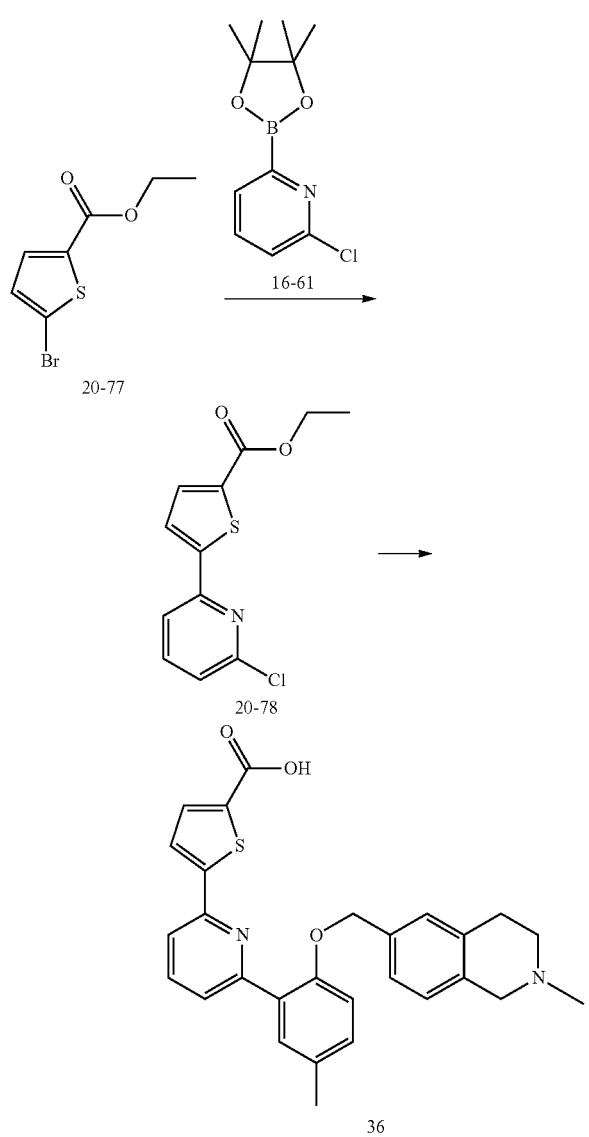

0.061 mmol), and aqueous Na$_2$CO$_3$ solution (2.0 mL, 2.0 M, 4.0 mmol) in 1,2-DME (8 mL). The mixture is irradiated at 120° C. for 40 min, then cooled to room temperature and concentrated under a stream of N$_2$. The crude material is purified by column chromatography on C18 silica (using a solvent gradient of 5-95% MeCN:H$_2$O+0.1% TFA) to provide intermediate 20-78 (321 mg).

The title compound 36 is prepared from intermediate 20-78 according to the procedure outlined in Example 14. MS, electrospray, m/z=471.3 [M+H], rt 0.75 min.

Example 21

Preparation of 4-methyl-5-{6-[5-methyl-2-(2-methyl-1,2,3,4-tetrahydro-isoquinolin-6-ylmethoxy)phenyl]pyridin-2-yl}-thiophene-2-carboxylic acid (Compound 37, Table 1)

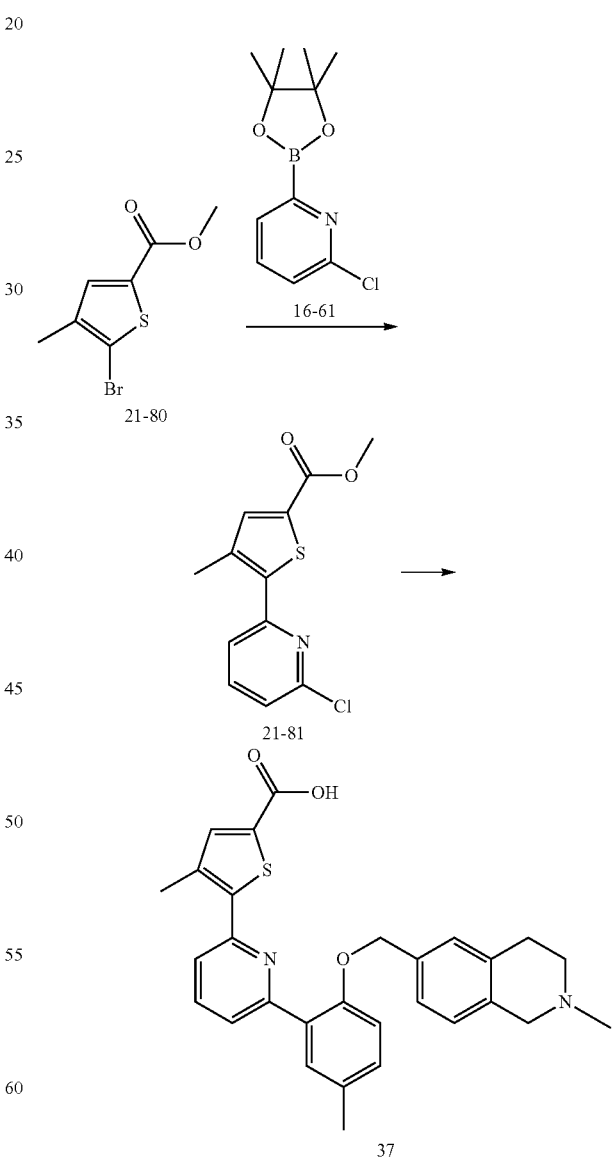

Bromide 20-77 (300 mg, 1.27 mmol) is combined with boronate 16-61 (370 mg, 1.55 mmol), Pd(PPh$_3$)$_4$ (70 mg, Bromide 21-80 (300 mg, 1.27 mmol) is combined with boronate 16-61 (370 mg, 1.55 mmol), Pd(PPh$_3$)$_4$ (70 mg, 0.061 mmol), and aqueous Na$_2$CO$_3$ solution (1.9 mL, 2.0M, 3.8 mmol) in 1,2-DME (10 mL). The mixture is irradiated at 120° C. for 40 min, then directly purified by column chromatography on silica gel (using a solvent gradient of 5-60% EtOAc:heptane) to provide intermediate 21-81 (192 mg).

The title compound 37 is prepared from intermediate 21-81 according to the procedure outlined in Example 14. MS, electrospray, m/z=485.3 [M+H], rt 0.80 min.

Example 22

Preparation of 2-{6-[2-(2,5-dimethyl-1,2,3,4-tetrahydroisoquinolin-6-ylmethoxy)-5-methylphenyl]pyridin-2-yl}-3-methyl-3H-imidazole-4-carboxylic acid (Compound 48, Table 1)

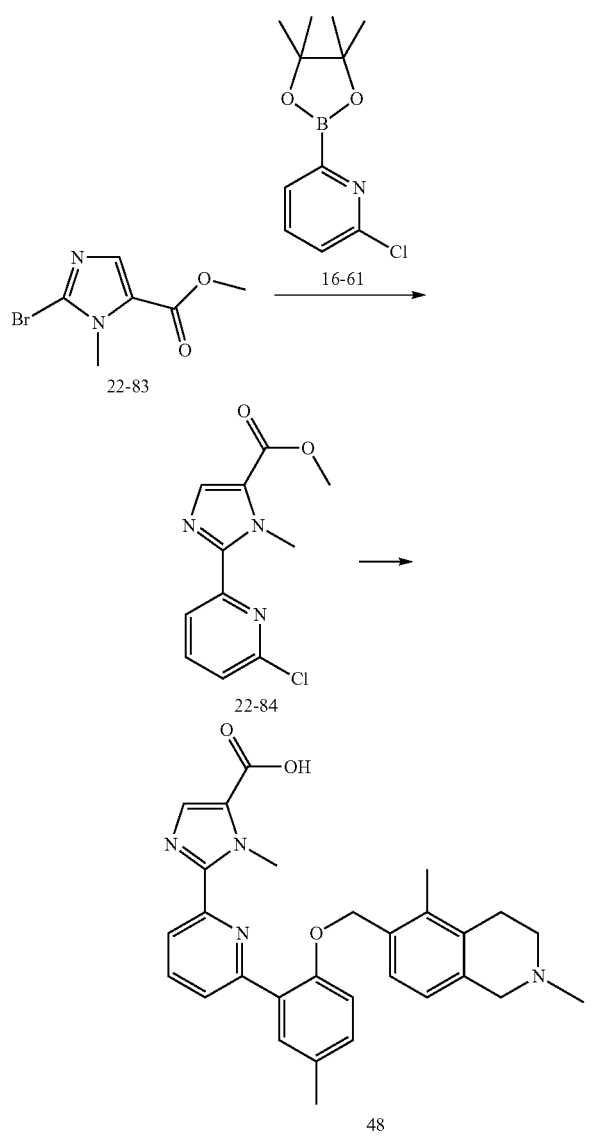

Bromide 22-83 (1.00 g, 4.56 mmol) is combined with boronate 16-61 (1.30 g, 5.43 mmol), Pd(PPh$_3$)$_4$ (275 mg, 0.238 mmol), and aqueous Na$_2$CO$_3$ solution (5.0 mL, 2.0 M, 10.0 mmol) in 1,2-DME (15 mL). The mixture is irradiated at 120° C. for 40 min, then cooled to room temperature and concentrated under a stream of N$_2$. The crude material is purified by column chromatography on C18 silica (using a solvent gradient of 5-75% MeCN:H$_2$O+0.1% TFA) to afford intermediate 22-84 (370 mg).

The title compound 48 is prepared from intermediate 22-84 according to the procedure outlined in Example 14. MS, electrospray, m/z=481.3 [M−H], rt 0.68 min.

The following compound from Table 1 is prepared according to the procedure described in Example 22, using the appropriate starting materials and purification conditions Compound 41: MS, electrospray 469.3 [M+H], rt 0.62 min.

Example 23

Preparation of 2-{6-[5-methyl-2-(2-methyl-1,2,3,4-tetrahydroisoquinolin-6-ylmethoxy)phenyl]pyridin-2-yl}-3-trifluoromethyl-3H-imidazole-4-carboxylic acid (Compound 49, Table 1)

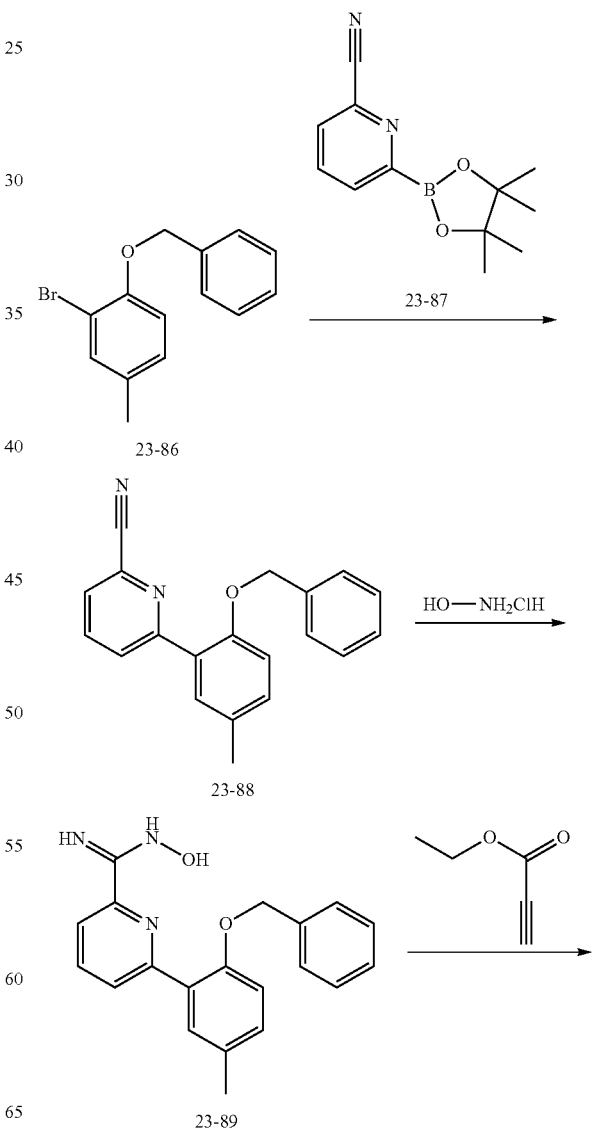

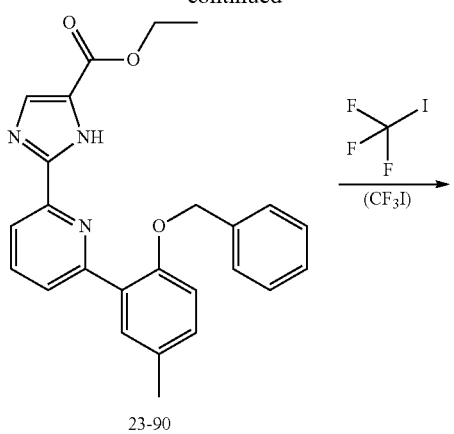

23-90

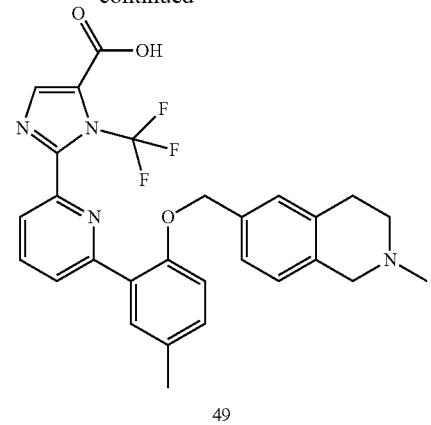

49

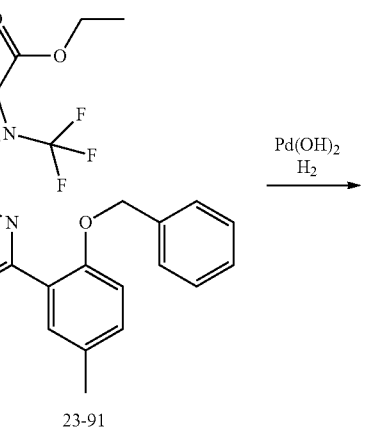

23-91

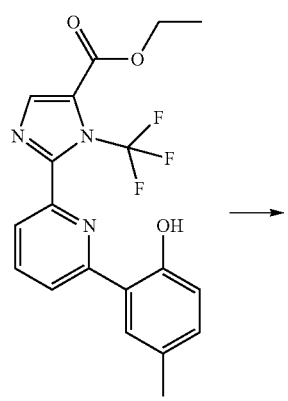

23-92

Bromide 23-86 (660 mg, 2.37 mmol) and boronate 23-87 (500 mg, 2.17 mmol) are combined with Pd(PPh$_3$)$_4$ (126 mg, 0.109 mmol), and aqueous Na$_2$CO$_3$ solution (2.4 mL, 2.0 M, 4.8 mmol) in 1,2-DME (8 mL). The mixture is irradiated at 120° C. for 40 min, then cooled to room temperature and concentrated under a stream of N$_2$. The crude material is purified by column chromatography on silica gel (using a solvent gradient 5-70% EtOAc/heptane) to afford intermediate 23-88 (167 mg).

Intermediate 23-88 (175 mg, 0.583 mmol) is combined with hydroxylamine hydrochloride (HONH$_2$.HCl) (102 mg, 1.47 mmol) and K$_2$CO$_3$ (81.0 mg, 0.586 mmol) in a mixture of EtOH (3 mL) and H$_2$O (3 mL), then heated to 65° C. for 15 h. The mixture is concentrated under a stream of N$_2$, then triturated with H$_2$O (10 mL). The solids are collected by filtration and washed with additional H$_2$O (10 mL), then dried under vacuum (30 mm Hg, 45° C.) for 17 h to afford intermediate 23-89 (152 mg).

Ethyl propiolate (0.17 mL, 1.7 mmol) and intermediate 23-89 (150 mg, 0.450 mmol) are combined in MeOH (2.5 mL), then heated to reflux for 15 h in a sealed vial. The solvent is removed in vacuo, and the crude residue is resuspended in Bu$_2$O (3 mL). The solution is irradiated at 180° C. for 2 h, then directly purified by column chromatography on silica gel (using a solvent gradient of 5-65% EtOAc/heptane) to deliver intermediate 23-90 (120 mg).

Intermediate 23-90 (115 mg, 0.278 mmol) and KOt-Bu (94.0 mg, 0.838 mmol) are dissolved in dry DMF (3 mL) at room temperature in a septum capped vial, then stirred for 5 min. Gaseous CF$_3$I is bubbled through the mixture for 10 min, then the mixture is heated at 80° C. for 20 h. The vial is uncapped and Cs$_2$CO$_3$ (100 mg, 0.308 mmol) is added and the mixture is resaturated with CF$_3$I for 5 min. The vessel is resealed and heated at 80° C. for 14 h, then concentrated under a stream of N$_2$. The remaining residue is purified by column chromatography on C18 silica (using a solvent gradient of 50-95% MeCN/water+0.1% TFA) to furnish intermediate 23-91 (81 mg).

Intermediate 23-91 (80.0 mg, 0.166 mmol) and Pd(OH)$_2$ (50 mg) are combined in EtOH under H$_2$ (1 atm, balloon), then stirred at room temperature for 16 h. The H$_2$ atmosphere is replaced with N$_2$, then the crude mixture is filtered through a diatomaceous earth plug (wetted with water). The diatomaceous earth is rinsed with EtOAc and the filtrate is eluted through a 10 g silica gel cartridge using additional EtOAc (50 mL). The filtrate is concentrated in vacuo to afford intermediate 23-92 (72 mg).

The title compound 49 is prepared from intermediate 23-92 according to the procedure outlined in Example 14. MS, electrospray, m/z=521.5 [M−H], rt 1.44 min.

Example 24

Preparation of 6-intermediate hydroxymethyl-3,4-dihydro-1H-isoquinoline-2-carboxylic acid tert-butyl ester (24-95)

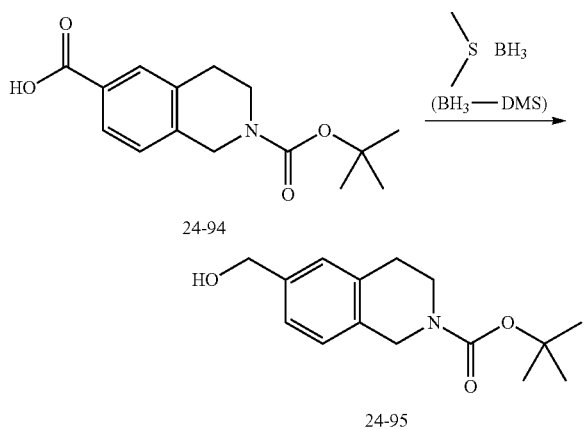

To a solution of acid 24-94 (2.40 g, 8.65 mmol) in THF (50 mL) at room temperature is added neat BH₃-DMS complex (1.8 mL, 19 mmol). The mixture is stirred at room temperature for 24 h, then sequentially quenched with H₂O (10 mL) and aqueous Na₂CO₃ solution (15 mL). After 15 min of vigorous stirring, the mixture is diluted with EtOAc, and the organic phase is separated. The organic phase is subsequently rinsed with 1 N HCl, then dried over MgSO₄, filtered, and concentrated in vacuo. The crude product is purified by column chromatography on silica gel (using a solvent gradient of 12-100% EtOAc:heptane) to provide the desired intermediate 24-95 (2.0 g).

Example 25

Preparation of intermediate 6-hydroxymethyl-5-methyl-3,4-dihydro-1H-isoquinoline-2-carboxylic acid tert-butyl ester (25-96)

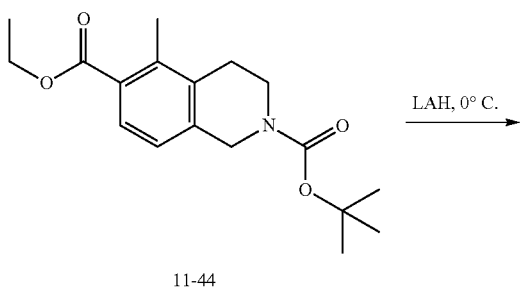

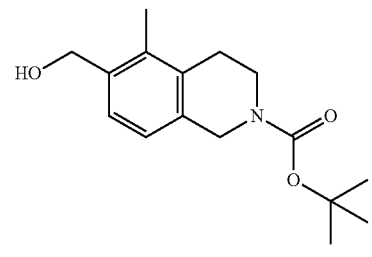

To a solution of LAH (12.5 g, 330 mmol) in THF (400 mL) cooled to −30° C. is added dropwise a solution of compound 11-44 (35.0 g, 110 mmol) (Example 11) in THF (400 mL) over 30 min. After addition, the reaction mixture is stirred at 0° C. for 0.5 h, then treated with H₂O and DCM. The organic phase is separated, washed with brine, dried over Na₂SO₄, filtered, and concentrated in vacuo. The crude product is purified by column chromatography on silica gel (using 10:1 petroleum ether:EtOAc) to provide the desired intermediate 25-96 (21.1 g).

Example 26

Preparation of 1-{6-[5-Methyl-2-(1,2,3,4-tetrahydroisoquinolin-6-ylmethoxy)phenyl]pyridin-2-yl}-5-trifluoromethyl-1H-pyrazole-4-carboxylic acid (Compound 4, Table 1)

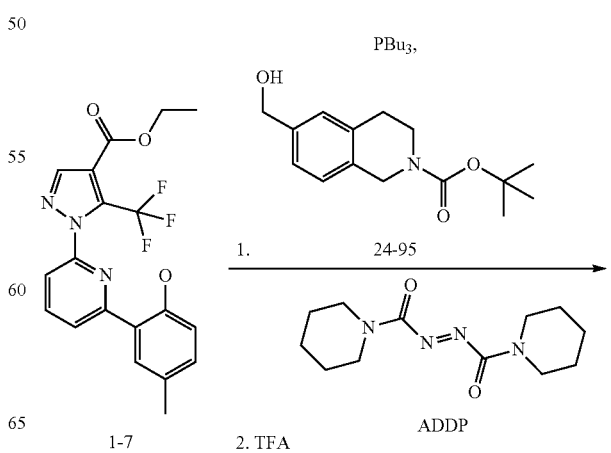

-continued

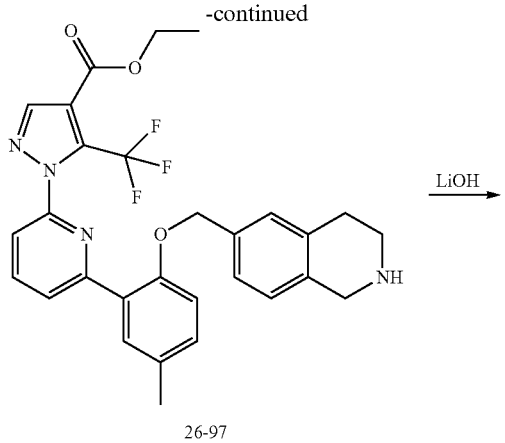

26-97

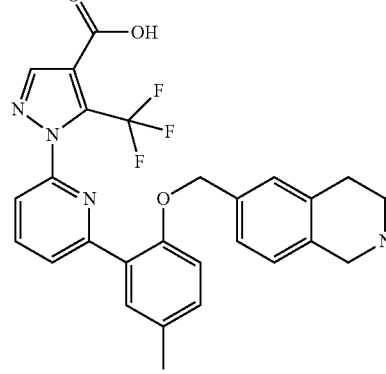

4

PBu₃ (4.00 mL, 15.9 mmol) is added to a solution of 1-7 (2.23 g, 5.70 mmol), ADDP (4.00 g, 15.9 mmol), and 26-95 (2.00 g, 7.60 mmol) in PhMe/THF (2:1) (120 mL) at room temperature. The mixture is then heated to 80° C. for 14 h, before cooling to room temperature. The solvent is evaporated in vacuo, and the remaining solids are triturated with EtOAc, then filtered through diatomaceous earth. The filtrate is concentrated in vacuo, and purified by column chromatography on silica gel (using a solvent gradient of 5-60% EtOAc: heptane) to deliver the desired intermediate. The product is subsequently redissolved in DCM (20 mL) at room temperature, then treated with TFA (5 mL). After 2 h, the mixture is quenched with saturated aqueous NaHCO₃, and the layers are separated using a hydrophobic frit. The organic filtrate is dried over Na₂SO₄, then filtered and concentrated in vacuo. The crude product is purified by column chromatography on silica gel (using a solvent gradient of 0-10% MeOH:DCM) to provide intermediate 26-97 (2.06 g). ES, electrospray, m/z=538.2 [M+H], rt 0.90 min.

Compound 26-97 (53.0 mg, 0.099 mmol) is dissolved in a mixture of THF (1 mL) and H₂O (0.5 mL), then treated with solid LiOH.H₂O (40.0 mg, 0.953 mmol). The mixture is heated to 50° C. for 5 h, then cooled to room temperature and quenched with 3N HCl (1 mL). The resulting solution is applied directly to a C18 silica column and purified by gradient elution (5-60% MeCN:water+0.1% TFA) to afford the title compound 4 (43 mg). MS, electrospray, m/z=509.3 [M+H], rt 0.71 min.

Example 27

Preparation of 1-{6-[2-(2-acetyl-1,2,3,4-tetrahydroisoquinolin-6-ylmethoxy)-5-methylphenyl]pyridin-2-yl}-5-trifluoromethyl-1H-pyrazole-4-carboxylic acid (Compound 6, Table 1)

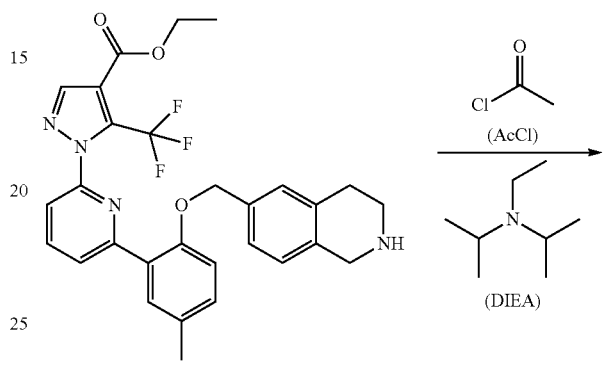

26-97

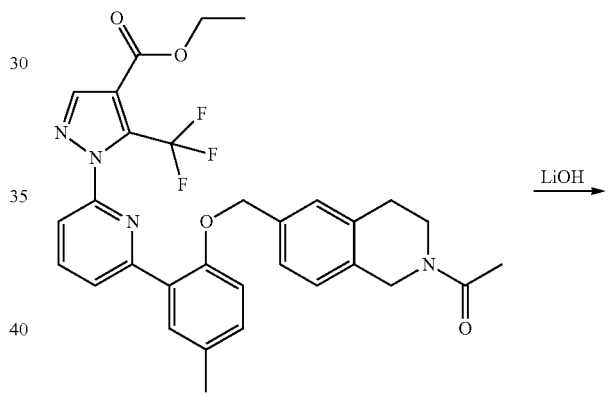

27-99

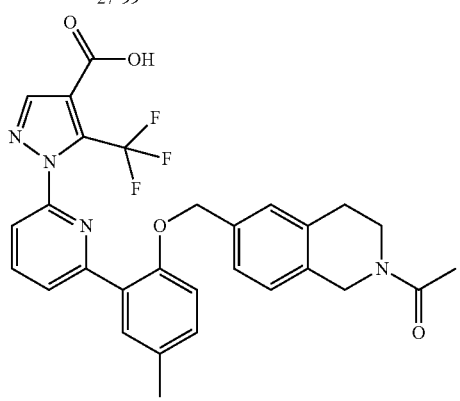

6

Compound 26-97 (40.0 mg, 0.075 mmol) is combined with DIEA (28.6 μL, 0.164 mmol) in DCM (1.0 mL) at room temperature, then treated with AcCl (5.8 μL, 0.082 mmol). The mixture is stirred for 1 h, then partitioned between H₂O and EtOAc. The phases are separated and the organic phase is sequentially washed with 1N HCl, saturated aqueous NaHCO$_3$, then brine. The organic phase is dried over Na$_2$SO$_4$, filtered, and concentrated to afford intermediate 27-99 (43 mg).

The title compound 6 is prepared from compound 27-99 (42 mg, 0.073 mmol) according to the hydrolysis procedure described in Example 14. MS, electrospray, m/z=551.3 [M+H], r.t. 1.03 min.

Example 28

Preparation of 1-(6-{2-[2-(3-carboxypropane-1-sulfonyl)-1,2,3,4-tetrahydroisoquinolin-6-ylmethoxy]-5-methylphenyl}pyridin-2-yl)-5-trifluoromethyl-1H-pyrazole-4-carboxylic acid (Compound 3, Table 1)

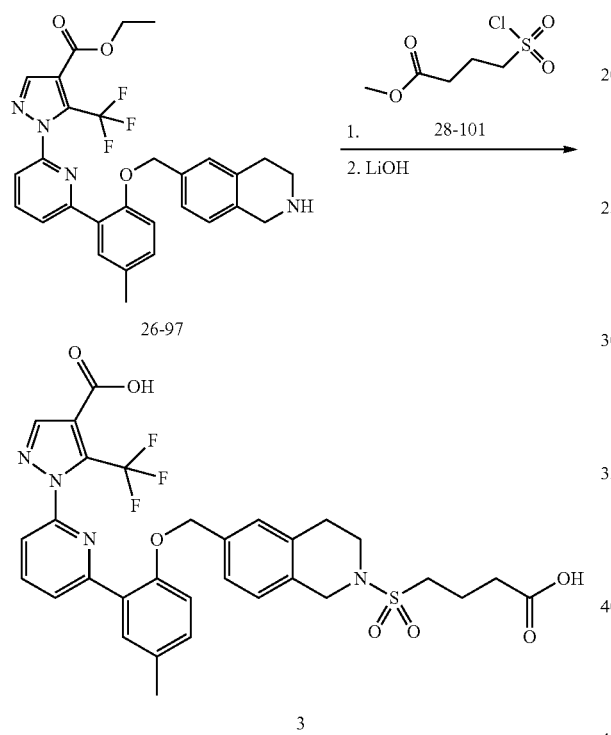

Compound 26-97 (54.0 mg, 0.101 mmol) is dissolved in a mixture of DCM (2 mL) and pyridine (24.0 µL, 0.303 mmol), then cooled to 0° C. Sulfonyl chloride 28-101 (30.0 µL, 0.150 mmol) is added via syringe, then the mixture is allowed to warm to room temperature and is stirred for 14 h. A few crystals of 4-DMAP are added along with additional 28-101 (20.0 µL, 0.101 mmol), and the mixture is heated to 50° C. for 3 h. Upon cooling to room temperature, the reaction is applied directly to a silica gel column and purified using a solvent gradient of 0-60% EtOAc:heptane. The clean product is concentrated in vacuo, then dissolved in a mixture of THF (1 mL) and H$_2$O (0.5 mL), and treated with LiOH.H$_2$O (30 mg, 0.71 mmol). The mixture is stirred for 15 h at 50° C., then cooled to room temperature and quenched with 3 N HCl (1 mL). The reaction is extracted with DCM, dried over Na$_2$SO$_4$, filtered, and concentrated in vacuo to deliver the title compound 3 (39 mg). MS, electrospray, m/z=657.3 [M–H], rt 1.04 min.

The following compounds from Table 1 are prepared according to the procedure described in Example 28, using the appropriate starting materials and purification conditions:
Compound 1: MS, electrospray 631.3 [M+H], rt 1.03 min.

Compound 5: MS, electrospray 585.3 [M–H], rt 1.07 min.

Example 29

Preparation of 1-(6-{5-methyl-2-[2-(tetrahydrofuran-3-yl)-1,2,3,4-tetrahydroisoquinolin-6-ylmethoxy]phenyl}pyridin-2-yl)-5-trifluoromethyl-1H-pyrazole-4-carboxylic acid (Compound 35, Table 1)

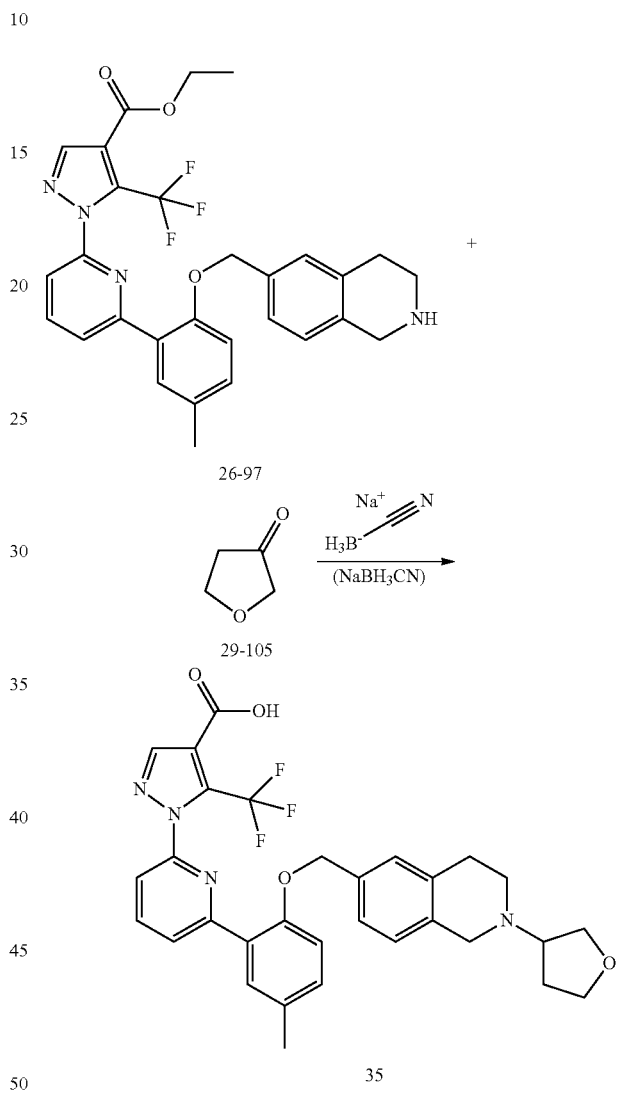

Compound 26-97 (70.0 mg, 0.130 mmol) is combined with ketone 29-105 (17.0 µL, 0.158 mmol) and oven dried 4 Å molecular sieves in dry MeOH (1.5 mL) containing AcOH (1 drop). Sodium cyanoborohydride (NaBH$_3$CN) (11.0 mg, 0.175 mmol) is added, and mixture the stirred at room temperature for 3 h, then heated to 50° C. for 13 h. The mixture is cooled to room temperature and concentrated to dryness under a stream of N$_2$. The residue is purified by column chromatography on C18 silica (using a solvent gradient of 5-60% MeCN/water+0.1% TFA) to deliver the intermediate ester. This material is resuspended in a mixture of MeOH (1 mL), H$_2$O (1 mL) and THF (2 mL), then treated with LiOH.H$_2$O (50 mg, 1.2 mmol). The resulting mixture is stirred at 50° C. for 14 h, then concentrated under a stream of N$_2$, and purified by column chromatography on C18 silica (using a solvent gradient of 5-70% MeCN:water+0.1% TFA) to afford the title compound 35 (69 mg). MS, electrospray 577.1 [M−H], rt 0.78 min.

The following compounds from Table 1 are prepared according to the procedure described in Example 29, using the appropriate starting materials and purification conditions:
Compound 12: MS, electrospray 549.2 [M+H], rt 0.77 min.
Compound 14: MS, electrospray 567.3 [M−H], rt 0.87 min.
Compound 16: MS, electrospray 563.1 [M+H], rt 0.76 min.
Compound 17: MS, electrospray 577.3 [M+H], rt 0.81 min.
Compound 19: MS, electrospray 591.3 [M+H], rt 0.87 min.
Compound 33: MS, electrospray 659.3 [M+H], rt 0.86 min.
Compound 34: MS, electrospray 593.3 [M+H], rt 0.76 min.
Compound 22: MS, electrospray 593.3 [M+H], rt 0.80 min.
Compound 21: MS, electrospray 551.3 [M+H], rt 0.80 min.
Compound 23: MS, electrospray 593.3 [M+H], rt 0.79 min.
Compound 26: MS, electrospray 607.3 [M+H], rt 0.82 min.
Compound 25: MS, electrospray 621.3 [M+H], rt 0.82 min.
Compound 27: MS, electrospray 599.3 [M+H], rt 0.87 min.
Compound 42: MS, electrospray 613.3 [M+H], rt 0.88 min.
Compound 20: MS, electrospray 613.3 [M+H], rt 0.89 min.
Compound 18: MS, electrospray 600.3 [M+H], rt 0.83 min.
Compound 24: MS, electrospray 601.3 [M+H], rt 0.79 min.
Compound 28: MS, electrospray 615.3 [M+H], rt 0.81 min.
Compound 29: MS, electrospray 620.3 [M+H], rt 0.92 min.
Compound 30: MS, electrospray 602.6 [M+H], rt 0.78 min.
Compound 31: MS, electrospray 604.3 [M+H], rt 0.86 min.
Compound 32: MS, electrospray 617.3 [M+H], rt 0.81 min.
Compound 50: MS, electrospray 582.3 [M+H], rt 0.84 min.
Compound 51: MS, electrospray 553.4 [M−H], rt 0.71 min.
Compound 53: MS, electrospray 555.3 [M+H], rt 0.78 min
Compound 54: MS, electrospray 539.4 [M+H], rt 0.61 min.

Example 30

Preparation of 6-bromomethyl-3,4-dihydro-1H-isoquinoline-2-carboxylic acid tert-butyl ester (30-106)

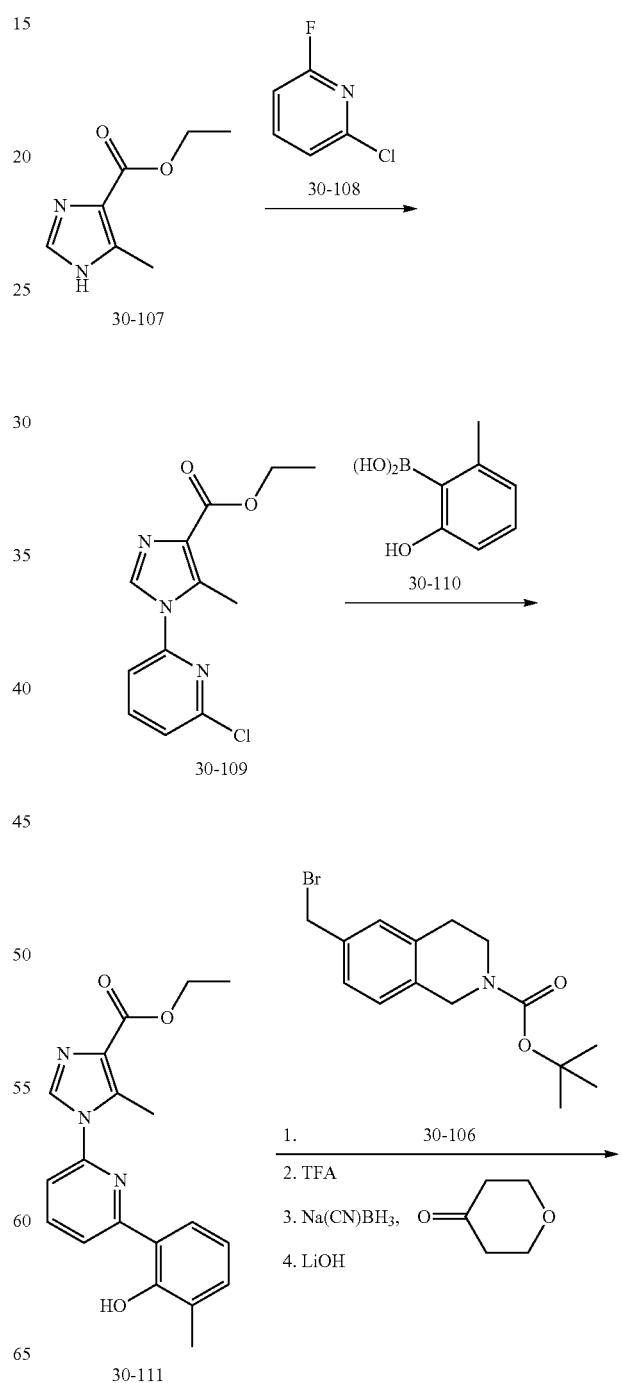

A solution of intermediate 24-95 (2.0 g, 7.6 mmol) and pyridine (1.2 mL, 11 mmol) in DCM (100 mL) is treated in one portion with triphenylphosphine dibromide (4.8 g, 11 mmol) at 0° C. The mixture is allowed to stir for 30 min, then concentrated in vacuo. The resulting crude material is purified by column chromatography on silica gel (using a gradient of 5-60% EtOAc/heptane) to afford the title compound (2.2 g).

Example 31

Preparation of 5-methyl-1-[6-[3-methyl-2-[(2-tetrahydropyran-4-yl-3,4-dihydro-1H-isoquinolin-6-yl)methoxy]phenyl]-2-pyridyl]imidazole-4-carboxylic acid (Compound 57, Table 1)

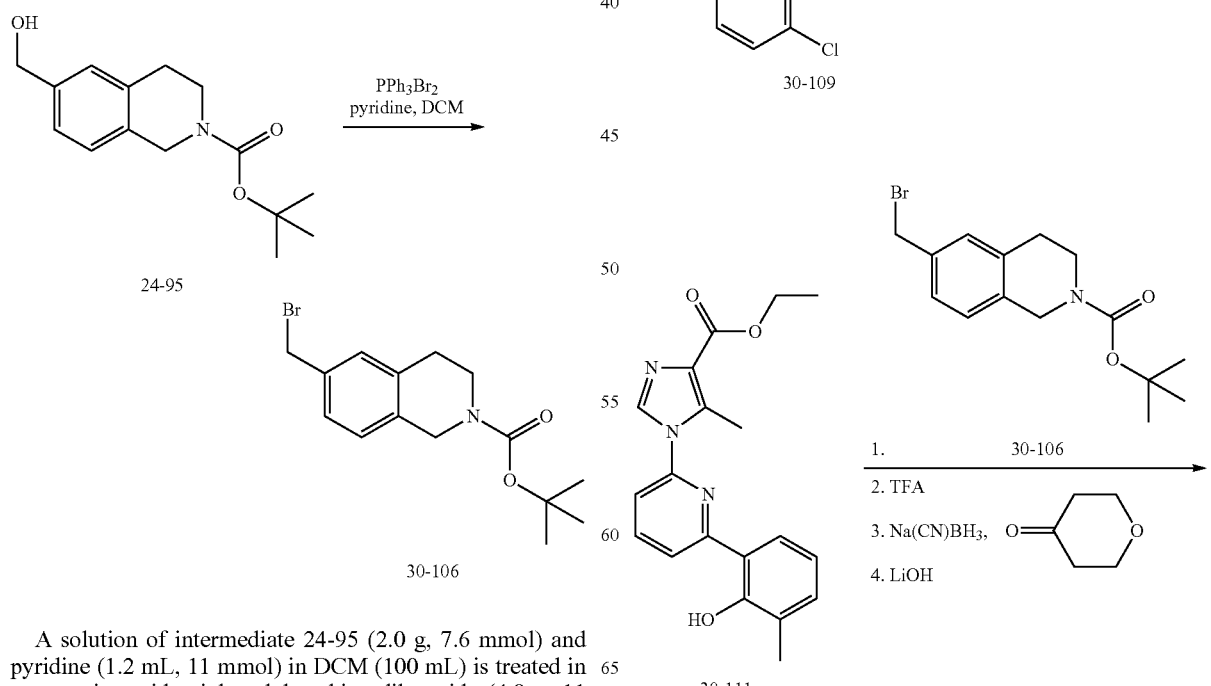

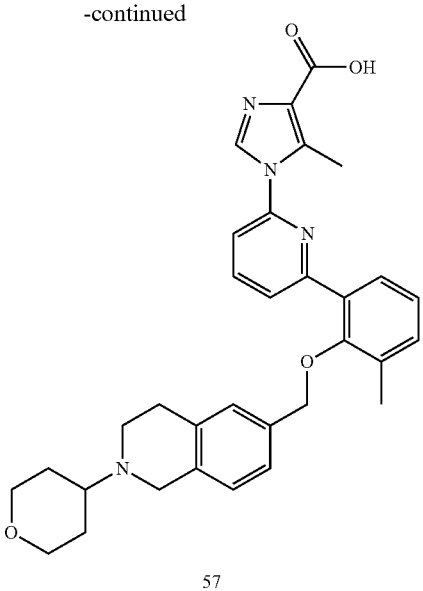

57

Imidazole 30-107 (3.0 g, 19.5 mmol) is combined with pyridine 30-108 (5.16 g, 39.2 mmol) and $Cs_2CO_3$ (12.7 g, 38.9 mmol) in N,N-DMA (60 mL), then irradiated at 150° C. for 30 min. The resulting mixture is evaporated to dryness. Crude intermediate 30-109 (1.0 g, 3.76 mmol) is combined with $Pd(PPh_3)_4$ (400 mg, 0.35 mmol), 2M aqueous $Na_2CO_3$ solution (4 mL, 8 mmol), and 30-110 (740 mg, 4.87 mmol) in 1,2-DME (15 mL). The mixture is irradiated for 40 min at 120° C., then evaporated to dryness. The crude residue is purified by column chromatography on silica gel (using a gradient of 0-10% MeOH/DCM) to provide the intermediate 30-111 (1.36 g). Intermediate 30-111 (100 mg, 0.3 mmol), bromide 30-106 (120 mg, 0.36 mmol) and $Cs_2CO_3$ (180 mg, 0.55 mmol) are combined in DMF (6 mL) and heated to 40° C. for 3d. The solvent is then evaporated and the crude residue is purified by column chromatography on silica gel (using a gradient of 5-100% EtOAc/heptane) to provide the intermediate carbamate. The carbamate is dissolved in DCM (10 mL) and treated with TFA (1 mL) at room temperature. After 1.5 h, the mixture is neutralized with saturated $NaHCO_3$ solution and the layers are separated with a hydrophobic frit. The organic filtrate is concentrated to afford the crude amine. This material is combined with 4 Å molecular sieves (30 mg), tetrahydropyran 4-one (38 µL, 0.41 mmol), AcOH (10 µL), and $NaBH_3CN$ (24 mg, 0.38 mmol) in MeOH (4 mL). The mixture is stirred at room temperature for 45 minutes, and then heated to 50° C. for 16 h. The mixture is concentrated to dryness, and then the residue is purified by column chromatography on C18 silica gel (using a gradient of 5-95% MeCN/water+0.1% TFA) to afford the title compound 57 (69 mg). MS, electrospray, m/z=539.3 [M+H], rt 0.64 min.

The following compounds from Table I are prepared from intermediate 30-109 according to the procedure outlined in Example 31 using the appropriate reagents and purification conditions.

Compound 55: MS, electrospray, m/z=539.2 [M+H], rt 0.62 min)

Compound 56: MS, electrospray, m/z=560.2, [M+H], rt 0.66 min)

Compound 58: MS, electrospray, m/z=539.3, [M+H], rt 0.64 min)

The following compound from Table I is prepared from intermediate 14-53 according to the procedure outlined in Example 31 using the appropriate reagents and purification conditions.

Compound 60: MS, electrospray, m/z=553.4 [M+H], rt 0.72 min)

The following compounds from Table I are prepared from intermediate 18-70 according to the procedure outlined in Example 31 using the appropriate reagents and purification conditions.

Compound 64: MS, electrospray, m/z=538.3 [M+H], rt 0.73 min)

Compound 65: MS, electrospray, m/z=538.3 [M+H], rt 0.73 min)

The following compounds from Table I are prepared from intermediate 22-84 according to the procedure outlined in Example 31 using the appropriate reagents and purification conditions.

Compound 61: MS, electrospray, m/z=593.3 [M+H], rt 0.64 min)

Compound 66: MS, electrospray, m/z=539.3 [M+H], rt 1.25 min)

Compound 67: MS, electrospray, m/z=539.3 [M+H], rt 1.28 min)

Compound 68: MS, electrospray, m/z=553.3 [M+H], rt 1.19 min)

Compound 69: MS, electrospray, m/z=564.3 [M+H], rt 1.44 min)

Compound 70: MS, electrospray, m/z=564.3 [M+H], rt 1.25 min)

Compound 71: MS, electrospray, m/z=563.3 [M+H], rt 1.23 min)

Compound 72: MS, electrospray, m/z=550.3 [M+H], rt 1.33 min)

Compound 73: MS, electrospray, m/z=553.3 [M+H], rt 1.22 min)

Compound 74: MS, electrospray, m/z=573.3 [M+H], rt 1.37 min)

Compound 75: MS, electrospray, m/z=539.2 [M+H], rt 1.15 min)

Compound 76: MS, electrospray, m/z=551.4 [M+H], rt 1.52 min)

Compound 77: MS, electrospray, m/z=604.4 [M+H], rt 1.76 min)

The following compounds from Table I are prepared from intermediate 19-75 according to the procedure outlined in Example 31 using the appropriate reagents and purification conditions.

Compound 79: MS, electrospray, m/z=553.2 [M+H], rt 0.63 min)

Compound 80: MS, electrospray, m/z=567.2 [M+H], rt 0.66 min)

Compound 81: MS, electrospray, m/z=553.3 [M+H], rt 0.71 min)

Example 32

Preparation of 4-methyl-2-[6-[3-methyl-2-[(2-tetrahydropyran-4-yl-3,4-dihydro-1H-isoquinolin-6-yl)methoxy]phenyl]-2-pyridyl]thiazole-5-carboxylic acid (Compound 59, Table 1)

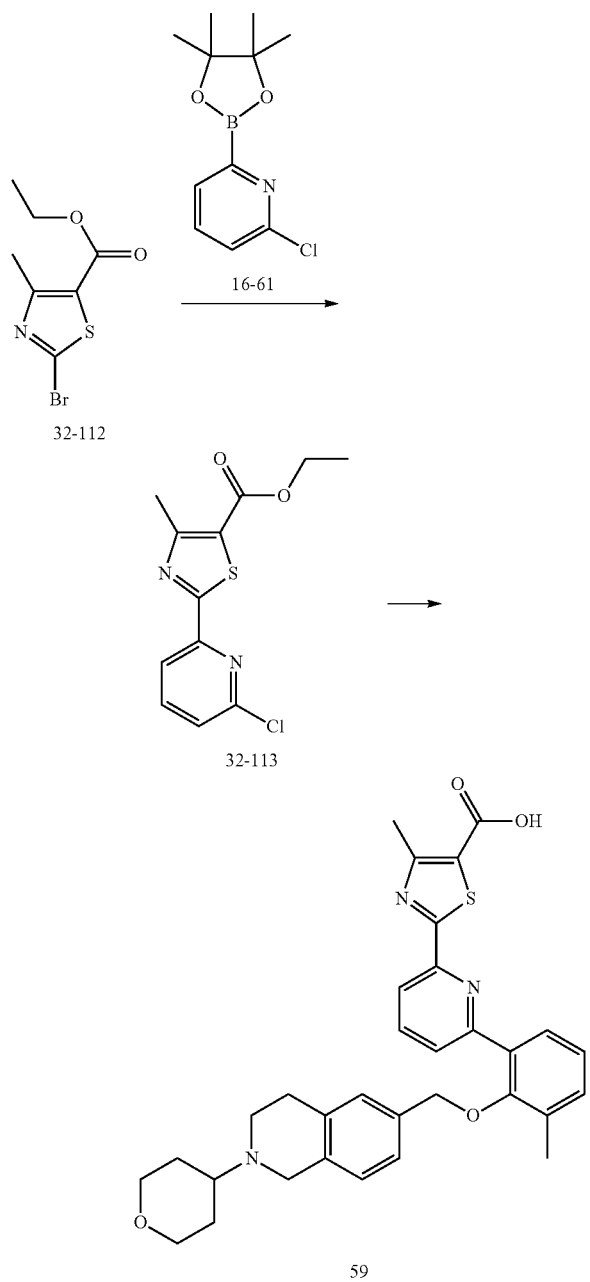

Thiazole 32-112 (250 mg, 1 mmol), boronic ester 16-61 (360 mg, 1.5 mmol), and Pd(PPh₃)₄ (60 mg, 0.05 mmol) are combined with 2 N aqueous Na₂CO₃ solution (1.5 mL, 3 mmol) in 1,2-DME (9 mL), and then irradiated at 120° C. for 30 min. The solvent is evaporated under N₂, and the crude residue purified by column chromatography on silica gel (using a gradient of 5-100% EtOAc/heptane) to afford intermediate 32-113 (77 mg).

The title compound 59 is prepared from intermediate 32-113 according the procedure described in Example 31. MS, electrospray, m/z=556.3 [M+H], rt 0.74 min.

Example 33

Preparation of 3-ethyl-2-[6-[3-methyl-2-[(2-tetrahydropyran-4-yl-3,4-dihydro-1H-isoquinolin-6-yl)methoxy]phenyl]-2-pyridyl]imidazole-4-carboxylic acid (Compound 63, Table 1)

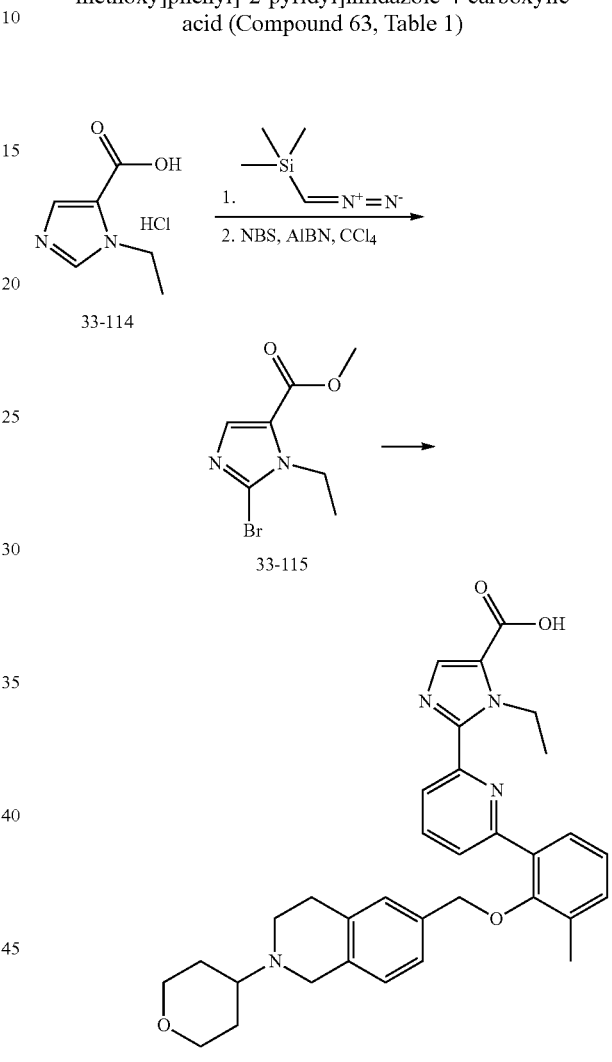

Imidazole 33-114 (500 mg, 2.8 mmol) is dissolved in (1:1) PhMe/MeOH (40 mL), then treated via syringe with a 2 M solution of TMSCHN₂ in hexanes (6 mL, 12 mmol). The mixture is allowed to stir at room temperature 1 h, then quenched with AcOH (1 mL). The mixture is then concentrated in vacuo, then redissolved in DCM (15 mL) and neutralized with sat. NaHCO₃ soln (30 mL). Separation of the layers and concentration of the organic phase affords the crude intermediate ester (269 mg).

The preceeding ester (265 mg, 1.7 mmol) NBS (612 mg, 3.4 mmol), and AIBN (15 mg, 0.1 mmol) are combined in CCl₄ (30 mL), and then heated to 50° C. for 4 h. The reaction is filtered hot through a short pad of diatomaceous earth, rinsing with additional CCl₄, then concentrated in vacuo to afford crude bromide 33-115 (450 mg).

The title compound 63 is prepared from crude intermediate 33-115 according the procedure described in Example 32. MS, electrospray, m/z=553.4 [M+H], rt 0.68 min.

Example 34

Preparation of 5-[6-[2-[2-[2-(4,4-difluorocyclohexyl)-3,4-dihydro-1H-isoquinolin-6-yl]ethyl]-3-methylphenyl]-2-pyridyl]-1-isopropyl-4-methyl-pyrazole-3-carboxylic acid (Compound 88, Table 1)

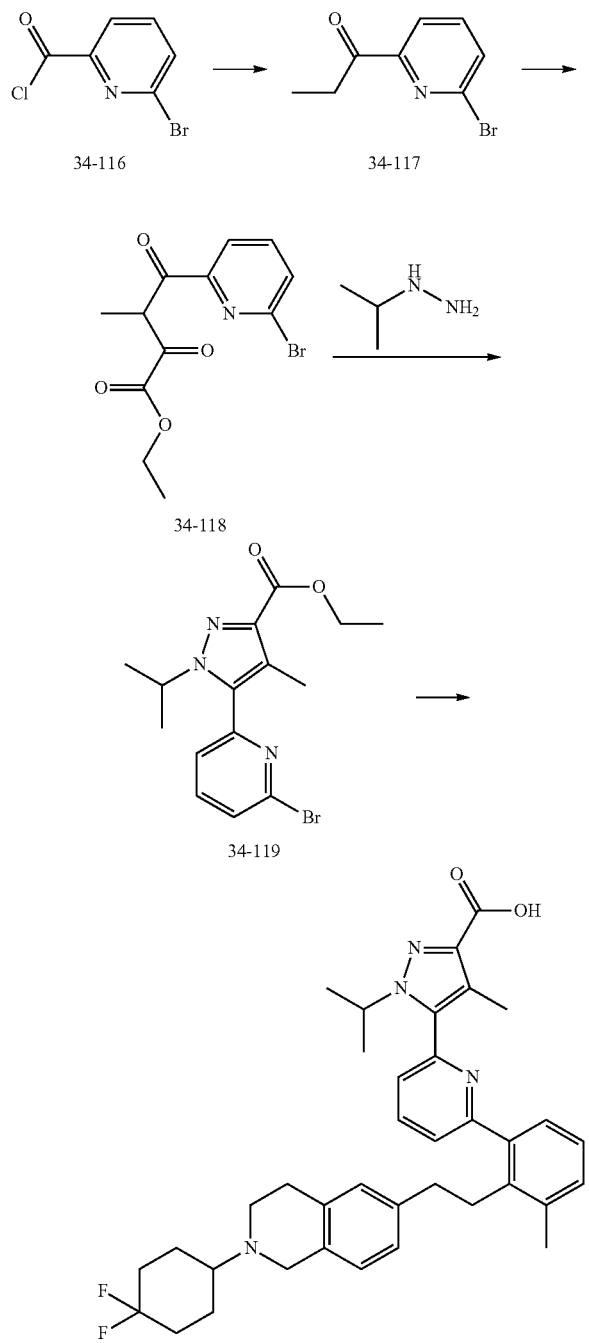

To a solution of bis[2-N,N-dimethylaminoethyl)]ether (12 mL, 63 mmol.) in THF (200 mL) is added ethyl magnesium chloride (31.5 mL, 2M solution in ether) at 0° C. The mixture is stirred at 0° C. for 15 min and then cooled to −78° C. A solution of 6-bromo-pyridine-2-carbonyl chloride (34-116) in THF (100 mL) is added over 15 min. The resulting mixture is stirred at −78° C. for 5 min. and the mixture is immediately quenched with 100 mL of saturated aqueous ammonium chloride solution. The crude reaction mixture is extracted with EtOAc (2×400 mL) and the combined organics are dried over sodium sulfate and concentrated in vacuo to afford crude intermediate 34-117.

To a solution of 34-117 (6.8 g, 31 mmol) in THF (150 mL) at −78° C. is added LiHMDS (38 mL, 1 M in THF). This mixture is stirred for 10 min and then ethyl chlorooxalate (4.77 g, 35 mmol) is added. The reaction is allowed to warm to room temperature over 2 h and then quenched with 100 mL of saturated aqueous ammonium chloride solution. The crude reaction mixture is extracted with EtOAc (2×400 mL), then the combined organics are then dried over sodium sulfate and concentrated in vacuo. The resulting material is purified by column chromatography on silica gel (using a gradient of 3-40% EtOAc:heptanes) to afford intermediate 34-118 (4.9 g).

A solution of 34-118 (300 mg, 0.95 mmol) in EtOH (5 mL) is treated with 0.1 mL of conc. HCl, and then isopropyl hydrazine (71 mg, 0.96 mmol). The reaction is irradiated at 120° C. for 10 min, then cooled to room temperature and added slowly to a stirred solution of 2 M aqueous sodium carbonate. The reaction mixture is extracted with dichloromethane (2×10 mL) and the combined organics are concentrated in vacuo and purified by flash chromatography on silica gel (using a gradient of 5-50% EtOAc:heptanes) to afford intermediate 34-119 (154 mg).

The title compound 88 is prepared from intermediate 34-119 according to the procedure described in Example 31. MS, electrospray, m/z=615.4 [M+H], rt 0.79 min.

The following compounds from Table 1 are prepared from intermediate 34-118 and the appropriate hydrazine according to the procedure outlined in Example 34.

Compound 82: MS, electrospray, m/z=567.2 [M+H], rt 0.68 min)

Compound 83: MS, electrospray, m/z=581.2 [M+H], rt 0.70 min)

Compound 84: MS, electrospray, m/z=595.2 [M+H], rt 0.71 min)

Compound 85: MS, electrospray, m/z=611.3 [M+H], rt 0.63 min)

Compound 87: MS, electrospray, m/z=621.1 [M+H], rt 0.71 min)

Compound 89: MS, electrospray, m/z=623.4 [M+H], rt 0.71 min)

Compound 90: MS, electrospray, m/z=613.4 [M+H], rt 0.78 min)

Compound 91: MS, electrospray, m/z=579.4 [M+H], rt 0.70 min)

Example 35

Preparation of 4-methyl-5-[6-[3-methyl-2-[(2-tetrahydropyran-4-yl-3,4-dihydro-1H-isoquinolin-6-yl)methoxy]phenyl]-2-pyridyl]isoxazole-3-carboxylic acid (Compound 86, Table 1)

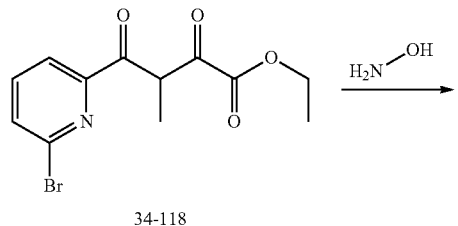

34-118

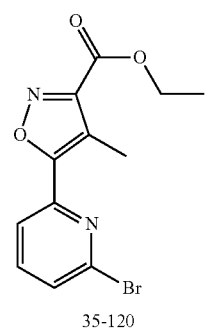

35-120

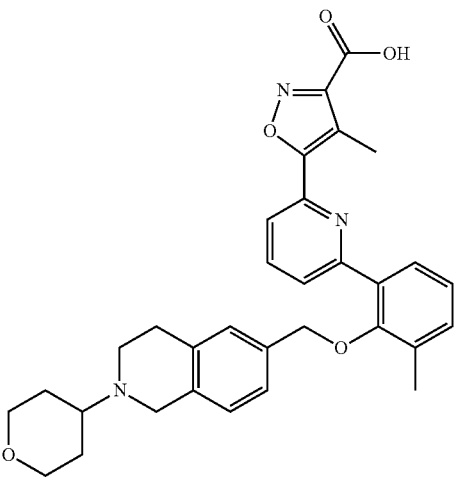

86

Intermediate 34-118 (300 mg, 0.96 mmol) is dissolved in EtOH (5 mL) and treated with 0.1 mL of conc. HCl. Hydroxylamine hydrochloride (32 mg, 0.96 mmol) is added, and the reaction is irradiated at 120° C. for 10 min. The mixture is cooled to room temperature and then added slowly to a stirred solution of 2 M sodium carbonate. The organic layer is extracted with DCM and concentrated in vacuo. The resulting material is purified by flash chromatography on silica gel (using a gradient of 5-50% EtOAc:heptanes) to afford intermediate 35-120 (127 mg).

The title compound 86 is prepared from 35-120 according to the procedure described in Example 31. MS, electrospray, m/z=540.4 [M+H], rt 0.72 min.

Example 36

Preparation of intermediate (2,7-dimethyl-3,4-dihydro-1H-isoquinolin-6-yl)methanol (36-122)

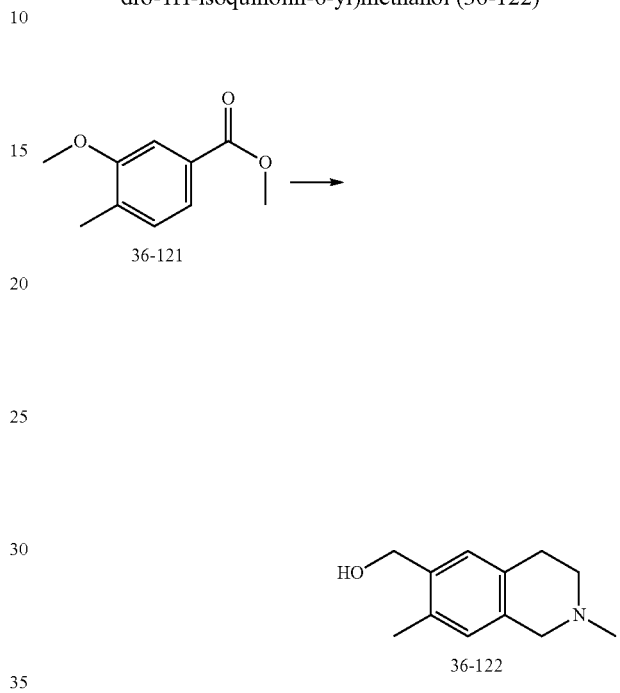

Intermediate 36-122 is prepared from ester 36-121 according to the procedure outlined in Example 11.

Example 37

Preparation of 1-[6-[2-[(2,7-dimethyl-3,4-dihydro-1H-isoquinolin-6-yl)methoxy]-5-methylphenyl]-2-pyridyl]-5-(trifluoromethyl)pyrazole-4-carboxylic acid (Compound 62, Table 1)

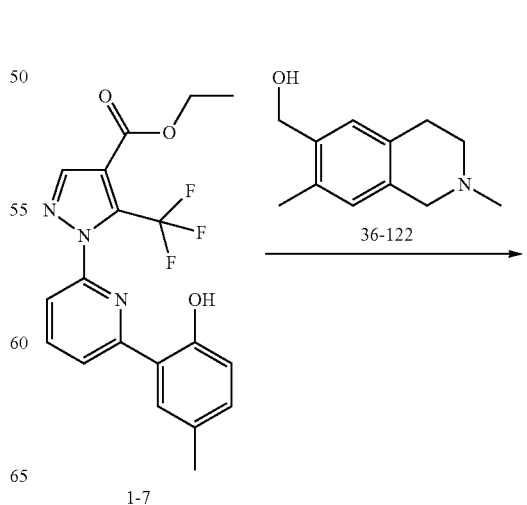

1-7

-continued

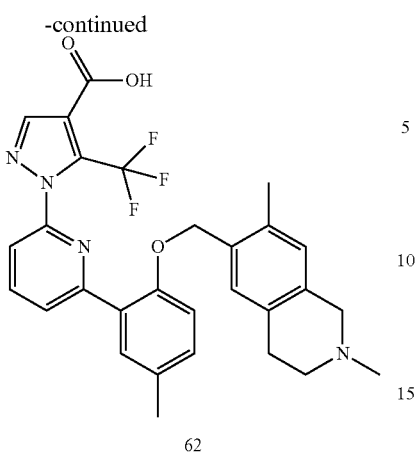

62

The title compound is prepared from intermediates 1-7 and 36-122 according to the procedure outlined in Example 12. MS, electrospray, m/z=537.3 [M−H], rt 0.72 min.

Assessment of Biological Activity

Molecular Assay

The compounds of the invention may be evaluated in the following molecular assay:

Recombinant human soluble guanylate cyclase (sGC) is purified from Sf9 insect cells coinfected with baculoviruses expressing the alpha 1 or beta 1 subunit of sGC, both with a C-terminal histidine tag. Heme-free sGC is prepared by treating cell lysate with a final concentration of 0.5% Tween 20 prior to purification on a nickel affinity column.

sGC catalyzes the conversion of guanosine-5'-triphosphate (GTP) to cyclic guanosine monophosphate (cGMP). The activity of sGC is measured in vitro using the commercially available CisBio cGMP detection kit (catalog #62GM2PEB) in a 384 well format. In brief, 300 pM heme-free sGC is incubated in reaction buffer (50 mM MOPS pH 6.8, 0.2 N KOH, 50 mM NaCl, 2 mM $MgCl_2$, 0.1% BSA, 1.25 mM IBMX, 0.25 mM TCEP, 50 nM GTP) in the presence or absence of dilutions of test compounds diluted in DMSO (final concentration of 1%) in a volume of 10 microL at 37° C. for 60 minutes. Undiluted reaction products or an 80-fold dilution of reaction products (10 microL of either) prepared in reaction buffer containing 0.2 mM TCEP and 10 mM EDTA is mixed with 5 microL of d2-cGMP plus 5 microL of $Eu^{3+}$ cryptate-labeled anti-cGMP, each diluted in buffer containing 0.1 M $KPO_4$ pH 7.5, 0.4 M KF, 20 mM EDTA, 0.2% BSA. After a one hour incubation at room temperature in the dark, the mixtures are quantified on an EnVision plate reader (PerkinElmer) according to manufacturer instructions (laser excitation 337 nm, emission 620 and 665 nm). The ratio at each compound concentration is converted to nM cGMP using the linear portion of a calibration curve. Log compound concentration is plotted against combined undiluted and diluted nM cGMP values to determine the $EC_{50}$ for each curve.

Representative compounds of the present invention were tested for activity in the above assay. Preferred compounds have an $IC_{50}$<5,000 nM and more preferred compounds have an $IC_{50}$<100 nM in this assay. As examples, data for representative compounds from Table 1 are shown in Table 2.

TABLE 2

| Cpd No. | $EC_{50}$ (nM) |
| --- | --- |
| 1 | 148 |
| 2 | 46 |
| 3 | 27 |
| 4 | 575 |
| 5 | 33 |
| 6 | 78 |
| 7 | 490 |
| 8 | 280 |
| 9 | 67 |
| 10 | 280 |
| 12 | 19 |
| 13 | 79 |
| 14 | 11 |
| 16 | 33 |
| 17 | 13 |
| 18 | 0.8 |
| 19 | 2 |
| 20 | 4 |
| 21 | 25 |
| 22 | 1 |
| 23 | 2 |
| 24 | 9 |
| 25 | 19 |
| 26 | 3 |
| 27 | 6 |
| 28 | 9 |
| 29 | 0.5 |
| 30 | 71 |
| 31 | 2 |
| 32 | 12 |
| 33 | 6 |
| 34 | 8 |
| 35 | 7 |
| 37 | 198 |
| 38 | 46 |
| 40 | 32 |
| 41 | 4537 |
| 43 | 1700 |
| 46 | 1998 |
| 48 | 640 |
| 50 | 380 |
| 51 | 340 |
| 52 | 550 |
| 53 | 47 |
| 54 | 165 |
| 55 | 44 |
| 56 | 31 |
| 57 | 1100 |
| 58 | 2600 |
| 59 | 4200 |
| 60 | 19 |
| 61 | 75 |
| 62 | 440 |
| 63 | 14 |
| 64 | 21 |
| 65 | 134 |
| 66 | 1830 |
| 67 | 234 |
| 68 | 180 |
| 69 | 8 |
| 70 | 37 |
| 71 | 159 |
| 72 | 27 |
| 73 | 47 |
| 74 | 27 |
| 75 | 175 |
| 76 | 100 |
| 77 | 20 |
| 78 | 970 |
| 79 | 1200 |
| 80 | 155 |
| 81 | 185 |
| 82 | 210 |
| 83 | 50 |
| 84 | 69 |
| 85 | 94 |
| 86 | 775 |
| 87 | 180 |

TABLE 2-continued

| Cpd No. | EC$_{50}$ (nM) |
|---|---|
| 88 | 3 |
| 89 | 700 |
| 90 | 15 |
| 91 | 160 |

Assessment of Solubility

Solubility is measured by the following method.
1. Sample preparation:
DMSO stock samples at 10 mM conc are prepared. 100 ul of 95 compds+1 DMSO (blank) are prepared in a 96 Remp tube plate for HT solubility analysis (2×95 plates). The samples are pierced and 100 ul of thawed samples are transferred into the PCR plate for analysis. Each sample is run in duplicate at each pH (pH 4.5 and 7.4). Up to 95 samples can be run in replicate at 2 pH's+1 DMSO (blank).
2. Preparation of pH 4.5 and 7.4 buffers:
pH 4.5 buffer: To 12.5 of system solution (pION) qs to 500 mL of distilled water (pH 2.85-2.90); adjust the pH to pH 4.5 with 0.5 N NaOH.
pH 7.4 buffer: To 12.5 of system solution (pION) qs to 500 mL of distilled water (pH 2.85-2.90); adjust the pH to pH 7.4 with 0.5N NaOH.
3. Procedure:
Preparation of UV blank plate:
75 ul of buffer (pH 7.4 or pH 4.5) is added to UV plate followed by addition of 70 ul of N-propanol. The solution is mixed and the blank spectrum is read using spectrophotometer.
Preparation of Reference UV plate:
10 ul of each stock sample (including DMSO control) is added to 190 ul of N-propanol to prepare the reference stock plate. Reference stock samples are mixed and 5 ul of each stock sample is added to UV blank plate after it is read spectrophotometrically. The reference stock sample is mixed with blank solution in UV plate and the reference spectrum is read using UV spectrophotometer.
Preparation of sample for incubation:
Solubility at pH 7.4: 6 ul of each stock sample (including DMSO control) is added to the storage plate containing 600 ul of pH 7.4 buffer, mixed and incubated for 16-19 hours. The plate is sealed well during the incubation process. The DMSO content in the sample is 1.0%. The concn in deep well plates is 100 uM
Solubility at pH 4.5:
6 ul of each stock sample (including DMSO control) is added to the deep well plate containing 600 ul of pH 4.5 buffer, mixed and incubated for 16-19 hours. The plate is sealed well during the incubation process. The DMSO content in the sample is 1.0%. The concn in deep well plates is 100 uM
Preparation of sample UV plate:
At the end of the incubation period, 100 uL of sample from the storage plate is vacuum filtered using a filter plate. This step wets the filters and the filtrate is discarded. Another 200 ul of the sample from the deep well plate is vacuum filtered using the same filter block but a clean filter plate. 75 ul of the filtrate from the filter plate is transferred to a UV sample plate. 75 ul of N-propanol is added to this UV plate. The solution is mixed and the spectrum is read using the UV spectrophotometer.

Data Analysis:
The spectra collected for blank, reference and sample from 250-498 nm is analyzed using pION software. If the sample precipitates out, the solubility is reported as XX µg/ml. If there is no precipitation and the sample is soluble, solubility is reported as >40 µg/mL (YY being the initial concentration of the compound in the sample).

Solubility data (µg/mL) for compounds from Table 1 is shown in the table below.

| Cpd No. | Sol pH 7.4 | Sol pH 4.5 |
|---|---|---|
| 1 | >62 | >62 |
| 2 | 6.1 | 6.5 |
| 3 | >65 | 0.8 |
| 4 | 21.7 | 17.6 |
| 5 | >58 | 0.1 |
| 6 | >54 | 0.5 |
| 7 | >51 | 2.1 |
| 8 | >53 | 6.9 |
| 9 | >54 | 0.4 |
| 10 | >50 | 0.95 |
| 12 | >54 | >54 |
| 13 | >52 | 8.1 |
| 14 | 44.4 | >79 |
| 16 | >67 | >67 |
| 17 | >68 | 44.3 |
| 18 | >59 | >59 |
| 19 | >58 | >58 |
| 20 | 10.7 | 7.8 |
| 21 | >55 | >55 |
| 22 | >59 | >59 |
| 23 | >59 | >59 |
| 24 | >59 | 40.0 |
| 25 | >62 | >62 |
| 26 | >60 | >60 |
| 27 | 25.6 | 18.2 |
| 28 | >61 | >61 |
| 29 | >61 | 12.9 |
| 30 | >60 | >60 |
| 31 | >60 | 22.0 |
| 32 | 15.9 | 10.8 |
| 33 | 4.6 | 6.3 |
| 34 | 41.8 | 41.5 |
| 35 | 43.0 | 42.3 |
| 37 | 27.4 | 14.1 |
| 38 | 18.4 | 15.5 |
| 40 | 18.5 | 16.3 |
| 41 | 11.8 | >58 |
| 43 | 19.6 | 15.4 |
| 46 | 5.7 | 0.1 |
| 48 | 1.9 | 5.1 |
| 50 | 13.4 | 13.7 |
| 51 | 35.9 | 44.7 |
| 52 | 42.1 | >63 |
| 53 | 51.4 | 40.1 |
| 54 | 32.6 | >76 |
| 55 | >63 | >63 |
| 56 | >65 | >65 |
| 57 | >78 | >78 |
| 58 | >78 | >78 |
| 59 | >110 | >110 |
| 60 | >64 | >64 |
| 61 | >110 | >110 |
| 62 | 1.2 | 2.8 |
| 63 | 54.2 | >78 |
| 64 | >78 | >78 |
| 65 | >53 | >53 |
| 66 | >53 | >53 |
| 67 | 54.2 | >78 |
| 70 | >66 | >66 |
| 71 | >67 | >67 |
| 72 | >67 | >67 |
| 73 | >67 | >67 |
| 74 | >66 | >66 |

-continued

| Cpd No. | Sol pH 7.4 | Sol pH 4.5 |
|---|---|---|
| 73 | >66 | >66 |
| 74 | >68 | >68 |
| 75 | >65 | >65 |
| 76 | >66 | >66 |
| 77 | 26.9 | 40.1 |
| 78 | 24.2 | 24.1 |
| 79 | >80 | >80 |
| 80 | >81 | >81 |
| 81 | 31.7 | 48.4 |
| 82 | >67 | >67 |
| 83 | >69 | >69 |
| 84 | >70 | >70 |
| 85 | >60 | >60 |
| 86 | >65 | >65 |
| 87 | 14.1 | 17.3 |
| 88 | >61 | 51.2 |
| 89 | >62 | 51.5 |
| 90 | 50.2 | 49.0 |
| 91 | >69 | >69 |

Methods of Therapeutic Use

The compounds disclosed herein effectively activate soluble guanylate cyclase. The activation or potentiation of soluble guanylate cyclase is an attractive means for preventing and treating a variety of diseases or conditions associated with deficient sGC activation. Thus, in one embodiment of the invention, there are provided methods of treating diseases that can be alleviated by sGC activation or potentiation. These include:

Cardiovascular and related diseases including hypertension, atherosclerosis, peripheral artery disease, restenosis, stroke, heart failure, coronary vasospasm, cerebral vasospasm, ischemia/reperfusion injury, thromboembolic pulmonary hypertension, pulmonary arterial hypertension, stable and unstable angina and thromboembolic disorders;

Inflammatory diseases including psoriasis, multiple sclerosis, arthritis, asthma, and chronic obstructive pulmonary disease;

Hepatic fibrotic disorders including but not limited to cirrhosis of any etiology or fibrosis of specific areas of the liver such as periportal fibrosis which may be caused by immunologic injury, hemodynamic effects and/or other causes;

Renal fibrotic disorders including but not limited to glomerulosclerosis, focal glomerulosclerosis, mesangial fibrosis, interstitial fibrosis due to immunologic injury, hemodynamic effects, diabetes (types 1 and 2), IgA nephropathy, lupus nephropathy, membranous nephropathy, hypertension, hemolytic uremic syndrome, multiple glomerulonephritides, interstitial nephritis, tubulointerstitial nephritis again of immunologic and non-immunologic causes;

Pulmonary fibrotic disorders, both diffuse and localized, due to immunologic and non-immunologic causes, including but not limited to idiopathic pulmonary fibrosis, pulmonary fibrosis due to exposure to toxins, chemicals, drugs, and cystic fibrosis;

Cardiac fibrotic disorders due to immunologic and non-immunologic causes including ischemic heart disease (coronary artery disease) and transient and/or sustained decreased blood flow in one or more coronary vessels including possibly related to interventions on coronary arteries or veins, associated with cardiac surgery and/or the use of cardiopulmonary bypass procedures and myocarditis due to viral and non-viral causes, as well as immunologically related myocardial injury potentially due to cross-reactivity to other antigens to which the human body is exposed;

Other diseases mediated at least partially by diminished or decreased soluble guanylate cyclase activity, such as renal disease, diabetes, urologic disorders including overactive bladder, benign prostatic hyperplasia, and erectile dysfunction, and neurological disorders including Alzheimer's disease, Parkinson's disease and neuropathic pain.

These disorders have been well characterized in man, but also exist with a similar etiology in other mammals, and can be treated by pharmaceutical compositions of the present invention.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:

1. A compound of the formula I
wherein:

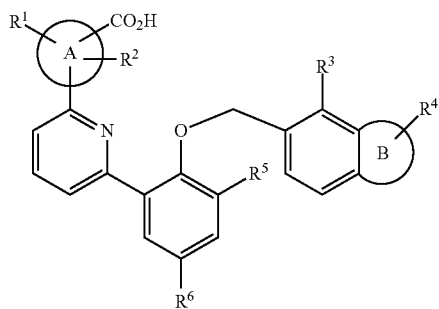

A is a 5- or 6-membered aryl, heteroaryl or heterocyclyl group;

B is a 5-7 membered heterocyclyl group containing one nitrogen, wherein one carbon of the heterocyclyl group is optionally substituted with an oxo group, or B is a 5-membered heteroaryl group containing at least 2 nitrogens;

$R^1$ and $R^2$ are independently selected from H, $C_{1-4}$alkyl, $C_{3-6}$cycloalkyl, tetrahydropyranyl, —$CF_3$, —$CH_2CF_3$ and —$CH_2CH_2CO_2H$;

$R^3$ is selected from H and —$CH_3$;

$R^4$ is selected from H, $C_{1-6}$alkyl, $C_{3-7}$cycloalkyl, —C(O)$C_{1-6}$alkyl, —$CH_2CF_3$, —$SO_2C_{1-6}$alkyl, —$SO_2(CH_2)_{1-3}$$CO_2H$, —$CO_2C_{1-4}$alkyl, heterocyclyl, aryl, heteroaryl, —($C_{0-2}$alkyl)heterocyclyl, —($C_{1-2}$alkyl)aryl and —($C_{1-2}$alkyl)heteroaryl, wherein said heterocyclyl is selected from tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl, and said heterocyclyl, cycloalkyl, aryl and heteroaryl are optionally substituted with one to two groups independently selected from $C_{1-3}$alkyl, —$CF_3$, and halogen, or $R^4$ is optionally not present when B is a heteroaryl group;

$R^5$ is selected from H, —$C_{1-3}$alkyl, —$OCH_3$, —$CF_3$, —CN and Cl; and $R^6$ is selected from H and $CH_3$;

provided that $R^5$ and $R^6$ are not both H;

or a salt thereof.

2. The compound according to claim 1 wherein

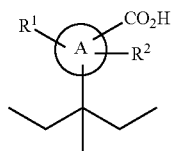

is a 5- or 6-membered aryl, heteroaryl or heterocyclyl group selected from:

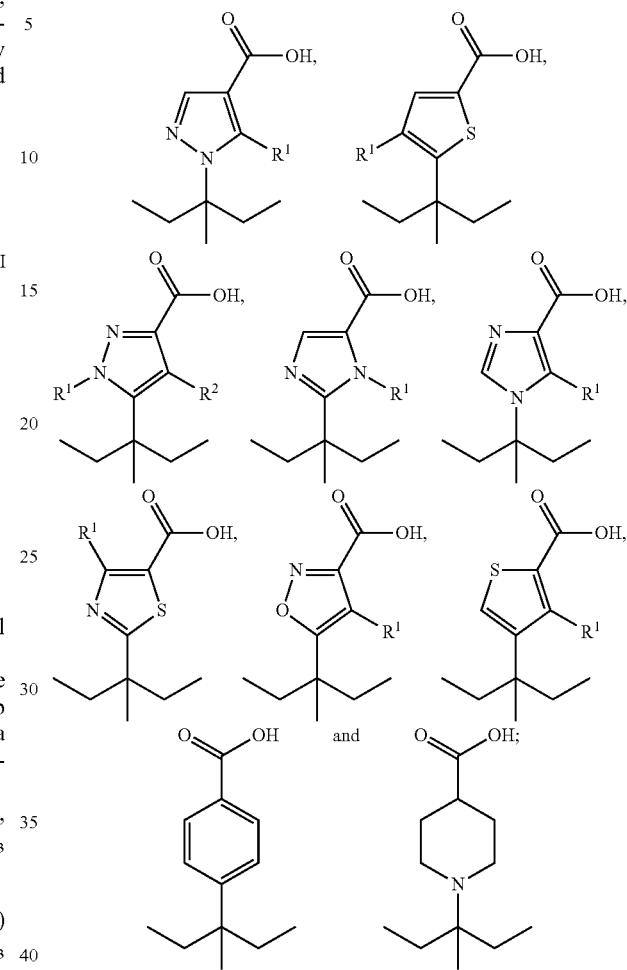

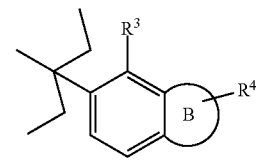

is selected from:

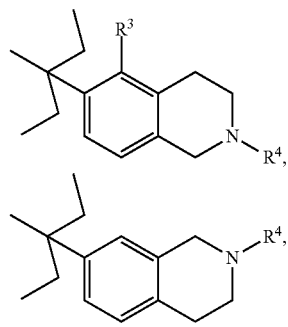

-continued

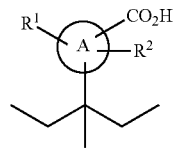,

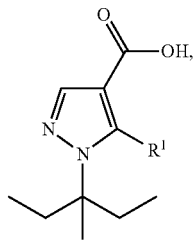,

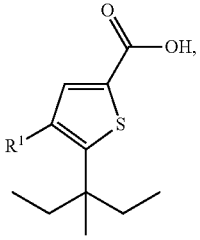,

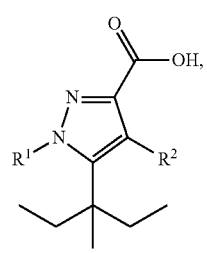,

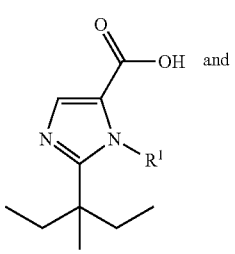 and

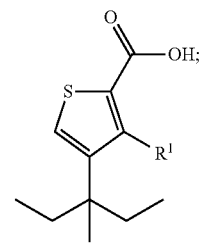;

R$^1$ and R$^2$ are independently selected from H, C$_{1-4}$alkyl, cyclopropyl and —CF$_3$;

R$^4$ is selected from H, C$_{1-6}$alkyl, C$_{3-7}$cycloalkyl, —C(O)C$_{1-6}$alkyl, —CH$_2$CF$_3$, —SO$_2$C$_{1-6}$alkyl, —SO$_2$(CH$_2$)$_{1-3}$CO$_2$H, —CO$_2$C$_{1-4}$alkyl, heterocyclyl, phenyl, heteroaryl, —(C$_{0-2}$alkyl)heterocyclyl, —(C$_{1-2}$alkyl)phenyl and —(C$_{1-2}$alkyl)heteroaryl, wherein said heterocyclyl is selected from tetrahydrofuranyl and tetrahydropyranyl, and said heteroaryl is selected from imidazolyl, oxazolyl, pyrazinyl, pyrazolyl, pyridinyl, pyrimidinyl, thiazolyl and 4,5,6,7-tetrahydrobenzothiazolyl, and wherein said heterocyclyl, cycloalkyl, phenyl and heteroaryl are optionally substituted with one to two groups independently selected from methyl, ethyl, —CF$_3$ and fluorine;

R$_5$ is selected from H, —CH$_3$, —CH$_2$CH$_3$, —OCH$_3$, and —CF$_3$; and

R$_6$ is selected from H and —CH$_3$;

provided that R$_5$ and R$_6$ are not both H;

or a salt thereof.

3. The compound according to claim 2 wherein the group is selected from

,

,

, and

;

or a salt thereof.

4. The compound according to claim 2 wherein the group
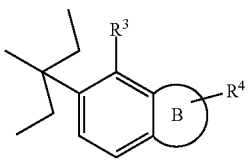
is selected from:
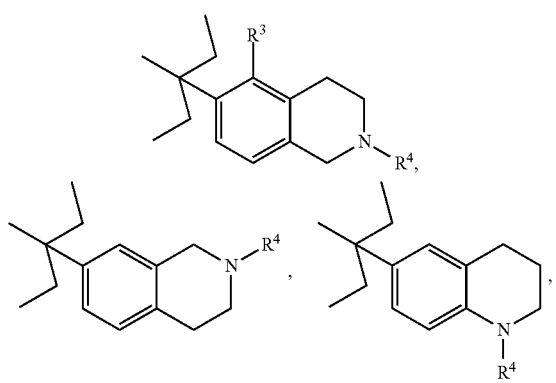
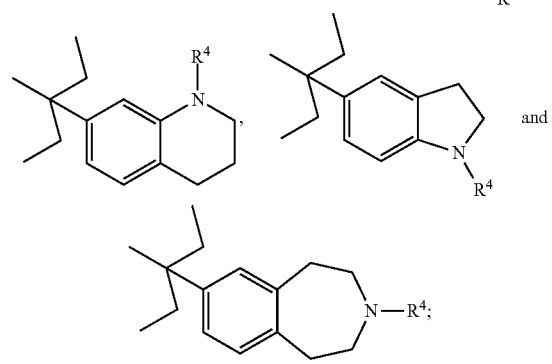
or a salt thereof.
5. The compound according to claim 2 wherein the group
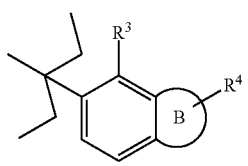
is:
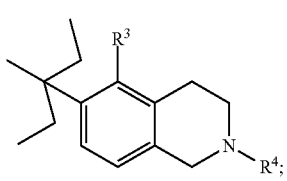
or a salt thereof.
6. The compound according to claim 4 wherein the group
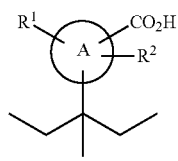
is:
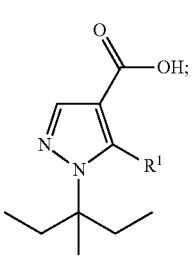
or a salt thereof.
7. The compound according to claim 5 wherein the group
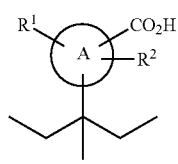
is:
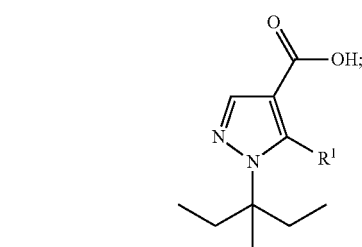
or a salt thereof.
8. The compound according to claim 5 wherein the group
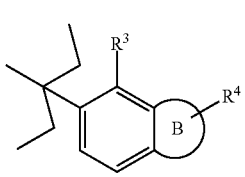

is:
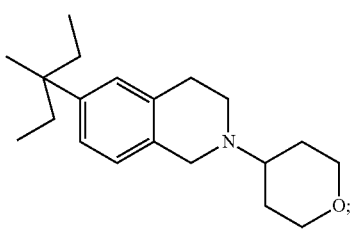
or a salt thereof.
9. A compound selected from the group consisting of
1
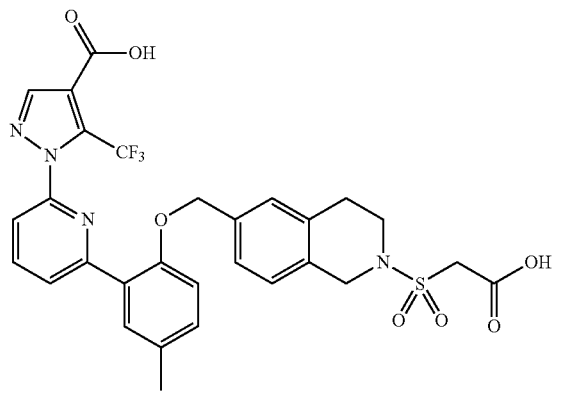
2
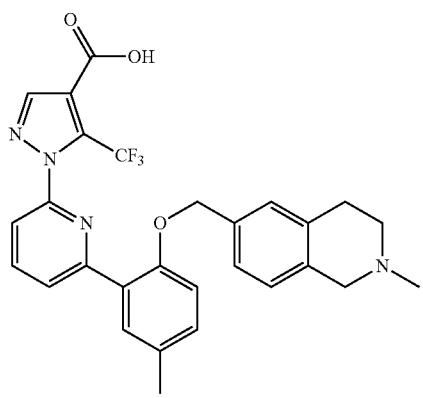
3
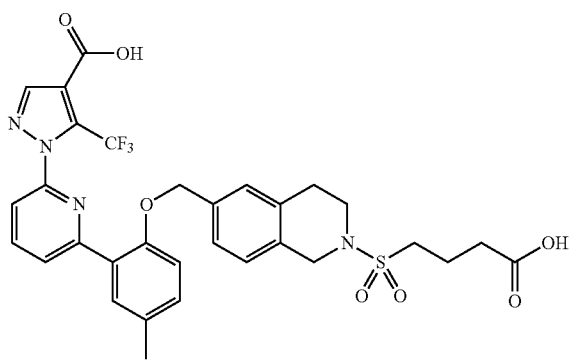
-continued
4
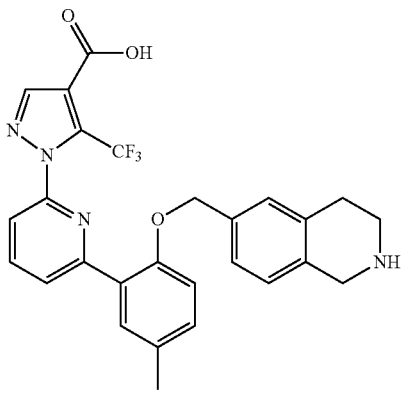
5
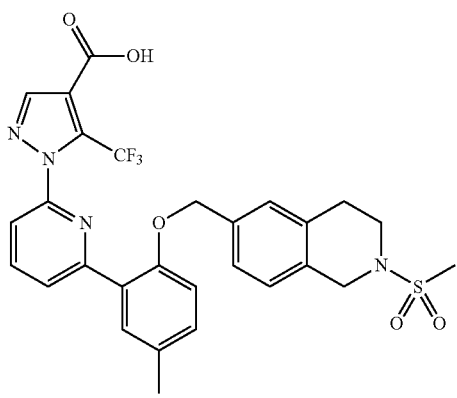
6
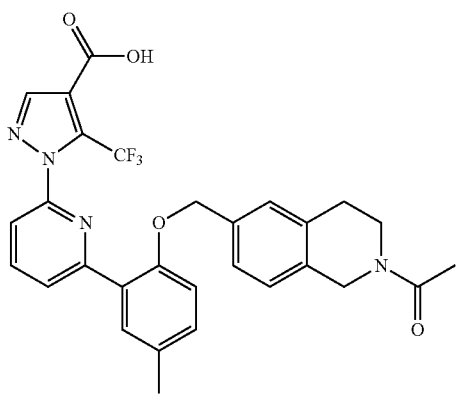
7
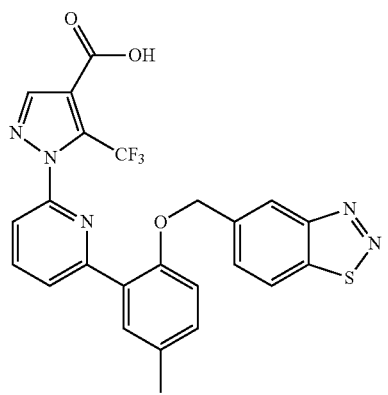

8 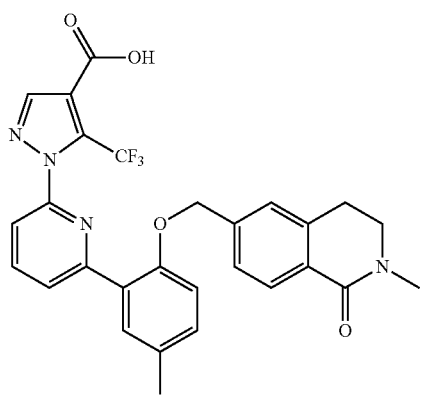
9 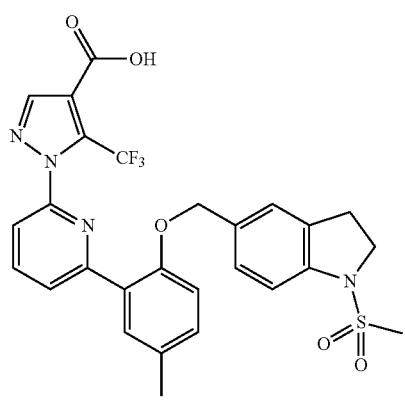 [SMILES: Cc1ccc(OCc2ccc3c(c2)CCN3S(C)(=O)=O)c(-c2cccc(-n3ncc(C(=O)O)c3C(F)(F)F)n2)c1]
10 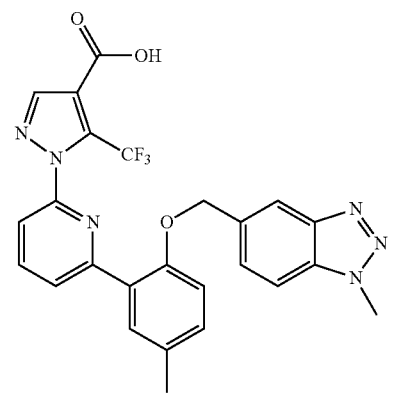 [SMILES: Cc1ccc(OCc2ccc3c(c2)nnn3C)c(-c2cccc(-n3ncc(C(=O)O)c3C(F)(F)F)n2)c1]
11 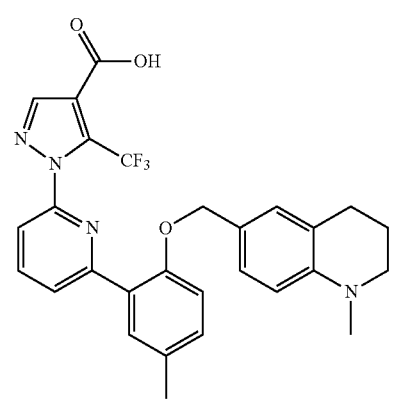 [SMILES: Cc1ccc(OCc2ccc3c(c2)CCCN3C)c(-c2cccc(-n3ncc(C(=O)O)c3C(F)(F)F)n2)c1]
12 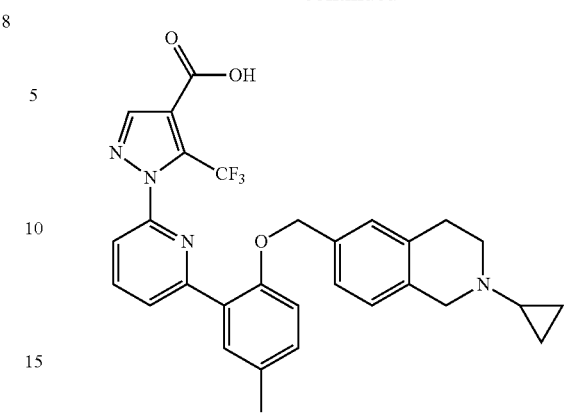
13 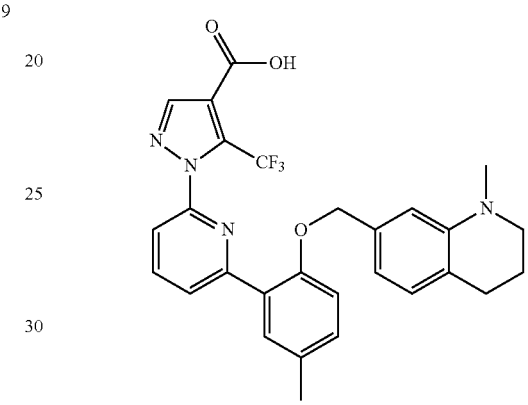
14 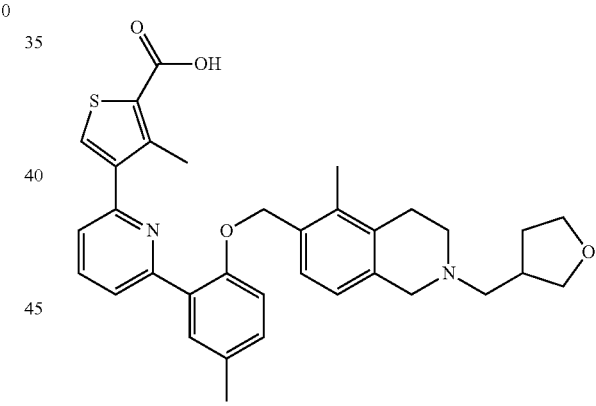
15 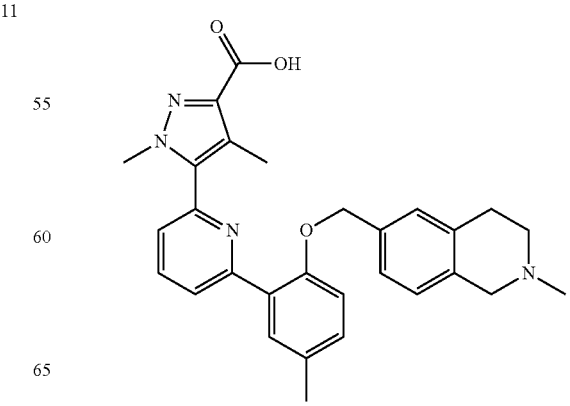

16
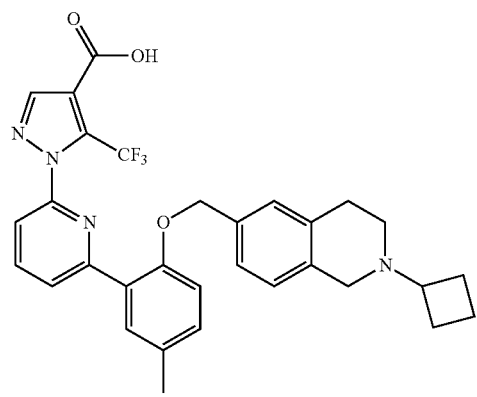 [SMILES: Cc1ccc(OCc2ccc3c(c2)CCN(C2CCC2)C3)c(-c2cccc(-n3ncc(C(=O)O)c3C(F)(F)F)n2)c1]
17
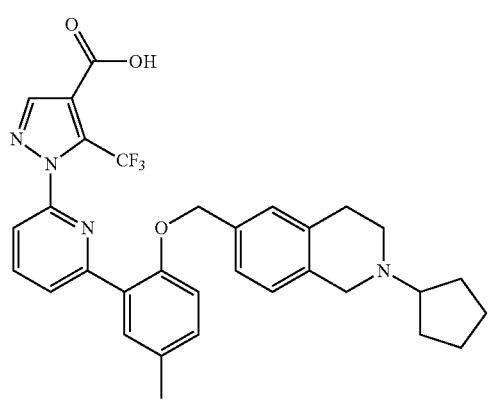 [SMILES: Cc1ccc(OCc2ccc3c(c2)CCN(C2CCCC2)C3)c(-c2cccc(-n3ncc(C(=O)O)c3C(F)(F)F)n2)c1]
18
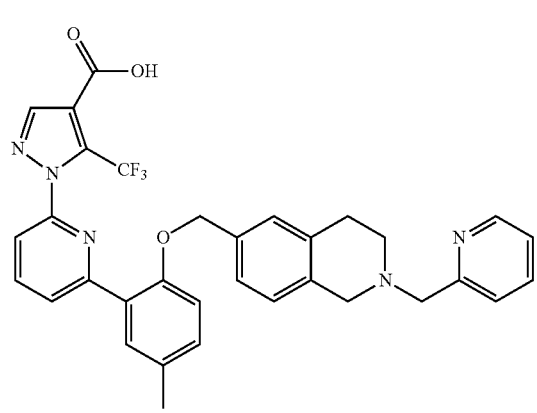 [SMILES: Cc1ccc(OCc2ccc3c(c2)CCN(Cc2ccccn2)C3)c(-c2cccc(-n3ncc(C(=O)O)c3C(F)(F)F)n2)c1]
19
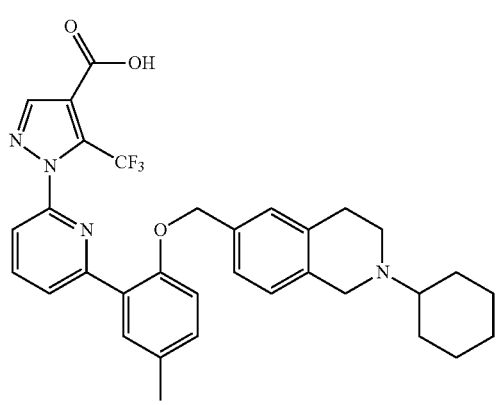 [SMILES: Cc1ccc(OCc2ccc3c(c2)CCN(C2CCCCC2)C3)c(-c2cccc(-n3ncc(C(=O)O)c3C(F)(F)F)n2)c1]
20
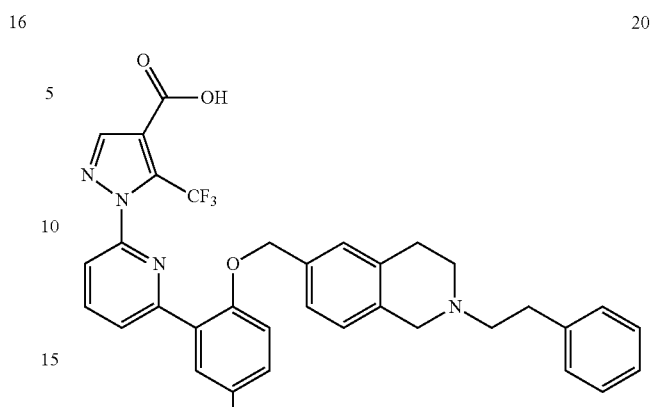
21
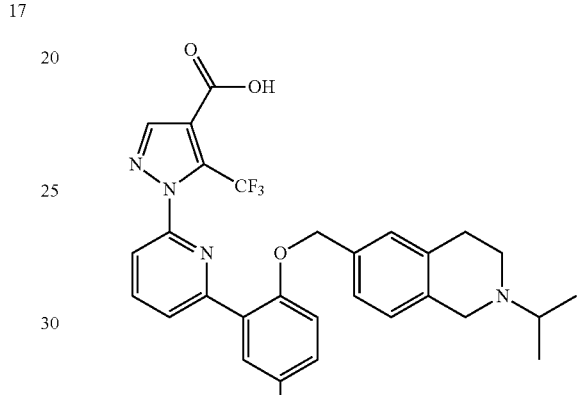
22
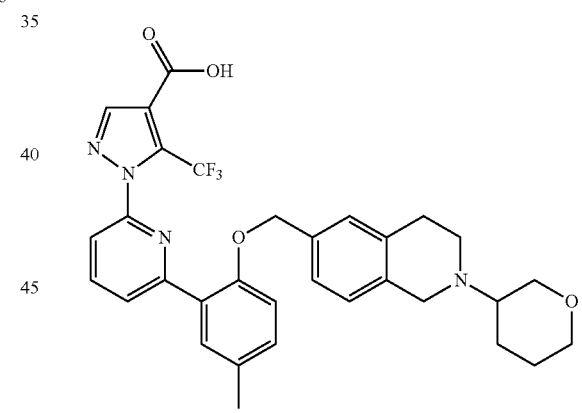
23
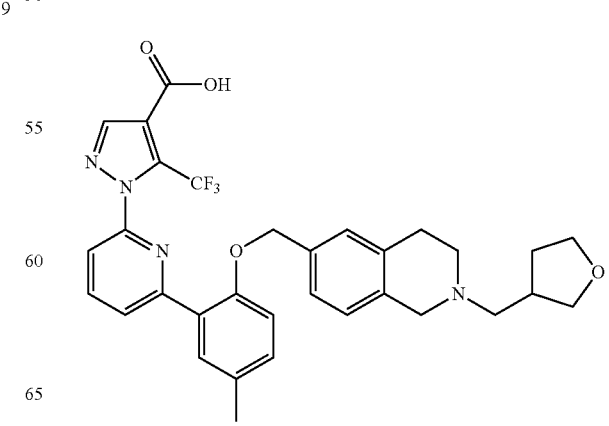

24
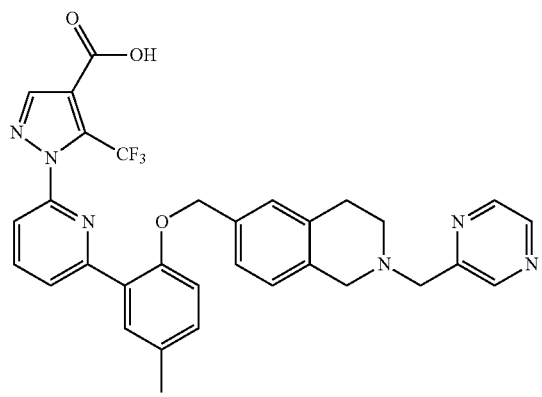 [SMILES: Cc1ccc(OCc2ccc3c(c2)CCN(Cc2cnccn2)C3)c(-c2cccc(-n3ncc(C(=O)O)c3C(F)(F)F)n2)c1]
25
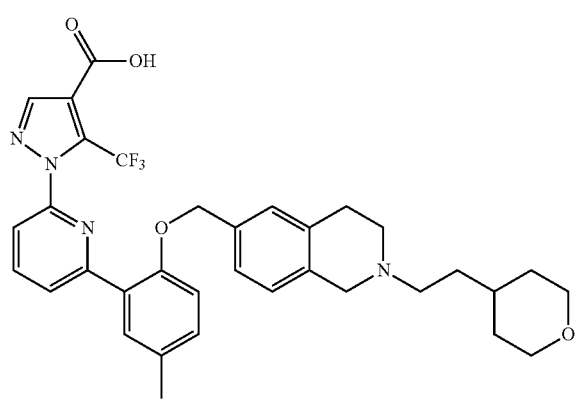 [SMILES: Cc1ccc(OCc2ccc3c(c2)CCN(CCC2CCOCC2)C3)c(-c2cccc(-n3ncc(C(=O)O)c3C(F)(F)F)n2)c1]
26
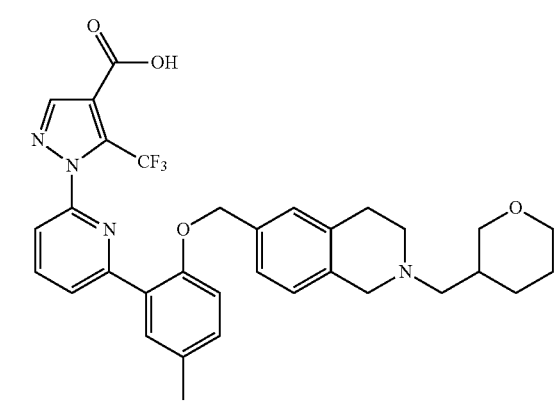 [SMILES: Cc1ccc(OCc2ccc3c(c2)CCN(CC2CCCOC2)C3)c(-c2cccc(-n3ncc(C(=O)O)c3C(F)(F)F)n2)c1]
27
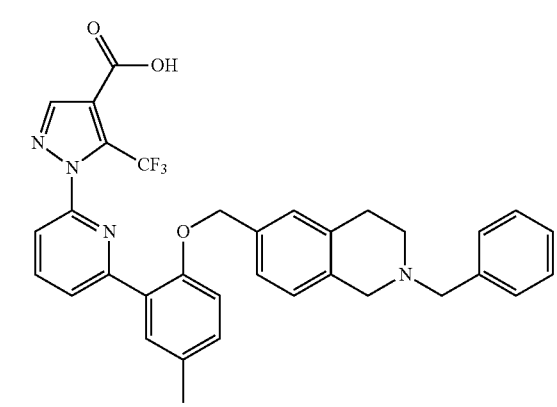 [SMILES: Cc1ccc(OCc2ccc3c(c2)CCN(Cc2ccccc2)C3)c(-c2cccc(-n3ncc(C(=O)O)c3C(F)(F)F)n2)c1]
28
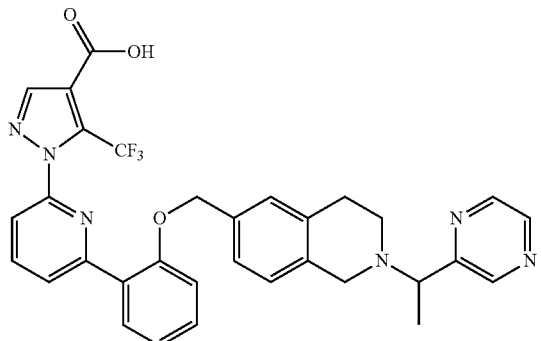
29
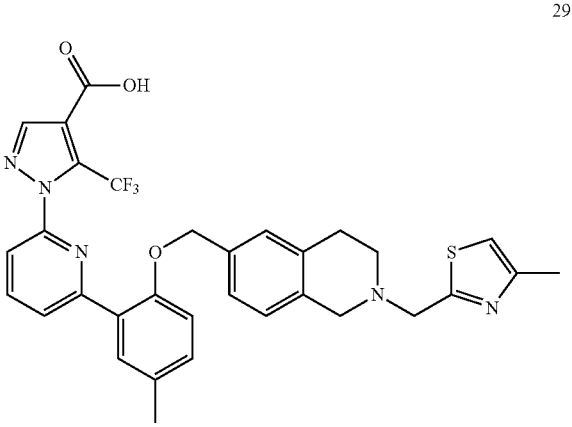
30
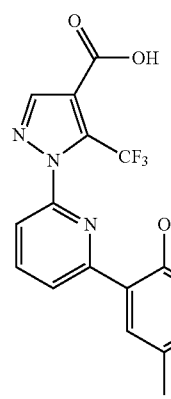
31
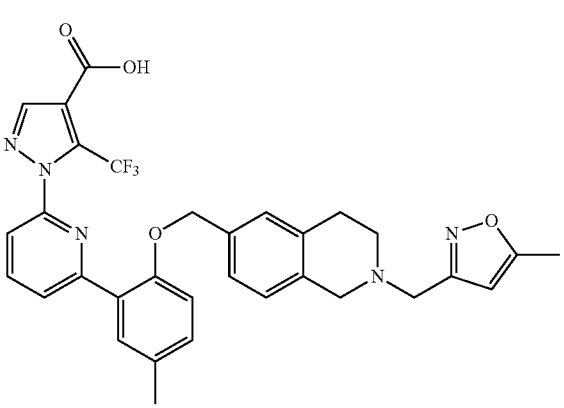 [SMILES: Cc1ccc(OCc2ccc3c(c2)CCN(Cc2cc(C)on2)C3)c(-c2cccc(-n3ncc(C(=O)O)c3C(F)(F)F)n2)c1]

| 32 | 36 |
|---|---|
| 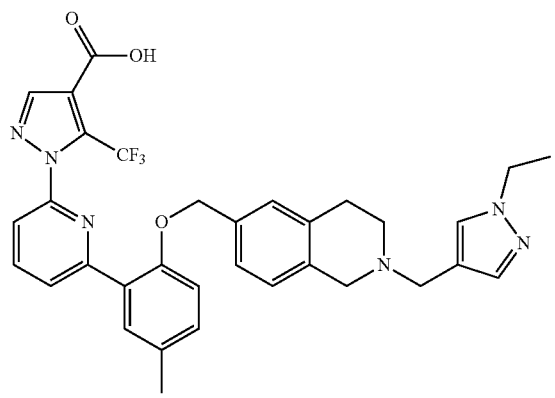 | 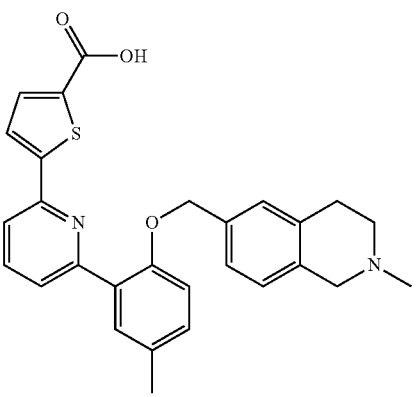 |
| 33 | 37 |
| 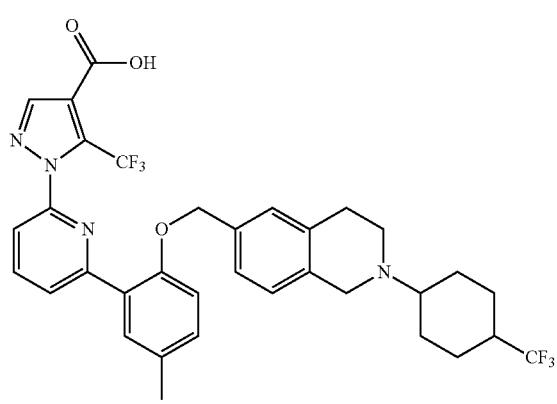 [SMILES: Cc1ccc(OCc2ccc3c(c2)CCN(C2CCC(C(F)(F)F)CC2)C3)c(-c2cccc(-n3ncc(C(=O)O)c3C(F)(F)F)n2)c1] | 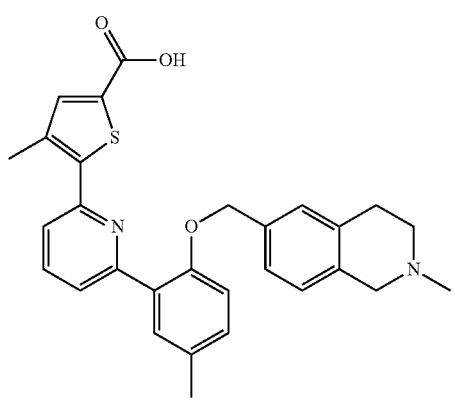 |
| 34 | 38 |
| 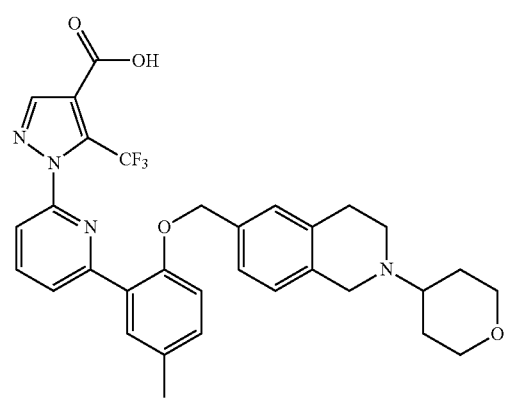 [SMILES: Cc1ccc(OCc2ccc3c(c2)CCN(C2CCOCC2)C3)c(-c2cccc(-n3ncc(C(=O)O)c3C(F)(F)F)n2)c1] | 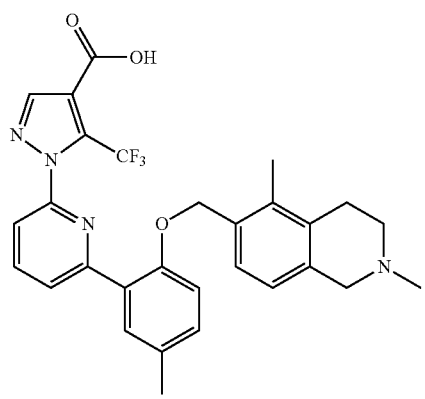 |
| 35 | 39 |
| 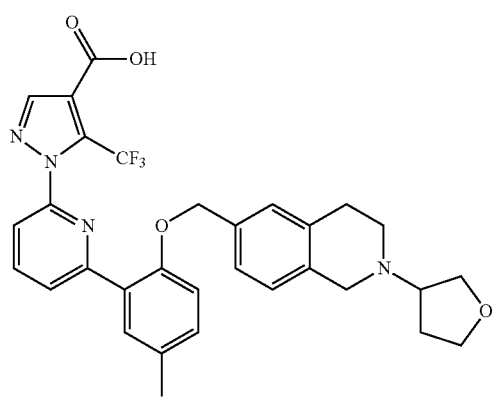 [SMILES: Cc1ccc(OCc2ccc3c(c2)CCN(C2CCOC2)C3)c(-c2cccc(-n3ncc(C(=O)O)c3C(F)(F)F)n2)c1] | 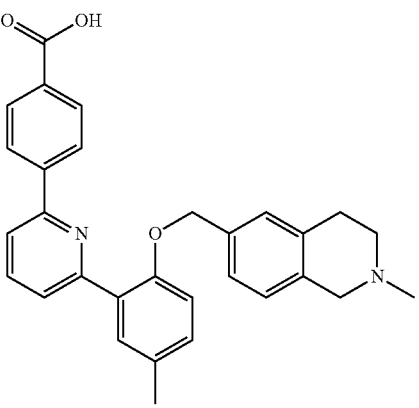 [SMILES: Cc1ccc(OCc2ccc3c(c2)CCN(C)C3)c(-c2cccc(-c3ccc(C(=O)O)cc3)n2)c1] |

40
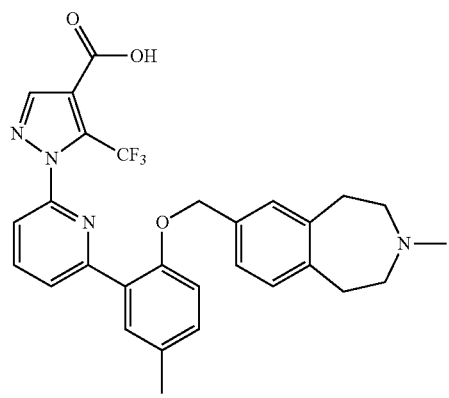 [SMILES: Cc1ccc(OCc2ccc3c(c2)CCN(C)CC3)c(-c2cccc(-n3ncc(C(=O)O)c3C(F)(F)F)n2)c1]
41
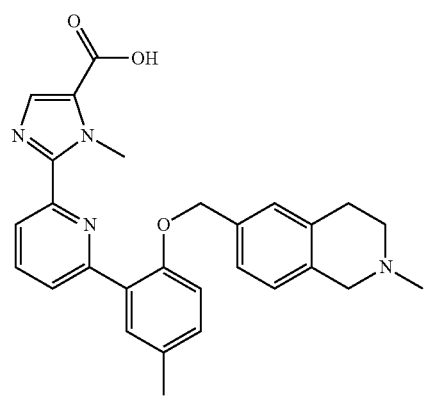 [SMILES: Cc1ccc(OCc2ccc3c(c2)CCN(C)C3)c(-c2cccc(-c3ncc(C(=O)O)n3C)n2)c1]
42
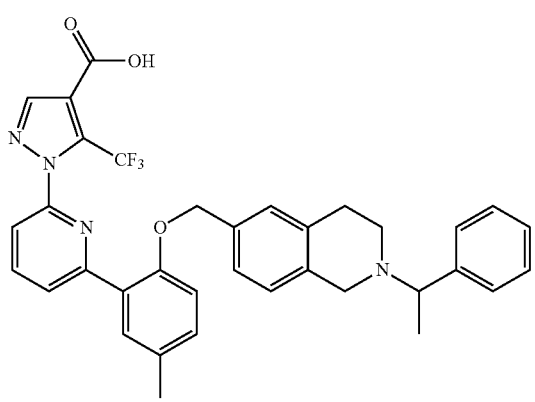 [SMILES: Cc1ccc(OCc2ccc3c(c2)CCN(C(C)c2ccccc2)C3)c(-c2cccc(-n3ncc(C(=O)O)c3C(F)(F)F)n2)c1]
43
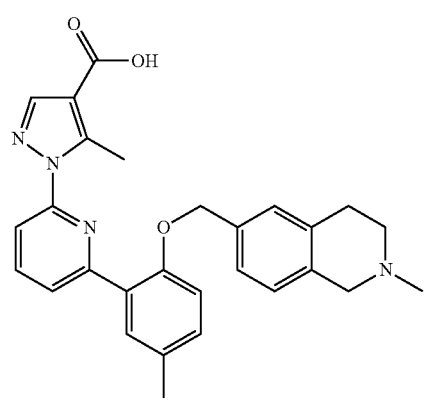 [SMILES: Cc1ccc(OCc2ccc3c(c2)CCN(C)C3)c(-c2cccc(-n3ncc(C(=O)O)c3C)n2)c1]
44
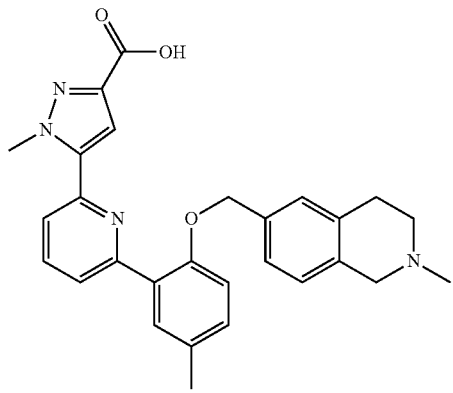
45
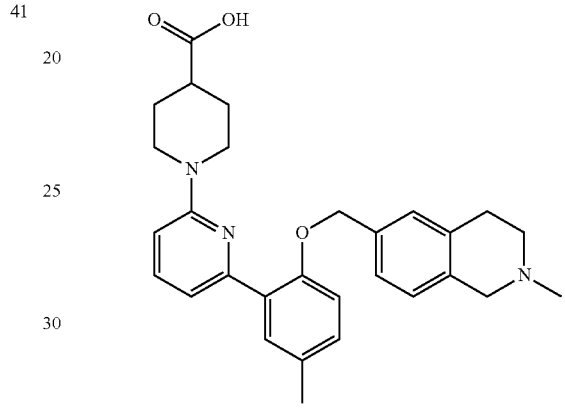
46
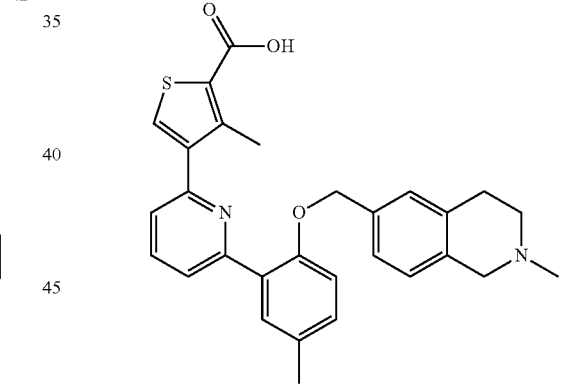
47
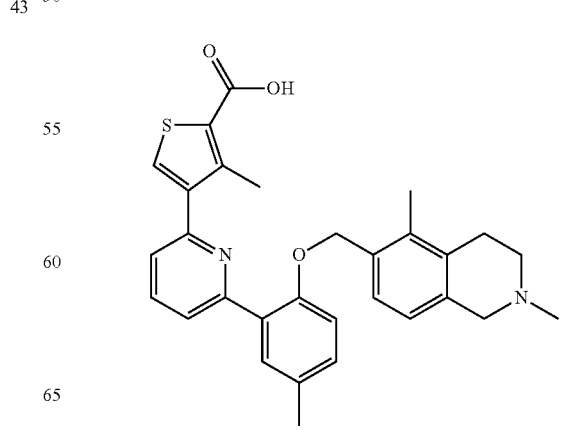

48
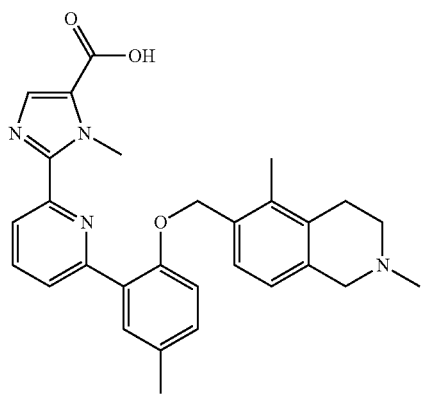 [SMILES: Cc1ccc(OCc2ccc3c(c2C)CCN(C)C3)c(-c2cccc(-c3ncc(C(=O)O)n3C)n2)c1]
49
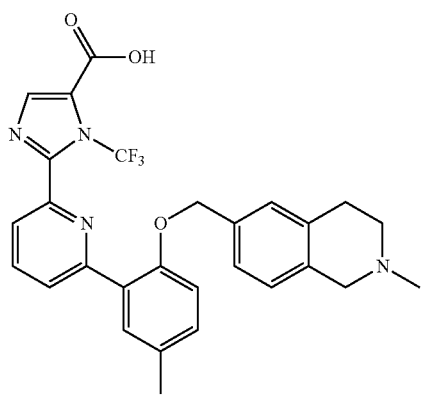 [SMILES: Cc1ccc(OCc2ccc3c(c2)CCN(C)C3)c(-c2cccc(-c3ncc(C(=O)O)n3C(F)(F)F)n2)c1]
50
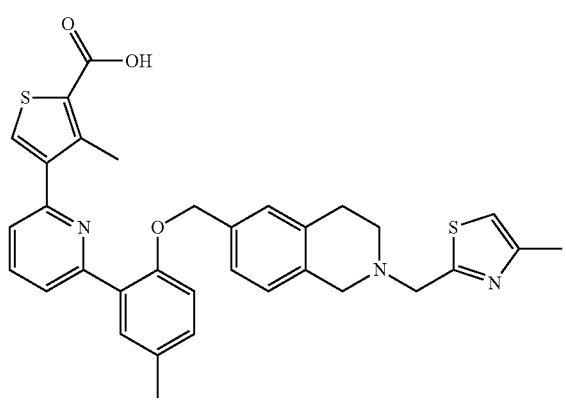 [SMILES: Cc1ccc(OCc2ccc3c(c2)CCN(Cc2nc(C)cs2)C3)c(-c2cccc(-c3csc(C(=O)O)c3C)n2)c1]
51
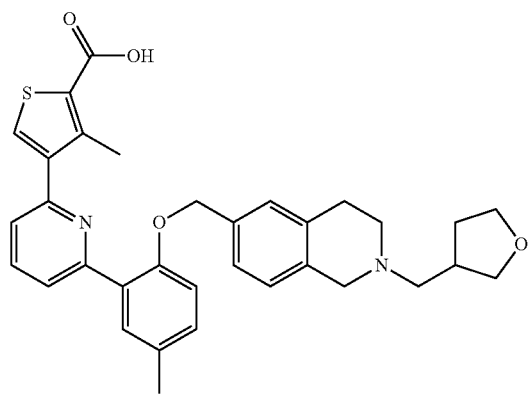 [SMILES: Cc1ccc(OCc2ccc3c(c2)CCN(CC2CCOC2)C3)c(-c2cccc(-c3csc(C(=O)O)c3C)n2)c1]
52
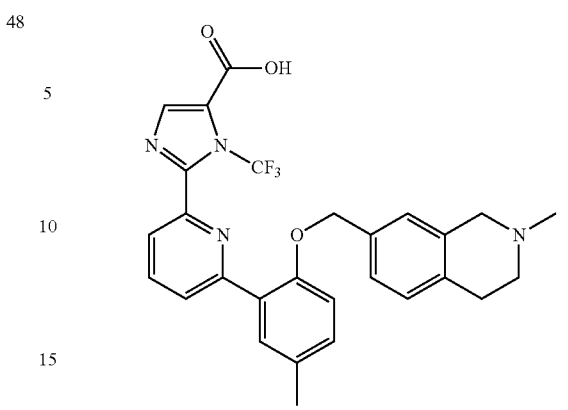
53
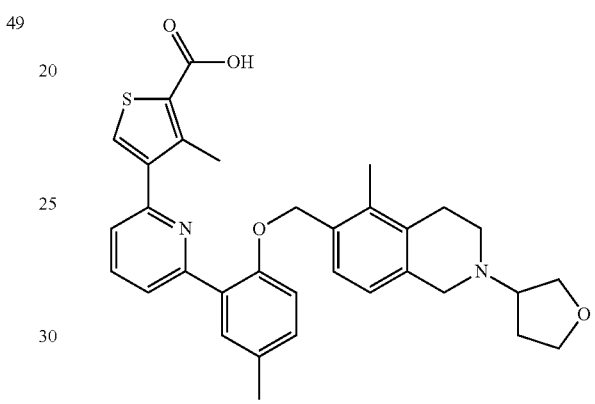
54
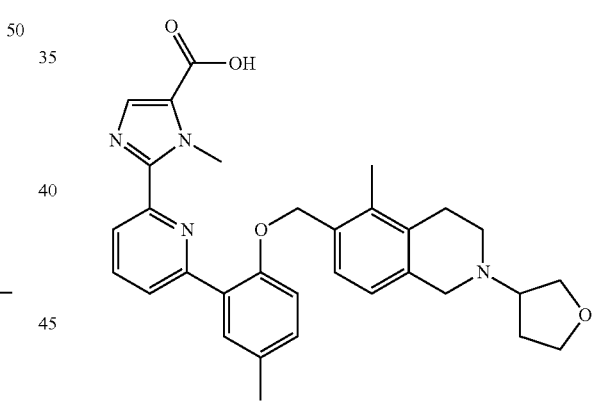
55
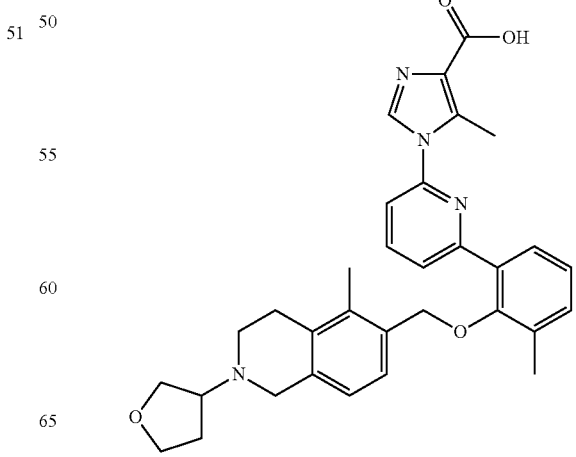

56
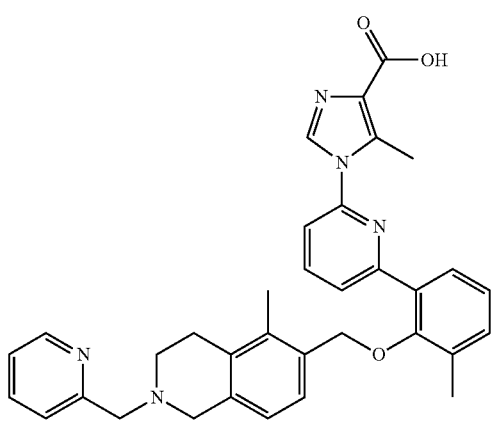 [SMILES: Cc1cccc(-c2cccc(-n3cnc(C(=O)O)c3C)n2)c1OCc1ccc2c(c1C)CCN(Cc1ccccn1)C2]
57
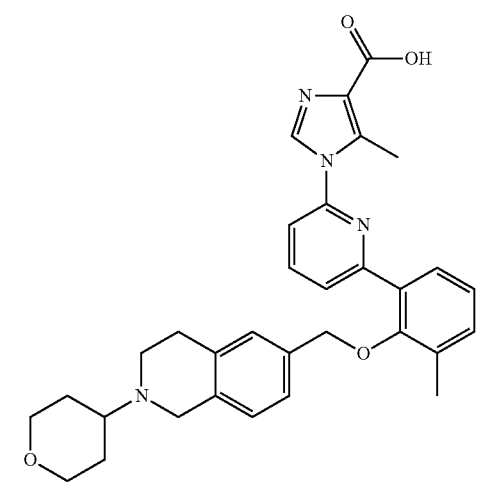 [SMILES: Cc1cccc(-c2cccc(-n3cnc(C(=O)O)c3C)n2)c1OCc1ccc2c(c1)CCN(C1CCOCC1)C2]
58
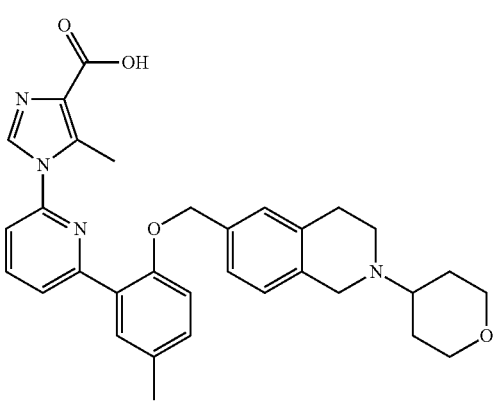 [SMILES: Cc1ccc(OCc2ccc3c(c2)CCN(C2CCOCC2)C3)c(-c2cccc(-n3cnc(C(=O)O)c3C)n2)c1]
59
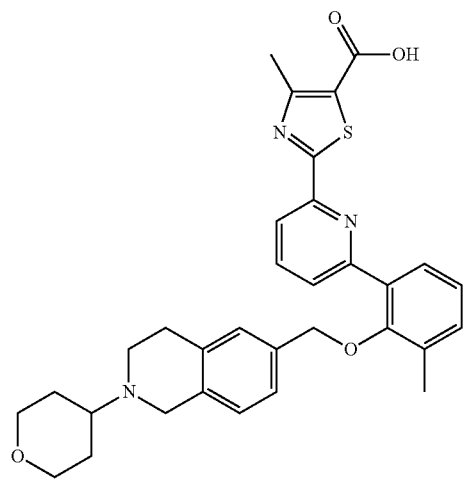 [SMILES: Cc1cccc(-c2cccc(-c3nc(C)c(C(=O)O)s3)n2)c1OCc1ccc2c(c1)CCN(C1CCOCC1)C2]
60
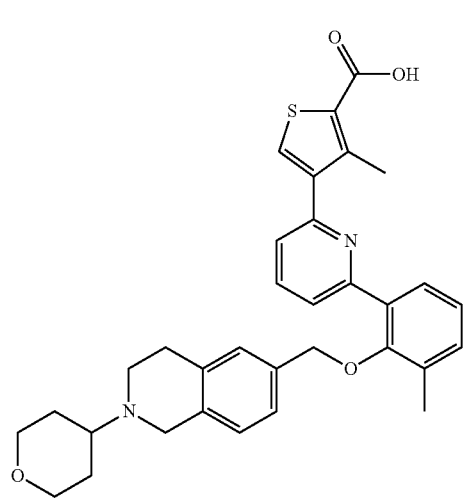 [SMILES: Cc1cccc(-c2cccc(-c3csc(C(=O)O)c3C)n2)c1OCc1ccc2c(c1)CCN(C1CCOCC1)C2]
61
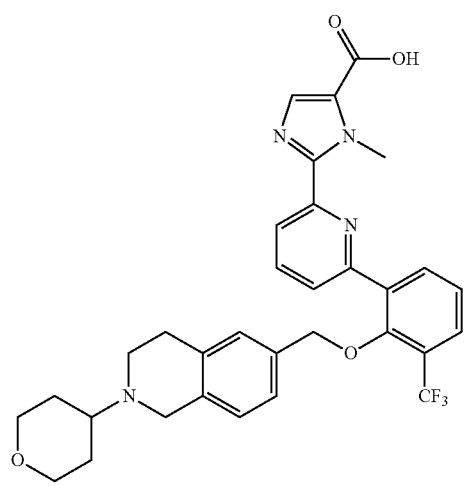 [SMILES: Cn1c(C(=O)O)cnc1-c1cccc(-c2cccc(C(F)(F)F)c2OCc2ccc3c(c2)CCN(C2CCOCC2)C3)n1]

119
-continued
62
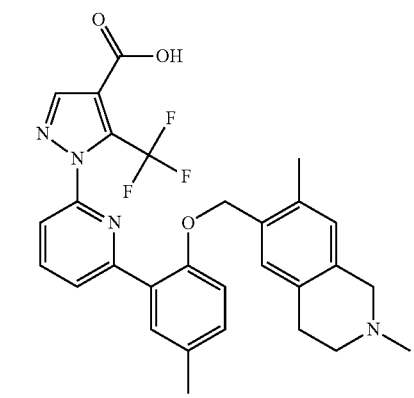
63
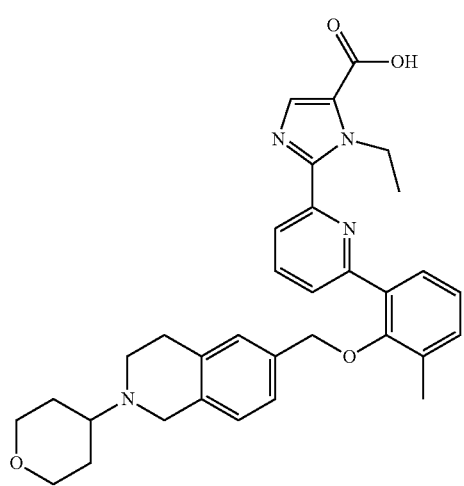
64
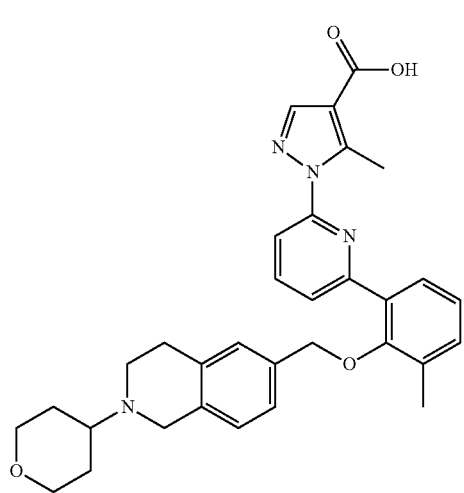 [SMILES: Cc1cccc(-c2cccc(-n3ncc(C(=O)O)c3C)n2)c1OCc1ccc2c(c1)CCN(C1CCOCC1)C2]
120
-continued
65
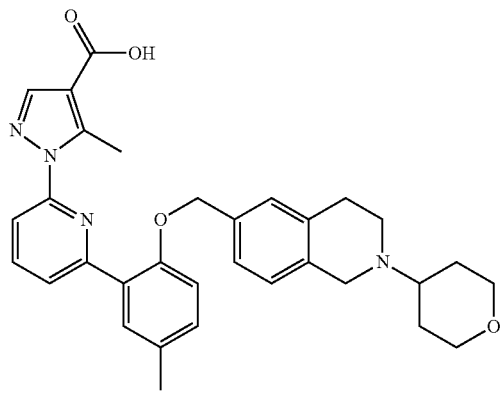 [SMILES: Cc1ccc(OCc2ccc3c(c2)CCN(C2CCOCC2)C3)c(-c2cccc(-n3ncc(C(=O)O)c3C)n2)c1]
66
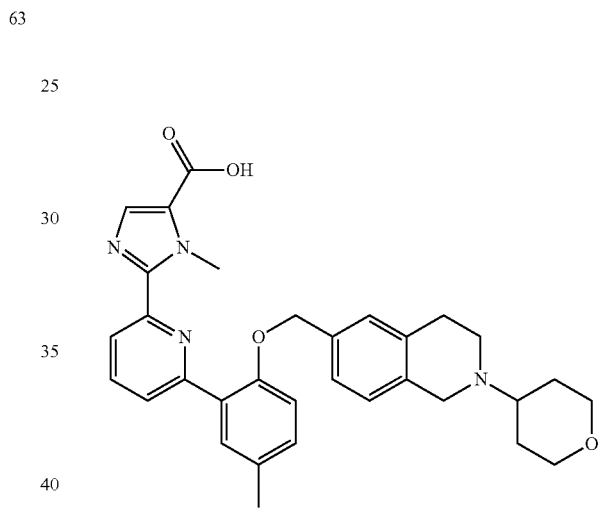
67
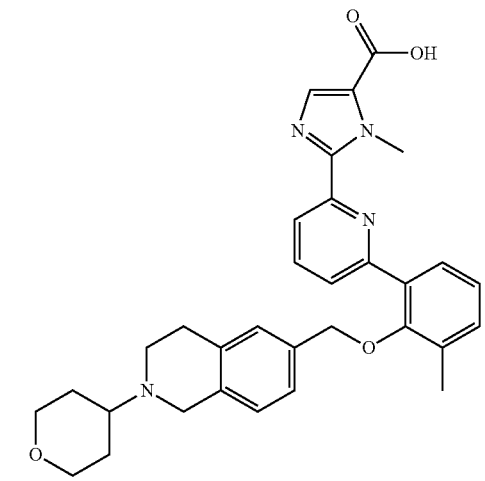 [SMILES: Cc1cccc(-c2cccc(-c3ncc(C(=O)O)n3C)n2)c1OCc1ccc2c(c1)CCN(C1CCOCC1)C2]

68
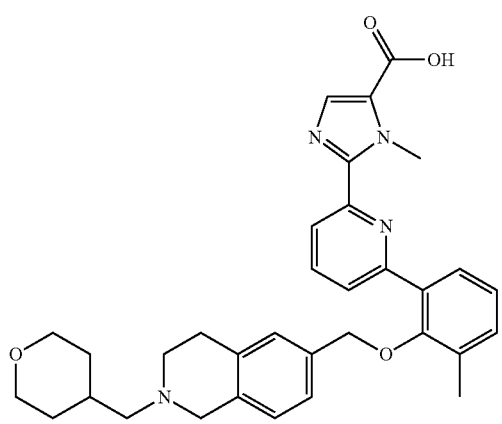 [SMILES: Cc1cccc(-c2cccc(-c3ncc(C(=O)O)n3C)n2)c1OCc1ccc2c(c1)CCN(CC1CCOCC1)C2]
69
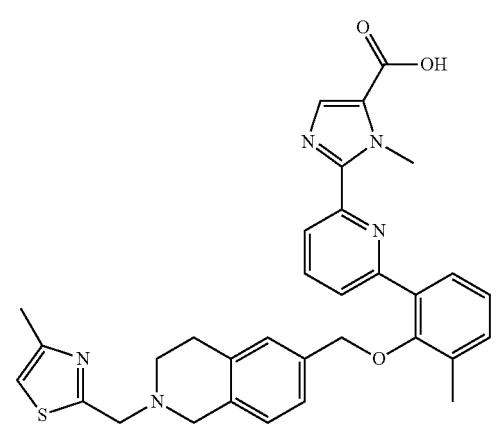 [SMILES: Cc1csc(CN2CCc3cc(COc4c(C)cccc4-c4cccc(-c5ncc(C(=O)O)n5C)n4)ccc3C2)n1]
70
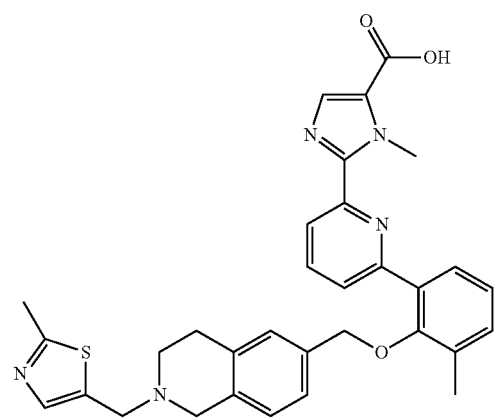 [SMILES: Cc1ncc(CN2CCc3cc(COc4c(C)cccc4-c4cccc(-c5ncc(C(=O)O)n5C)n4)ccc3C2)s1]
71
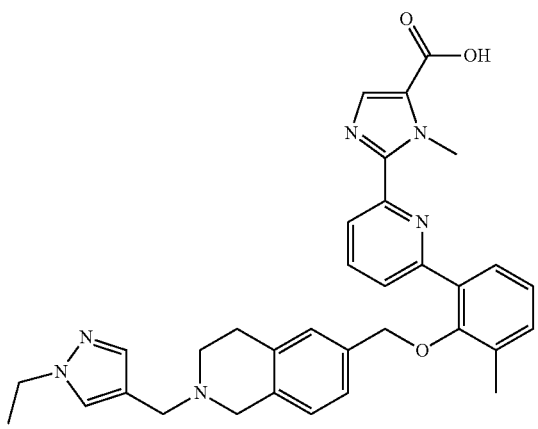
72
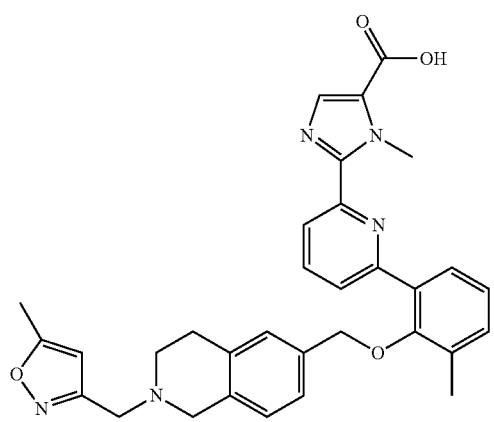 [SMILES: Cc1cc(CN2CCc3cc(COc4c(C)cccc4-c4cccc(-c5ncc(C(=O)O)n5C)n4)ccc3C2)no1]
73
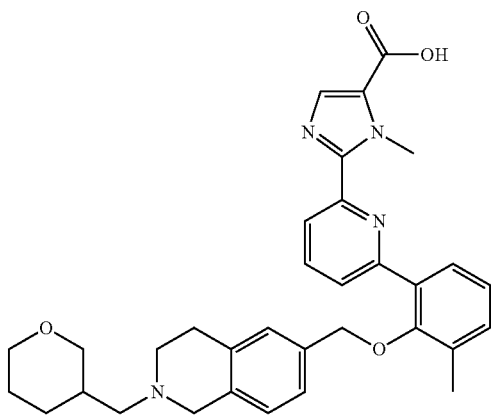 [SMILES: Cc1cccc(-c2cccc(-c3ncc(C(=O)O)n3C)n2)c1OCc1ccc2c(c1)CCN(CC1CCCOC1)C2]

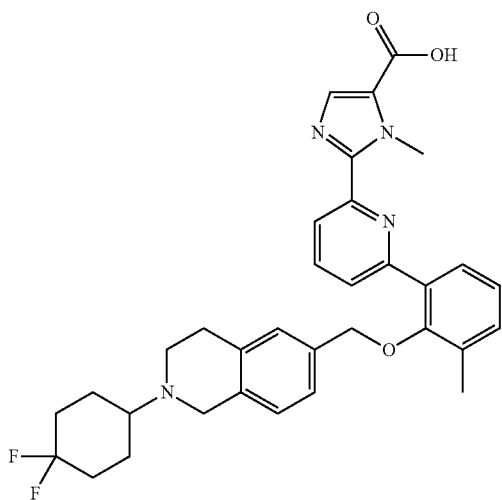 [SMILES: Cc1cccc(-c2cccc(-c3ncc(C(=O)O)n3C)n2)c1OCc1ccc2c(c1)CCN(C1CCC(F)(F)CC1)C2]
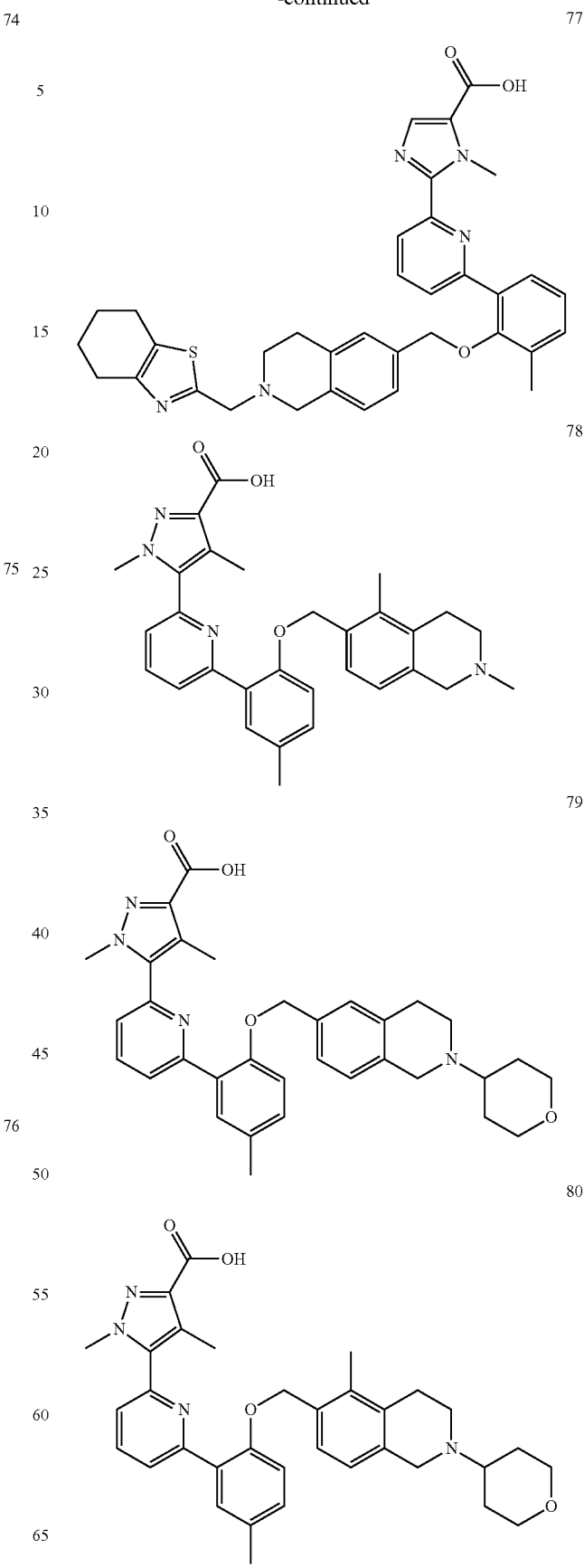

125
81
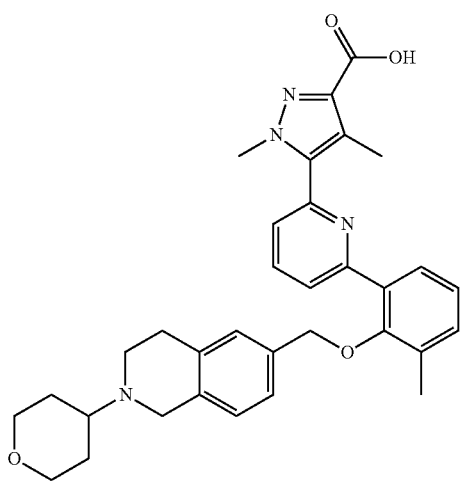 [SMILES: Cc1cccc(-c2cccc(-c3c(C)c(C(=O)O)nn3C)n2)c1OCc1ccc2c(c1)CCN(C1CCOCC1)C2]
82
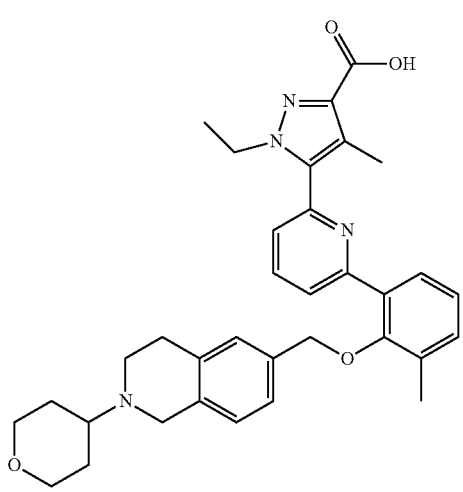
83
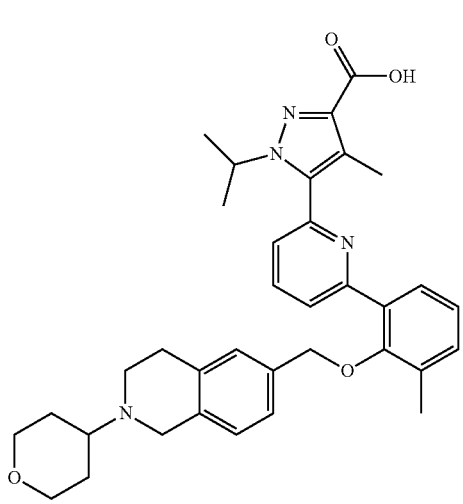 [SMILES: Cc1cccc(-c2cccc(-c3c(C)c(C(=O)O)nn3C(C)C)n2)c1OCc1ccc2c(c1)CCN(C1CCOCC1)C2]
126
84
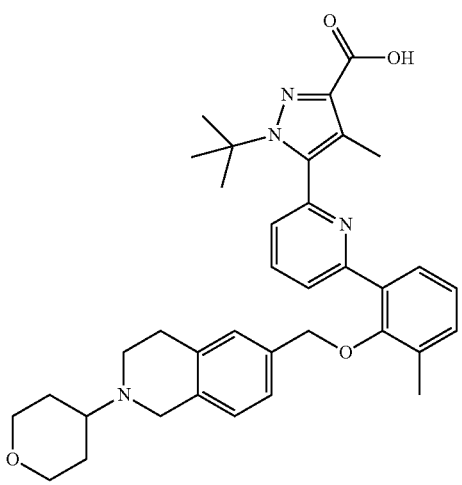 [SMILES: Cc1cccc(-c2cccc(-c3c(C)c(C(=O)O)nn3C(C)(C)C)n2)c1OCc1ccc2c(c1)CCN(C1CCOCC1)C2]
85
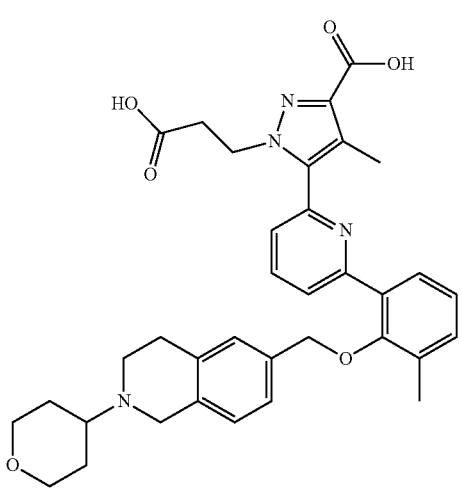 [SMILES: Cc1cccc(-c2cccc(-c3c(C)c(C(=O)O)nn3CCC(=O)O)n2)c1OCc1ccc2c(c1)CCN(C1CCOCC1)C2]
86
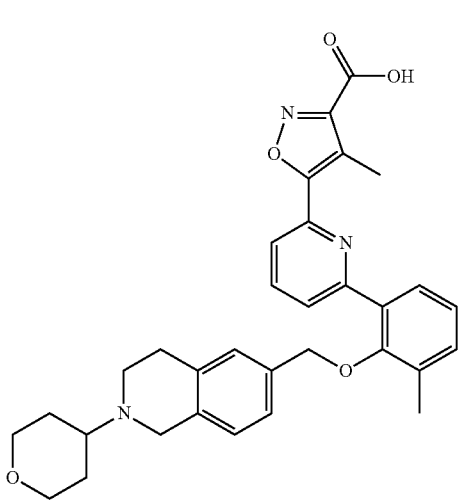 [SMILES: Cc1cccc(-c2cccc(-c3onc(C(=O)O)c3C)n2)c1OCc1ccc2c(c1)CCN(C1CCOCC1)C2]

127
-continued

87
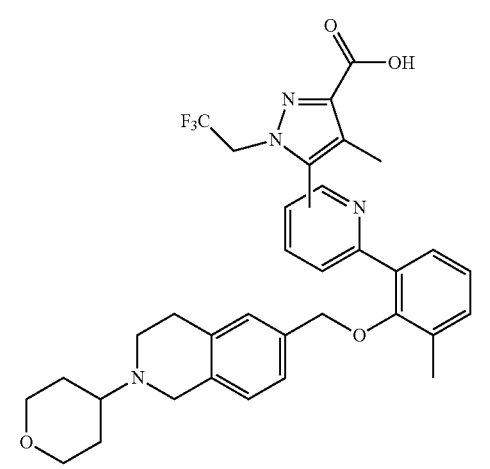

88
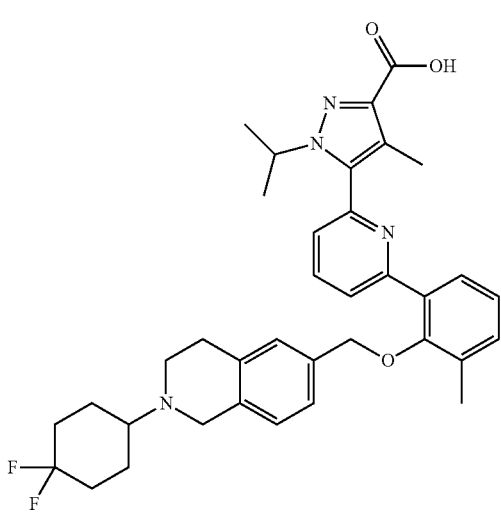 [SMILES: Cc1cccc(-c2cccc(-c3c(C)c(C(=O)O)nn3C(C)C)n2)c1OCc1ccc2c(c1)CCN(C1CCC(F)(F)CC1)C2]

89
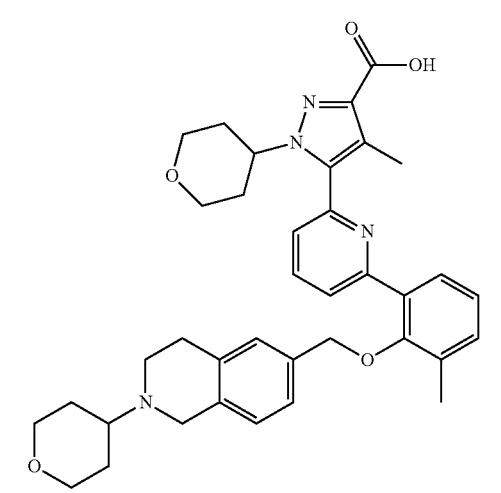 [SMILES: Cc1cccc(-c2cccc(-c3c(C)c(C(=O)O)nn3C3CCOCC3)n2)c1OCc1ccc2c(c1)CCN(C1CCOCC1)C2]

128
-continued

90
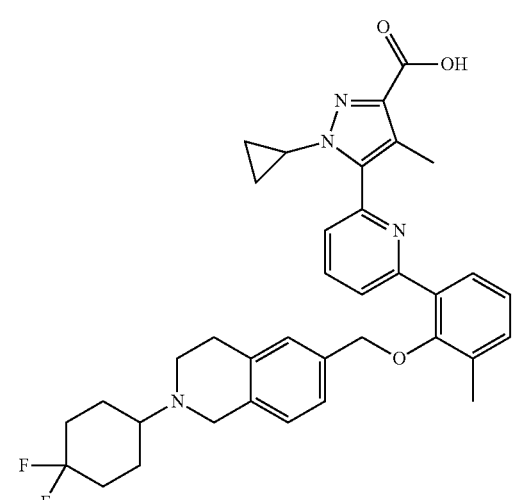

91
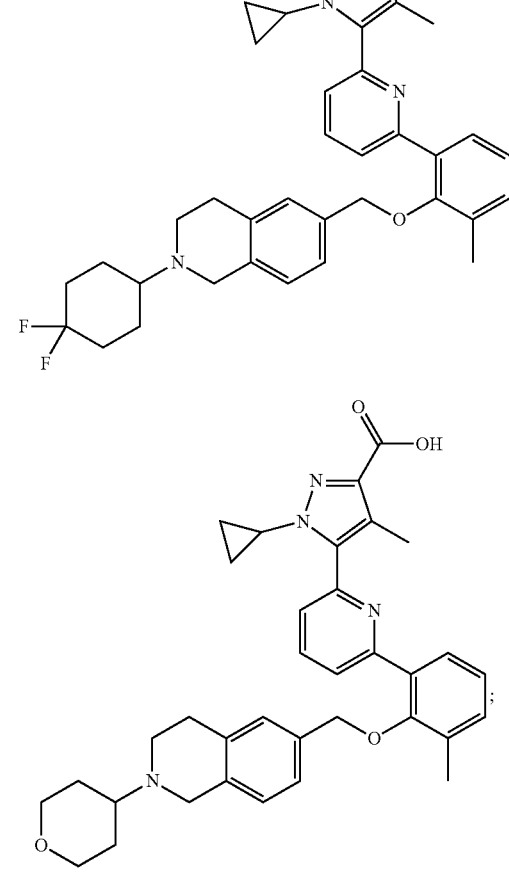

and the pharmaceutically acceptable salts thereof.

10. The compound according to claim 9 selected from the group consisting of compound numbers 1-6, 8, 12, 14, 16-35, 37, 38, 48, 50, 51, 53-56, 60-65 and 67-91;

and the pharmaceutically acceptable salts thereof.

11. A pharmaceutical composition comprising the compound of claim 1 and a pharmaceutically acceptable excipient or carrier.

12. A method of treating a disease or disorder that can be alleviated by sGC activation or potentiation comprising administering a therapeutically effective amount of a compound of claim 1 to patient in need thereof.

13. The method according to claim 12 wherein the disease or disorder is selected from a cardiovascular disease, inflammatory disease, hepatic fibrotic disorder, renal fibrotic disorder, pulmonary fibrotic disorder and cardiac fibrotic disorder.

14. The method according to claim 12 where the disease is selected from renal disease, overactive bladder, benign prostatic hyperplasia, erectile dysfunction, Alzheimer's disease, Parkinson's disease and neuropathic pain.

* * * * *